US008876698B2

(12) United States Patent
Sakamoto et al.

(10) Patent No.: US 8,876,698 B2
(45) Date of Patent: Nov. 4, 2014

(54) PRESSING MEMBER, ENDOSCOPIC TREATMENT SYSTEM, AND ENDOSCOPIC SUTURING DEVICE

(75) Inventors: Yuji Sakamoto, Tokyo (JP); Tsutomu Okada, Tokyo (JP); Satoshi Miyamoto, Tokyo (JP)

(73) Assignee: Olympus Corporation (JP)

( * ) Notice: Subject to any disclaimer, the term of this patent is extended or adjusted under 35 U.S.C. 154(b) by 1479 days.

(21) Appl. No.: 11/996,447

(22) PCT Filed: Jul. 21, 2006

(86) PCT No.: PCT/JP2006/314527
§ 371 (c)(1),
(2), (4) Date: Jul. 23, 2009

(87) PCT Pub. No.: WO2007/011039
PCT Pub. Date: Jan. 25, 2007

(65) Prior Publication Data
US 2009/0312602 A1 Dec. 17, 2009

(30) Foreign Application Priority Data

Jul. 22, 2005 (JP) .................................. 2005-213483

(51) Int. Cl.
*A61B 1/00* (2006.01)
*A61B 1/04* (2006.01)
(Continued)

(52) U.S. Cl.
CPC ....... *A61B 17/32056* (2013.01); *A61B 17/0482* (2013.01); *A61B 2017/0458* (2013.01); *A61B 18/1477* (2013.01); *A61B 17/0401* (2013.01); *A61B 2017/0464* (2013.01); *A61B 2018/1425* (2013.01); *A61B 2018/1407* (2013.01); *A61B 2017/2926* (2013.01); *A61B 2017/0451* (2013.01); *A61B 17/0218* (2013.01); *A61B 2017/0417* (2013.01); *A61B 18/1492* (2013.01);

(Continued)

(58) Field of Classification Search
CPC .. A61B 1/00073; A61B 1/00154; A61B 1/31; A61B 1/0008; A61B 1/00101; A61B 1/00128; A61B 1/00133
USPC .......... 600/104, 127, 129, 114, 105, 106, 150
See application file for complete search history.

(56) References Cited

U.S. PATENT DOCUMENTS 6,142,931 A * 11/2000 Kaji ............................. 600/114
6,632,227 B2 * 10/2003 Adams .......................... 606/110
(Continued)

FOREIGN PATENT DOCUMENTS

JP 8-547 1/1996
JP 8-336538 12/1996
(Continued)

OTHER PUBLICATIONS

Japanese Office Action mailed Feb. 1, 2011 in connection with corresponding.
(Continued)

*Primary Examiner* — Alireza Nia
(74) *Attorney, Agent, or Firm* — Ostrolenk Faber LLP

(57) ABSTRACT

An endoscopic treatment system 1 of the present invention includes an overtube 2 that is inserted into the body of a patient. An endoscope 7 and a suturing device 8 are inserted into the overtube 2. The overtube 2 has a long and flexible tube main body 3, and a chamber 4 is provided at the distal end of the tube main body 3. The chamber 4 has a lateral hole 10 formed on the lateral surface thereof. The width of the lateral hole 10 is set such that a lesion can be drawn into the lateral hole 10 while preventing other organs on the periphery of the lesion from being drawn into the lateral hole 10.

8 Claims, 52 Drawing Sheets

(51) Int. Cl.
*A61B 17/04* (2006.01)
*A61B 17/3205* (2006.01)
*A61B 17/062* (2006.01)
*A61B 18/14* (2006.01)
*A61B 17/29* (2006.01)
*A61B 17/02* (2006.01)
*A61B 17/06* (2006.01)
*A61B 17/00* (2006.01)

(52) U.S. Cl.
CPC ... *A61B 2017/06052* (2013.01); *A61B 17/0487* (2013.01); *A61B 2017/0496* (2013.01); *A61B 2017/00269* (2013.01); *A61B 2018/141* (2013.01); *A61B 2017/0409* (2013.01); *A61B 2017/00296* (2013.01); *A61B 17/29* (2013.01); *A61B 17/0469* (2013.01); *A61B 2017/00292* (2013.01); *A61B 2017/00557* (2013.01); *A61B 17/062* (2013.01)
USPC ............ 600/104; 600/114; 600/127; 600/129

(56) References Cited

U.S. PATENT DOCUMENTS

| | | | | |
|---|---|---|---|---|
| 7,063,715 | B2* | 6/2006 | Onuki et al. | 606/220 |
| 7,118,528 | B1* | 10/2006 | Piskun | 600/105 |
| 7,223,230 | B2* | 5/2007 | Zirps et al. | 600/104 |
| 2002/0065523 | A1 | 5/2002 | McAlister et al. | |
| 2002/0147447 | A1* | 10/2002 | Long | 606/41 |
| 2003/0236535 | A1* | 12/2003 | Onuki et al. | 606/144 |
| 2004/0138682 | A1 | 7/2004 | Onuki et al. | |
| 2004/0225183 | A1 | 11/2004 | Michlitsch et al. | |
| 2005/0033276 | A1 | 2/2005 | Adachi | |
| 2005/0119524 | A1 | 6/2005 | Sekine et al. | |

FOREIGN PATENT DOCUMENTS

| | | |
|---|---|---|
| JP | 10-500318 | 1/1998 |
| JP | 2004-601 | 1/2004 |
| JP | 2004-41733 | 2/2004 |
| JP | 2004-065679 | 3/2004 |
| JP | 2005-27722 | 2/2005 |
| JP | 2007-021035 | 2/2007 |
| WO | WO 94/16630 | 8/1994 |
| WO | WO 95/25468 | 9/1995 |
| WO | WO 01/54565 | 8/2001 |
| WO | WO 2007/011039 | 1/2007 |

OTHER PUBLICATIONS

Japanese Patent Application No. 2005-213483.
English translation of Japanese Office Action issued in connection with corresponding Japanese application provided as an explanation of prior art relevancy.
International Search Report mailed Oct. 24, 2006 in PCT/JP2006/314527 with English-language translation.
Written Opinion mailed Oct. 24, 2006 in PCT/JP2006/314527 with English-language translation.
Search Report issued by European Patent Office on Oct. 28, 2013 in connection with corresponding European application No. EP 06 781449.1.
European Search Report issued for corresponding European Application No. 06781449.1 mailed on Feb. 18, 2013.

* cited by examiner

PRESSING MEMBER, ENDOSCOPIC TREATMENT SYSTEM, AND ENDOSCOPIC SUTURING DEVICE

CROSS REFERENCE TO RELATED APPLICATION

The present application is a 35 U.S.C. §§371 national phase conversion of PCT/JP2006/314527, filed Jul. 21, 2006, which claims priority of Japanese Application No. 2005-213483, filed Jul. 22, 2005, the disclosure of which has been incorporated herein by reference. The PCT International Application was published in the Japanese language.

TECHNICAL FIELD

The present invention relates to a pressing member that is inserted into the body and presses a biological tissue when performing an endoscopic treatment and to an endoscopic treatment system having the pressing member. The present invention also relates to an endoscopic suturing device that sutures a biological tissue.

This application is based upon and claims the benefit of priority from the prior Japanese Patent Application No. 2005-213483 filed on Jul. 22, 2005, the entire contents of which are incorporated herein by reference.

BACKGROUND ART

When performing a treatment on an alimentary tract affected by cancer or the like within a human body, an endoscopic mucosal resection operation has been conducted in which an endoscope is inserted into the body through the mouth or the anus so as to resect a lesion. In such an operation, all layers including the affected mucosal layer and the muscular layer have been resected. However, perforations may be formed in the alimentary tract by resecting the entire layer. Thus, it is necessary to suture the perforations using an endoscopic treatment system including a suturing device in order to prevent the lumen of the alimentary tract from coalescing with the abdominal cavity via the perforations.

An endoscopic treatment system employed in such a case is provided with an overtube through which an endoscope can be inserted. The overtube has a lateral opening formed at the distal end thereof, through which all layers including the lesion are drawn and are subjected to a suture treatment. Thereafter, all layers are resected by a high-frequency snare or the like. At the time of the suture treatment, in the vicinity of the opening, a ligating tool (or a suture thread) is penetrated through all layers of the tract from the front side toward the back side thereof so that the tract including the lesion is deformed like a pouch. As a result, the front side and the back side of the tissue around the lesion are overlapped with each other. Thus, it is possible to prevent the lumen of the tract from coalescing with the abdominal cavity even when the entire lesion is resected.

JP-A-2004-65679 is an example of the prior art.

However, such an endoscopic treatment system has the following problems.

When other organs are positioned adjacent to a portion to be resected, the procedure should be performed while preventing other organs from being sutured at the time of suturing the alimentary tract. Accordingly, it has been one of the reasons for the procedure being complicated.

In addition, since the opening is formed on the lateral surface of the overtube, it is difficult to capture the image of the lesion using an image capturing portion provided at the distal end of the endoscope. Thus, it is difficult to identify the position of the lesion, deteriorating the operability of a treatment tool such as the suturing device.

Although the ligating tool or the suture thread is passed through the alimentary tract so as to substantially overlap with the same, it is difficult to maintain a closed environment until the biological tissue is coalesced.

DISCLOSURE OF THE INVENTION

The present invention has been made in view of the above-mentioned circumstances, and a main object of the present invention is to facilitate a procedure when resecting all layers including a lesion.

Another object of the present invention is to promote recovery of the lesion after the entire resection.

In order to solve the above problems, according to Aspect 1 of the present invention, there is provided a pressing member, including: a pressing member main body disposed between a treatment target portion of a biological tissue and an endoscope inserted into the body of a patient for treatment of the treatment target portion of the biological tissue, the pressing member main body being configured to press neighboring tissues around the treatment target portion by abutting the treatment target portion; and an entanglement preventing portion provided on the pressing member main body, the entanglement preventing portion being configured to, when drawing the treatment target portion into the endoscope via the pressing member main body, prevent other organs on the periphery of the treatment target portion from being drawn into the endoscope together with the treatment target portion.

According to the pressing member, the lesion is drawn in a state that biological tissue around the lesion is pressed by the pressing member. At this time, the entanglement preventing portion prevents other organs from being drawn into the endoscope together with the lesion. Therefore, only the selected biological tissue is drawn into the endoscope.

The invention according to Aspect 2 of the present invention is the pressing member according to Aspect 1, in which the entanglement preventing portion includes a first surface opposed to the endoscope; a second surface opposed to the treatment target portion; and a pressing portion disposed on a surface that connects the first surface and the second surface to each other, the pressing portion being configured to, when drawing the treatment target portion into the endoscope via the pressing member main body, produce a pressing force in a direction substantially perpendicular to the drawing-in direction of the treatment target portion, to maintain the thickness of the drawn-in treatment target portion to a predetermined thickness, and to thus prevent other organs on the periphery of the treatment target portion from being drawn into the endoscope together with the treatment target portion.

According to the pressing member, the entanglement preventing portion includes the pressing portion, and the pressing portion presses the treatment target portion so as to restrict the width of the treatment target portion. As a result, the thickness of the treatment target portion drawn into the endoscope is restricted by the pressing portion, preventing entanglement of other organs.

The invention according to Aspect 3 of the present invention is the pressing member according to Aspect 1 or 2, in which the entanglement preventing portion has an elastic member.

According to the pressing member, when the treatment target portion is drawn into the endoscope while elastically deforming the elastic member, the thickness of the treatment target portion is restricted by the restring force of the elastic member. By setting the elastic coefficient of the elastic member to a value that does not allow the entanglement of other organs or the like, it is possible to prevent the entanglement of other organs.

The invention according to Aspect 4 of the present invention is the pressing member according to any one of Aspects 1 to 3, in which the pressing member main body includes an opening through which the treatment target portion is drawn into the endoscope via the pressing member main body; a first entanglement preventing portion disposed on the periphery of the opening; and a second entanglement preventing portion disposed opposite the first entanglement preventing portion, the first and second entanglement preventing portion being configured to sandwich the treatment target portion therebetween, to maintain the thickness of the treatment target portion to a predetermined thickness, and to thus prevent other organs on the periphery of the treatment target portion from being drawn into the endoscope via the pressing member main body, together with the treatment target portion.

According to the pressing member, although the treatment target portion is drawn into the endoscope through the opening, the treatment target portion is sandwiched between the first and second entanglement preventing portion in the course of the drawing operation. Therefore, the thickness of the treatment target portion drawn into the endoscope is restricted to the gap defined between the first and second entanglement preventing portion. Accordingly, by setting the gap between the first and second entanglement preventing portion to a size that does not allow the entanglement of other organs, it is possible to prevent the entanglement of other organs.

The invention according to Aspect 5 of the present invention is the pressing member according to Aspect 1, in which the entanglement preventing portion is a displacing member that can be located between the treatment target portion and other organs on the periphery of the treatment target portion, and the pressing member main body includes a first opening through which the treatment target portion is drawn into the endoscope via the pressing member; and a second opening disposed closer to a proximal end than the first opening, through which the displacing member is delivered from the endoscope toward the treatment target portion via the pressing member.

According to the pressing member, the displacing member is inserted between the treatment target portion and other organs through the second opening so that the treatment target portion is sandwiched between the displacing member and the first opening. Accordingly, even when the treatment target portion is inserted into the endoscope, other organs are not drawn into the endoscope by the presence of the displacing member.

The invention according to Aspect 6 of the present invention is the pressing member according to any one of Aspects 1 to 5, in which the pressing member main body is movable with respect to the endoscope.

According to the pressing member, since the pressing member main body is movable with respect to the endoscope, it becomes easy to identify the treatment target portion by means of the endoscope. Also, it is easy to grasp the treatment target portion by means of a treatment tool inserted through the endoscope.

The invention according to Aspect 7 of the present invention is the pressing member according to any one of Aspects 1 to 6, in which the pressing member main body includes an overtube having a lumen that allows insertion of the endoscope therethrough; a flexible insertion guide that extends from a distal end of the overtube; a tapered portion corresponding to a transitional portion between the overtube and the insertion guide; and an opening formed in the tapered portion and having a space through which the treatment target portion is drawn in.

According to the pressing member, the overtube promotes the insertion of the endoscope or the like. Since the flexible insertion guide is deformed while assuming the curved shape of the alimentary tract, flexible insertion of the overtube is facilitated. Since the opening is formed in the tapered portion, it is possible to identify the treatment target portion and to perform the treatment without needing to bend the endoscope greatly.

According to Aspect 8 of the present invention, there is provided an endoscopic treatment system including the endoscope; the pressing member according to any one of Aspects 1 to 6; a draw-in portion for drawing the treatment target portion into an endoscope; and a treatment portion for treating the treatment target portion.

According to the endoscopic treatment system, the treatment target portion is drawn into the endoscope using the draw-in portion, and the biological tissue is sutured or resected using the treatment portion. At this time, since the treatment target portion is drawn in via the pressing member, it is possible to prevent the entanglement of other organs.

According to Aspect 9 of the present invention, there is provided an endoscopic suturing device including: a main body having a distal end portion, a proximal end portion, and a longitudinal shaft; a suture unit provided at the distal end portion of the main body, and having a grasping unit that grasps a biological tissue and a tissue penetrating needle that sutures the biological tissue grasped by the grasping unit; a first grasping piece provided on the suture unit; a second grasping piece provided on the suture unit and configured to be freely movable toward or away from the first grasping piece in a relative manner; a first convex portion having a first vertex portion that protrudes from the first grasping piece toward the second grasping piece; a second convex portion disposed adjacent to the first convex portion and having a second vertex portion that protrudes from the first grasping piece toward the second grasping piece; a third convex portion having a third vertex portion that protrudes from the second grasping piece toward the first grasping piece so as to be engaged between the first convex portion and the second convex portion; the tissue penetrating needle being configured, when the first grasping piece is moved closer to the second grasping piece, to be moved forward or backward through an area closer to the first grasping piece than a plane including the first vertex portion, an area closer to the first grasping piece than a plane including the second vertex portion, and an area closer to the second grasping piece than a plane including the third vertex portion; and a suture member detachably attached to the tissue penetrating needle and having a stopper at the proximal end side in the penetration direction of the tissue penetrating needle.

According to the endoscopic suturing device, two biological tissues on both sides of a resected portion of the treatment target portion are sandwiched in a corrugated shape between the first and second grasping pieces having the convex portions. Then, in a state that the two biological tissues are overlapped with each other, the tissue penetrating needle is penetrated through the overlapped biological tissues, whereby the two biological tissues are joined with each other. Since the stopper is provided at the proximal end (the endoscope side) of the suture member, it is possible to maintain the sutured state of the treatment target portion by only means of a proximal-side operation.

The invention according to Aspect 10 of the present invention is the endoscopic suturing device according to Aspect 9, in which the endoscopic suturing device further includes a tissue restricting member disposed between neighboring tissues adjacent to a treatment target tissue and the suture unit, the tissue restricting member being configured to place the treatment target tissue between the distal end portion and the proximal end portion of the grasping unit.

According to the endoscopic suturing device, the tissue restricting member is placed between the neighboring tissues and the treatment target tissue so that the length of the biological tissue to be sutured is restricted by the tissue restricting member. As a result, the biological tissue to be sutured is received between the distal end portion and the proximal end portion of the grasping unit, enabling a secure suture treatment without leaving any portion of the biological tissue to be sutured.

The invention according to Aspect 11 of the present invention is the endoscopic suturing device according to Aspect 10, in which the tissue restricting member is a pressing member main body that is disposed between a treatment target portion of a biological tissue and an endoscope inserted into the body of a patient for treatment of the treatment target portion of the biological tissue, the pressing member main body being configured to press the neighboring tissues around the treatment target portion by abutting the treatment target portion, and the pressing member main body includes: a first surface opposed to the endoscope; a second surface opposed to the treatment target portion; and a tissue restricting portion disposed on a surface that connects the first surface and the second surface to each other, the pressing portion being configured to, when drawing the treatment target portion into the endoscope via the pressing member main body, produce a pressing force in a direction substantially perpendicular to the drawing-in direction of the treatment target portion, and to maintain the longitudinal length of the drawn-in treatment target portion so as to be received between the distal end portion and the proximal end portion of the grasping unit.

In the endoscopic suturing device, the treatment target portion is drawn in a state that the neighboring tissues are pressed by the pressing member main body. At this time, the length of the biological tissue to be sutured is restricted by the tissue restricting member, and the biological tissue to be sutured is received between the distal end portion and the proximal end portion of the suture unit, enabling a secure suture treatment without leaving any portion of the biological tissue to be sutured.

According to the present invention, when performing a treatment by drawing the treatment target portion into the endoscope, the entanglement preventing portion prevents other organs from being drawn into the endoscope together with the treatment target portion. Therefore, it is easy to confirm an occurrence of the entanglement of other organs. Accordingly, it is possible to simplify the procedure and to shorten the procedure time.

Since the flexible insertion guide is provided at the distal end of the overtube, it is easy to direct the distal end portion of the overtube to follow the path of the endoscope or the body cavity. Accordingly, it is easy to introduce the distal end portion of the overtube to the treatment target portion.

Since the suture treatment can be performed in such a manner that the suturing tool is penetrated through the corrugated treatment target portion, it is possible to suture the two biological tissues of the treatment target portion in a state that the two biological tissues are folded in multiple layers. Accordingly, it is possible to suture perforations formed by the resection in a secure manner while maintaining a closed environment until the perforations are coalesced.

BRIEF DESCRIPTION OF THE DRAWINGS

FIG. 15 is a diagram showing the state in which a biological tissue is drawn in.

DESCRIPTION OF REFERENCE NUMERALS AND SIGNS

1: ENDOSCOPIC TREATMENT SYSTEM
2: OVERTUBE (PRESSING MEMBER MAIN BODY, TISSUE RESTRICTING MEMBER)
4a, 93a, 111A: FIRST SURFACE
4b, 93b, 111B: SECOND SURFACE
4c, 4d, 93c, 111C: PRESSING PORTION
5: INSERTION GUIDE
6: TAPERED PORTION
7: ENDOSCOPE (TISSUE RESTRICTING MEMBER)
8: SUTURING DEVICE (TREATMENT PORTION, ENDOSCOPIC TREATMENT DEVICE)
10, 90, 94, 100: LATERAL HOLE (ENTANGLEMENT PREVENTING PORTION)
15: GRASPING FORCEPS (DRAW-IN PORTION)
21: FIRST INSERTION PORTION (MAIN BODY)
27: SECOND INSERTION PORTION (MAIN BODY)
30, 180, 200, 210, 240: SUTURE UNIT
32: FIRST JAW (GRASPING UNIT, FIRST GRASPING PIECE)
34: TOOTH (FIRST CONVEX PORTION)
34a: VERTEX PORTION (FIRST VERTEX PORTION)
35: TEETH (SECOND CONVEX PORTION)
35a: VERTEX PORTION (SECOND VERTEX PORTION)
42: SECOND JAW (GRASPING UNIT, FIRST GRASPING PIECE)

44: TEETH (THIRD CONVEX PORTION)
44a: VERTEX PORTION (THIRD VERTEX PORTION)
48: TISSUE RESTRICTING PORTION
51: TISSUE PENETRATING NEEDLE
62: SUTURE THREAD (SUTURE MEMBER)
65: STOPPER
85: SNARE (TISSUE RESTRICTING MEMBER)
87: SNARE PORTION (TISSUE RESTRICTING PORTION)
91, 95: PRESSING MEMBER
93: PRESSING MEMBER MAIN BODY
96: ARM (PRESSING MEMBER MAIN BODY)
110: LATERAL HOLE (OPENING, FIRST OPENING)
111: SLIDER COVER (ENTANGLEMENT PREVENTING PORTION)
130: ELASTIC MEMBER
140: VALVE BODY (FIRST ENTANGLEMENT PREVENTING PORTION)
141: VALVE BODY (SECOND ENTANGLEMENT PREVENTING PORTION)
151: OPENING (SECOND OPENING)
156: BALLOON (DISPLACING MEMBER)
163: BASKET (DISPLACING MEMBER)
168: DISPLACING MEMBER
170: LATERAL HOLE (OPENING)
W1: LESION (TREATMENT TARGET PORTION)
α, β: BIOLOGICAL TISSUE (TREATMENT TARGET PORTION)
W3: OTHER INTERNAL ORGANS

BEST MODE FOR CARRYING OUT THE INVENTION

Embodiment 1

Hereinafter, a first embodiment will be described in detail with reference to FIGS. 1 to 28.

Figure 1:
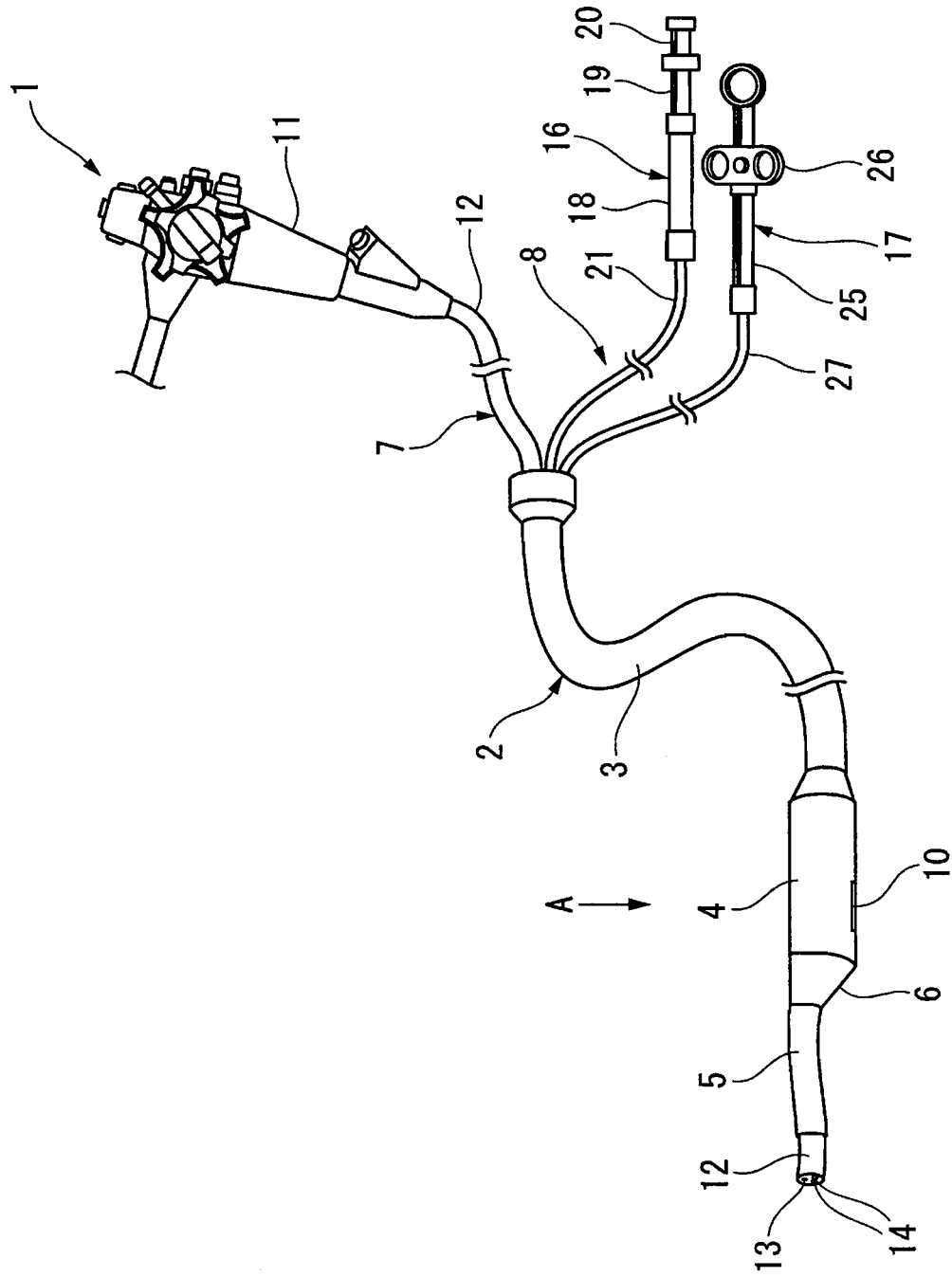
FIG. 1 is a diagram showing the structure of an endoscopic treatment system in accordance with embodiments of the present invention.

As shown in FIG. 1, an endoscopic treatment system 1 includes an elongated overtube 2 serving as a pressing member main body that is inserted into the body of a patient. The overtube 2 is provided with a chamber 4 at a distal end of a flexible tube main body 3. The chamber 4 extends in a cylindrical shape while the diameter thereof is enlarged from the distal end portion of the tube main body 3. A flexible insertion guide 5 is provided on the distal end surface of the chamber 4. The insertion guide 5 is a cylindrical member that is located at a position axially offset with respect to the chamber 4. A transitional portion where the distal end portion of the chamber 4 transitions into the insertion guide 5 is formed as a tapered portion 6 that is cut obliquely toward the insertion guide 5.

Figure 2:
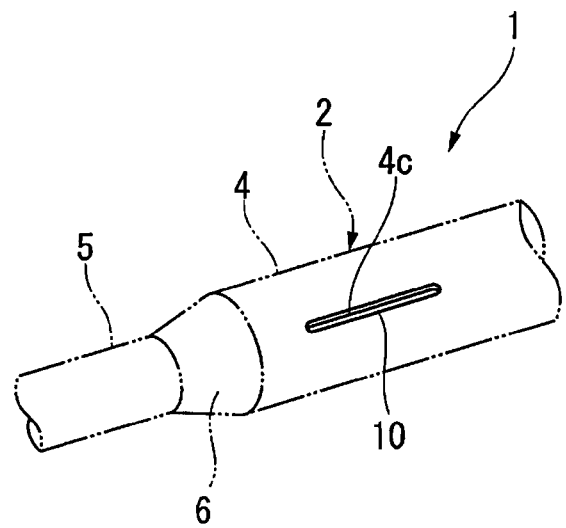
FIG. 2 is a diagram taken from the direction of the arrow A in FIG. 1.
Figure 3:
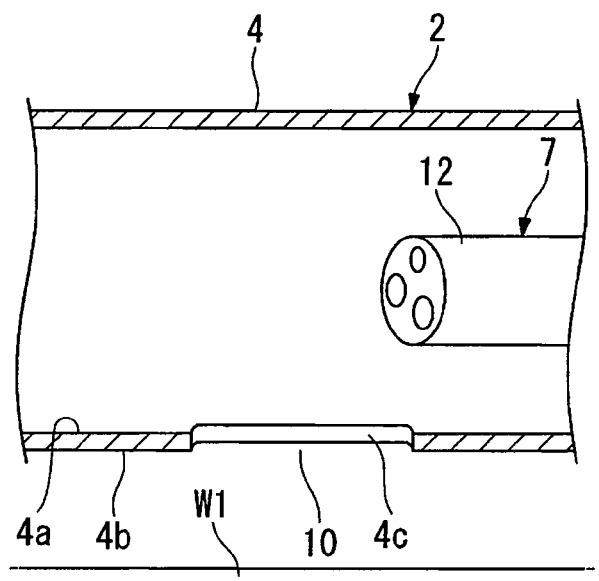
FIG. 3 is a sectional view of a chamber.

On a more proximal side in the longitudinal direction of the chamber 4 than the tapered portion 6, a lateral hole 10 is formed parallel to the longitudinal direction in a long and thin shape. As shown in FIGS. 2 and 3, the chamber 4 of the overtube 2 functions as an entanglement preventing portion that includes a first surface 4a that is opposed to an endoscope 7 side, a second surface 4b that is opposed to a treatment target portion (a lesion W1), and a pressing portion 4c provided on a portion that connects the first surface 4a and the second surface 4b to each other.

The pressing portion 4c is formed of a wall surface of the lateral hole 10 in the circumferential direction of the chamber 4. The distance between upper and lower sides of the pressing portion 4c corresponds to the width of the lateral hole 10 in the circumferential direction of the chamber 4. The size (distance) of the pressing portion 4c is set such that when a treatment target portion, a biological tissue of an alimentary tract to be resected entirely, is entered into the chamber 4, the thickness of the treatment target portion is restricted to a predetermined value so as to prevent other internal organs from entering into the chamber 4. Specifically, when all layers of the alimentary tract have a thickness ranging from 1.0 to 1.5 mm, the size of the pressing portion 4c ranges from 2 to 3 mm corresponding to twice the thickness of the all layers.

In the overtube 2 having the insertion guide 5, an endoscope 7 and an endoscopic suturing device (hereinafter referred to as a suturing device) 8 are inserted from a proximal end side thereof. As shown in FIG. 1, the endoscope 7 includes an operation portion 11 that an operator operates with. At the distal end of the operation portion 11, an elongated flexible insertion portion 12 is provided.

Figure 4:
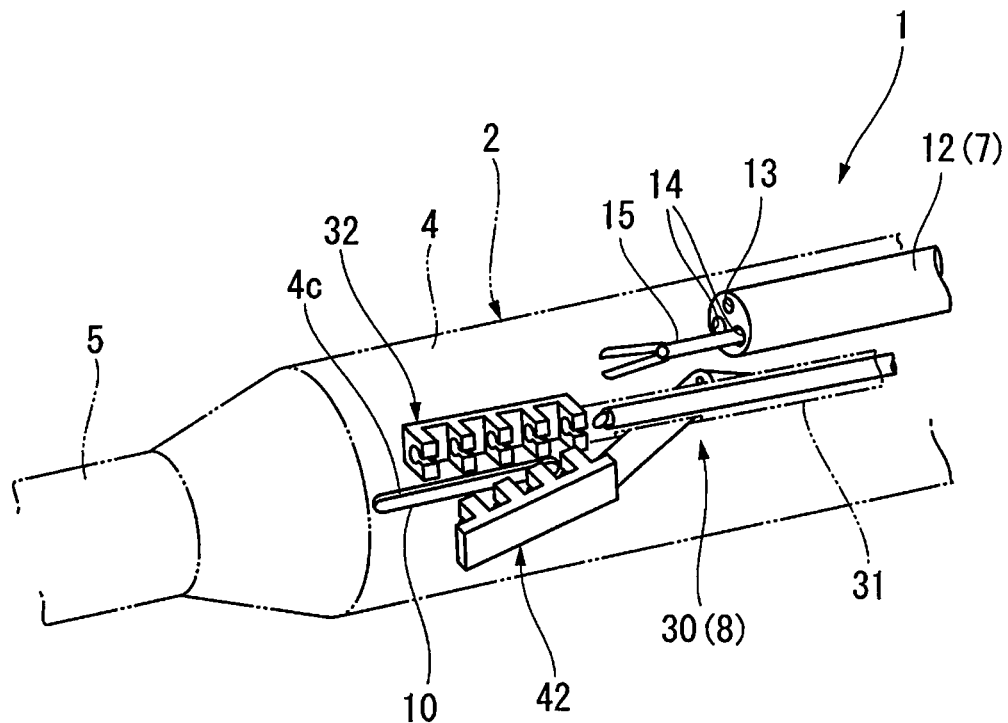
FIG. 4 is a conceptual diagram showing the internal structure of the chamber.

As shown in FIG. 4, the distal end portion of the insertion portion 12 is inserted into the chamber 4. On the distal end surface of the insertion portion 12, an image capturing portion 13 that captures an image of the internal body and a distal opening of a treatment tool channel 14 are provided. The treatment tool channel 14 passes through the endoscope 7 into the operation portion 11. Through the treatment tool channel 14, an endoscopic treatment tool such as a grasping forceps 15 can be inserted, or operations such as suction or liquid delivery can be performed.

As shown in FIG. 1, the suturing device 8 includes a first operation portion 16 and a second operation portion 17 that an operator operates with. The first operation portion 16 is configured such that a hollow piston 19 is inserted into an operation portion main body 18 so as to be freely moved forward or backward. To the proximal end portion of the piston 19, a hollow slider 20 is inserted so as to be freely moved forward or backward with respect to the piston 19. On the distal end of the first operation portion 16, a proximal end portion of a first insertion portion 21 that is flexible and elongated is attached. The first insertion portion 21 is inserted through the inside of a sheath so that a hollow liquid supply tube connected to the piston 19 can be freely moved forward or backward. To the liquid supply tube, a pusher rod connected to the slider 20 is inserted so as to be freely moved forward or backward.

The second operation portion 17 is configured such that a slider 26 is attached to an operation portion main body 25 so as to be freely moved forward or backward. A hole is formed on the proximal end of the operation portion main body 25 and on the slider 26 so that an operator can grasp the second operation portion 17 with his fingers hooked on the holes. On the distal end of the second operation portion 17, a proximal end portion of a second insertion portion 27 that is flexible and elongated is attached. The second insertion portion 27 is inserted through the inside of a sheath so that an operation wire connected to the slider 26 can be freely moved forward or backward. At the distal end portion of the first and second insertion portions 21 and 27 that constitute a main body portion of the suturing device 8, a suture unit 30 is provided, as shown in FIG. 4.

Figure 5:
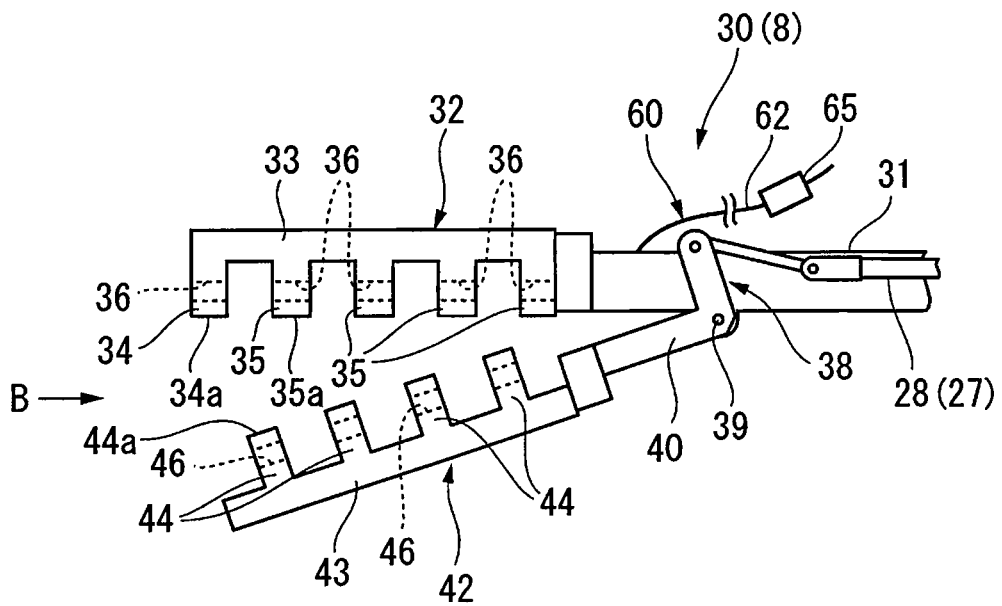
FIG. 5 is a diagram showing the structure of a suture unit of a suturing device, showing the state in which a grasping unit is open.

As shown in FIGS. 4 and 5, the suture unit 30 includes a shaft portion 31 to which the sheaths of the first and second insertion portions 21 and 27 (see FIG. 1) are connected. At the distal end of the shaft portion 31, a first jaw 32 serving as a first grasping piece is provided. The first jaw 32 has a proximal end portion thereof located at a position offset from the central axis of the shaft portion 31, and a main body portion 33 that extends in the insertion direction from the proximal end portion, i.e., in the direction for being inserted into the body. At the distal end portion of the main body portion 33, a tooth 34 serving as a first convex portion is provided so as to extend in a direction perpendicular to the longitudinal direction of the main body portion 33 over the central axis of the shaft portion 31.

Figure 6:
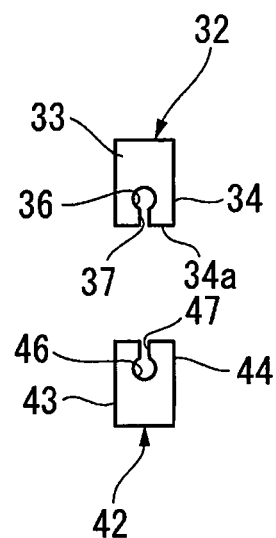
FIG. 6 is a diagram taken from the direction of the arrow B in FIG. 5.

Between the tooth 34 and the proximal end of the main body portion 33, a plurality of teeth 35 serving as a second convex portion is arranged at regular intervals. The teeth 35 have the same shape as that of the tooth 34, so that the first jaw 32 has a comb-teeth shape as a whole. A vertex portion 34a (a first vertex portion) of the tooth 34 and vertex portions 35a (a second vertex portion) of the teeth 35 are formed of a flat surface that is parallel in the longitudinal direction. As shown in FIGS. 5 and 6, through-holes 36 are formed in the teeth 34 and 35 so as to penetrate through the teeth 34 and 35 in a direction parallel to the longitudinal direction of the first jaw 32. Also, in the teeth 34 and 35, slits 37 that are open to the vertex portions 34a and 35a of the teeth 34 and 35 are formed so as to be connected to the through-holes 36.

Around the shaft portion 31, an operation wire 28 is wound so as to be freely moved forward or backward. The operation wire 28 passes through the inside of the second insertion portion 27 shown in FIG. 1 and is connected to the slider 26 of the second operation portion 17. On the distal end portion of the operation wire 28, a link mechanism 38 is attached. The link mechanism 38 is provided with an L-shaped lever 40 that is supported on the shaft portion 31 by a pin 39 so as to pivot in response to the forward and backward movement of the operation wire 28.

The lever 40 is attached so as to pivot about a position located on the opposite side in the offset direction of the first jaw 32. On the distal end of the lever 40, a proximal end portion of a second jaw 42 serving as a second grasping piece is attached. The second jaw 42 has an elongated main body portion 43. On the main body portion 43, a plurality of teeth 44 serving as a third convex portion is arranged at regular intervals so as to extend in a direction perpendicular to the longitudinal direction. The second jaw 42 has a comb-teeth shape as a whole. The teeth 44 of the second jaw 42 and the teeth 34 and 35 of the first jaw 32 are arranged in an alternating manner. The vertex portions 44a (third vertex portion) of the teeth 44 are formed of a flat surface. Like the first jaw 32, each of the teeth 44 has a through-hole 46 and a slit 47.

Figure 7:
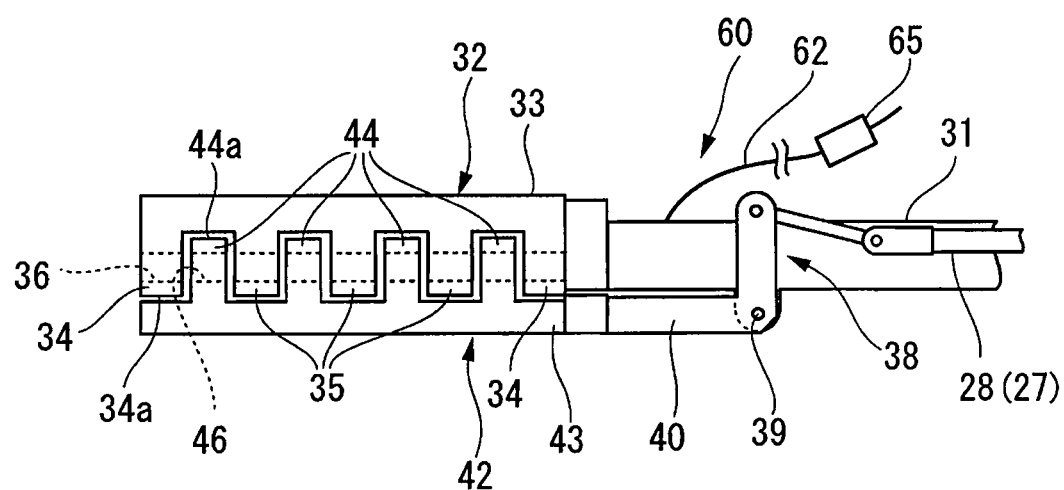
FIG. 7 is a diagram showing the state in which the grasping unit is closed.

A grasping unit formed by the first and second jaws 32 and 42 is opened as shown in FIG. 5 when the operation wire 28 is moved forward, and as shown in FIG. 7, the grasping unit is closed when the operation wire 28 is moved backward. In the state in which the first and second jaws 32 and 42 are closed, the teeth 34, 35, and 44 are sequentially arranged in the longitudinal direction so that the through-holes 36 and 46 are linearly aligned. Between the teeth 34, 35, and 44, and between the vertex portions 34a, 35a, and 44a of the teeth 34, 35, and 44 and the main body portions 33 and 43 opposed to these portions, gaps that have a crank shape with a predetermined width are defined.

Figure 8:
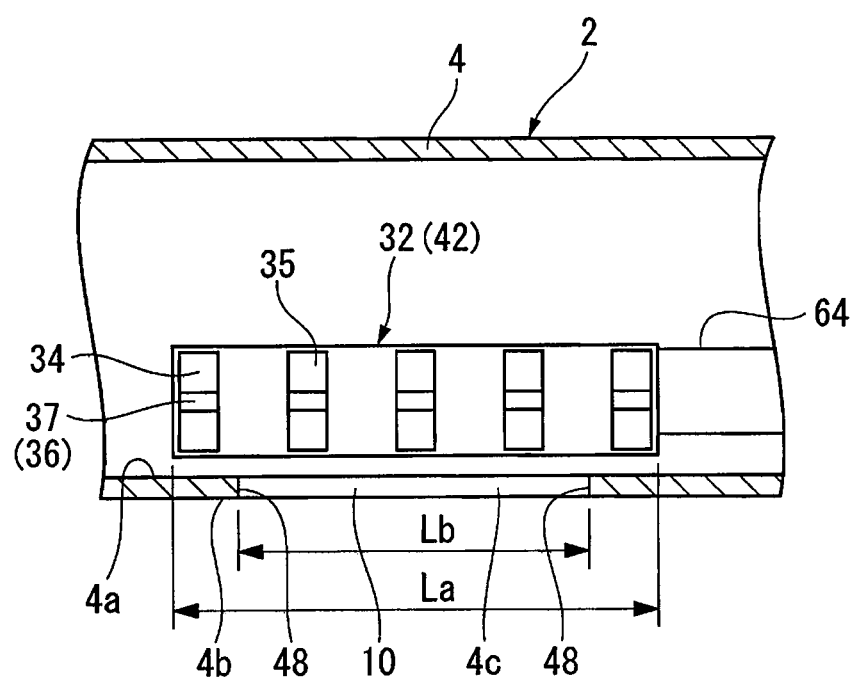
FIG. 8 is a diagram showing the lengths of a jaw and a lateral hole.

As shown in FIG. 8, the length La between the proximal end portion and the distal end portion of the first and second jaws 32 and 42 is set greater than the longitudinal length Lb of the lateral hole 10. The wall surfaces in the longitudinal direction of the lateral hole 10 function as tissue restricting portions 48. The operations of the tissue restricting portions 48 will be described later.

Figure 9:
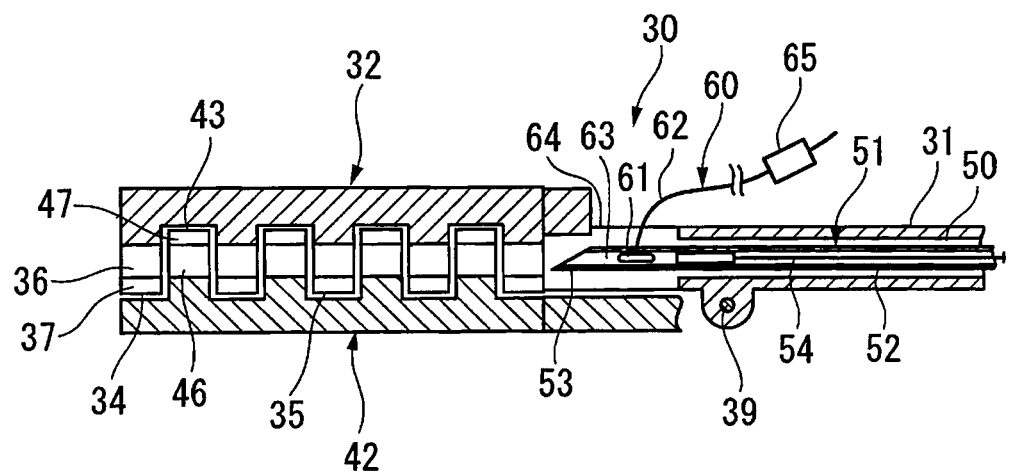
FIG. 9 is a sectional view of FIG. 7.

As shown in FIG. 9, a through-hole 50 is formed in the shaft portion 31 along the longitudinal direction thereof. A tissue penetrating needle 51 is inserted into the through-hole 50. The tissue penetrating needle 51 includes a needle portion 53 that is attached to the distal end of the liquid supply tube 52 of the first insertion portion 21.

The needle portion 53 is formed of a hollow member having a sharply cut distal end, and the pusher rod 54 is inserted through the needle portion 53 and the liquid supply tube 52 so as to be freely moved forward or backward. Therefore, when the piston 19 of the first operation portion 16 shown in FIG. 1 is moved forward or backward, the liquid supply tube 52 and the needle portion 53 are moved forward or backward. When the slider 20 is moved forward or backward with respect to the piston 19, the pusher rod 54 is moved forward or backward into the liquid supply tube 52 and the needle portion 53.

The outer diameter of the needle portion 53 and the liquid supply tube 52 is set smaller than the outer diameter of the through-holes 36 and 46. When the needle portion 53 is moved forward to the greatest extent, the needle portion 53 is passed through the first and second jaws 32 and 42. In the needle portion 53, a T bar 61 of the suturing tool 60 is received.

The suturing tool 60 has the T bar 61 formed of a long and thin member. The T bar 61 has a thickness that can be pressed against the distal end of the pusher rod 54. From a portion near the center of the T bar 61, a suture thread 62 serving as a suture member is extended. The suture thread 62 is passed through a slit 63 formed on the lateral portion of the needle portion 53 and is again passed through a hole 64 formed on the lateral portion of the shaft portion 31, finally being drawn out from the suture unit 30. To the proximal end side of the suture thread 62, a stopper 65 serving as a fixing member is press-fitted so as to be freely moved forward or backward.

Next, operations of the present embodiment will be described. The following descriptions will be made for the case in which a treatment is performed on a lesion in the intestinal tract. However, the treatment target portion is not limited to this.

Figure 10:
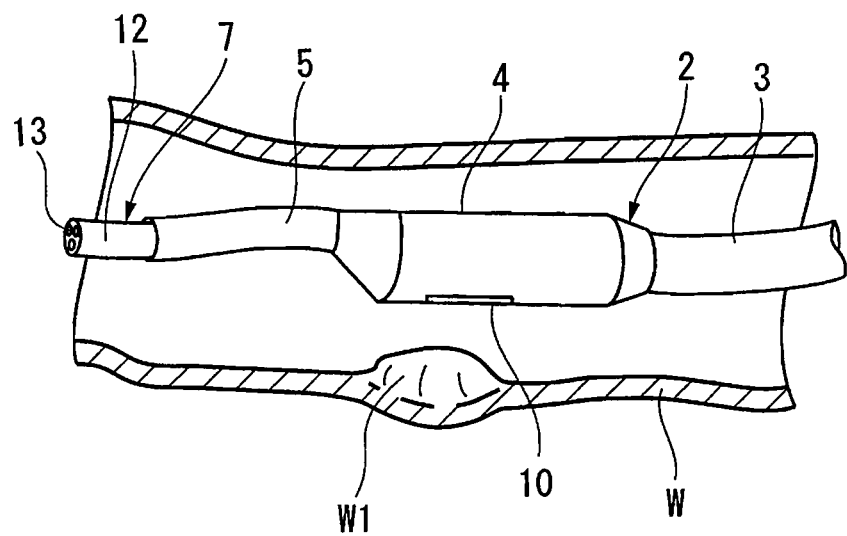
FIG. 10 is a diagram for explaining a procedure, showing the state in which an overtube is inserted into the body of a patient.

As shown in FIG. 1, the endoscope 7 is inserted through the overtube 2, and the distal end portion of the insertion portion 12 is protruded out from the distal end of the insertion guide 5. While observing the image captured by the image capturing portion 13 of the endoscope 7, the overtube 2 is inserted into the body through the insertion guide 5. Since the insertion guide 5 is more flexible and smaller in diameter than the chamber 4, the overtube 2 can be inserted into the body in a smooth manner. As shown in FIG. 10, the insertion stops at a position where the lateral hole 10 of the overtube 2 approaches a lesion W1 of an intestinal tract W. The lesion W1 is a treatment target portion that is to be resected entirely.

In the state in which the movement of the overtube 2 is stopped at such a position, the insertion portion 12 of the endoscope 7 is moved backward to confirm whether the lateral hole 10 is properly aligned with the lesion W1 by using the image pickup portion 13 of the endoscope 7. Then, the grasping forceps 15 (see FIG. 4) inserted through the treatment tool channel 14 is extended so as to allow the distal end to come out from the chamber 4 through the lateral hole 10, thereby grasping the lesion W1. Once the lesion W1 is grasped, the grasping forceps 15 is moved backward.

Figure 11:
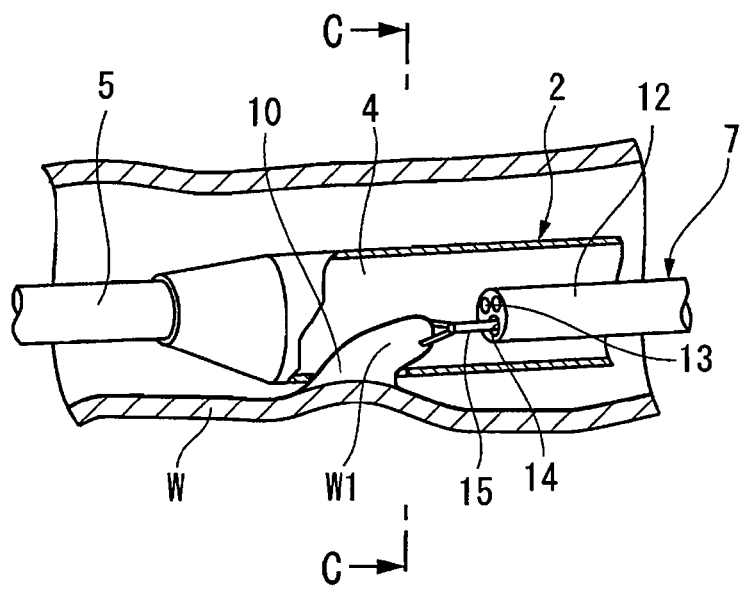
FIG. 11 is a diagram showing the state in which a lesion is drawn in from the lateral hole.
Figure 12:
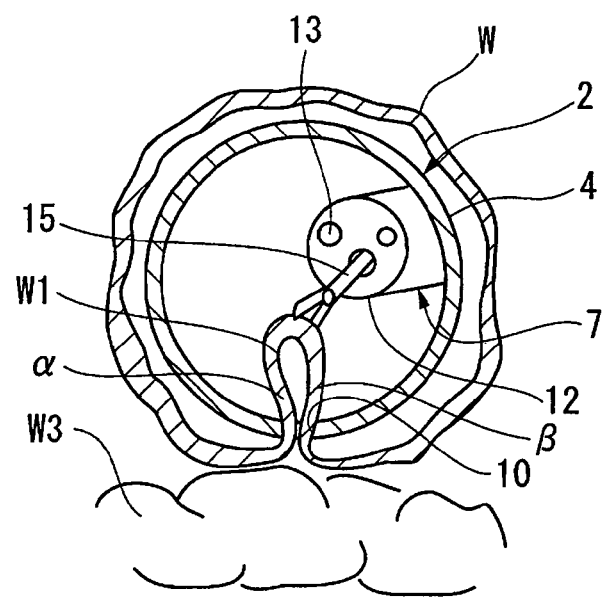
FIG. 12 is a sectional view taken along the line C-C in FIG. 11.

As shown in FIG. 11, the lesion W1 is drawn into the chamber 4 through the lateral hole 10 by being pulled by the grasping forceps 15. At this time, as shown in FIG. 12, the width of the lateral hole 10 is set small, and thus the width of the biological tissue that is drawn into the chamber 4 is restricted by the width of the lateral hole 10. Therefore, the lesion W1 and two biological tissues α and β on the outer circumference of the lesion W1 are drawn into the chamber 4 with the two biological tissues α and β overlapping with each other. In this case, other neighboring tissues or other neighboring biological tissues other than the treatment target portion, such as other internal organs W3 are pressed against the peripheral border of the lateral hole 10 and thus are not drawn into the chamber 4. Here, the biological tissues α and β are the treatment target portion that is to be sutured.

Figure 13:
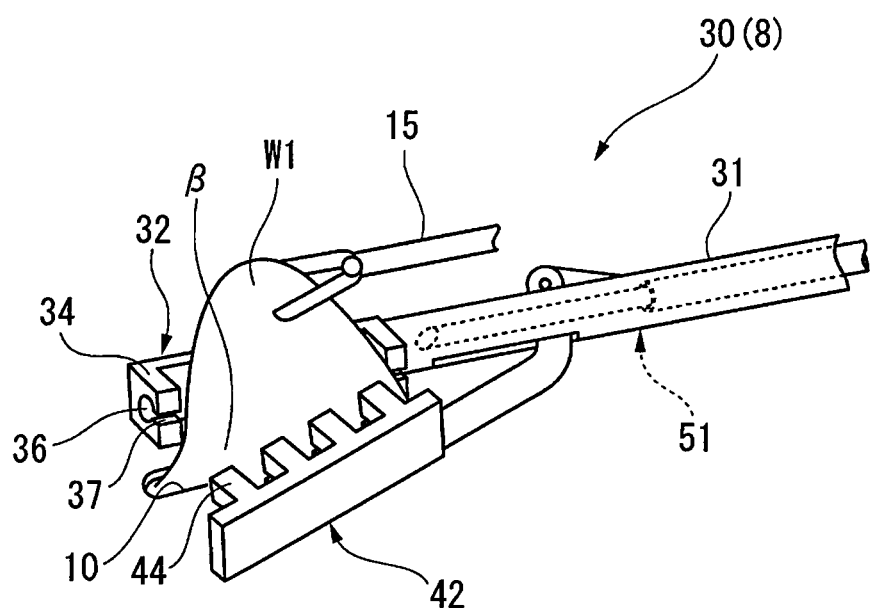
FIG. 13 is a diagram for explaining the operations of the suture unit.
Figure 14:
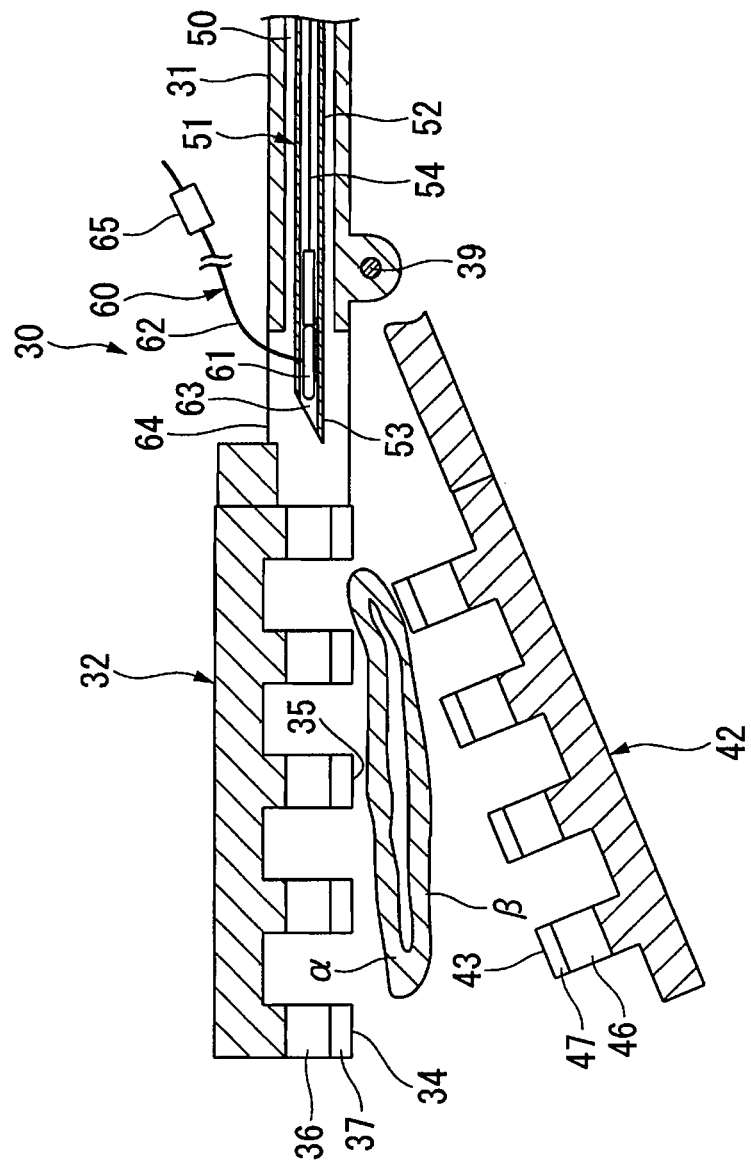
FIG. 14 is a sectional view of FIG. 13.

When the treatment target portion is drawn into the chamber 4, a suture treatment is performed on the biological tissues α and β with the suturing device 8. Specifically, as shown in FIGS. 13 and 14, the suture unit 30 is moved forward toward the lesion W1 in the state in which the first jaw 32 is opened with respect to the second jaw 42.

Figure 15:
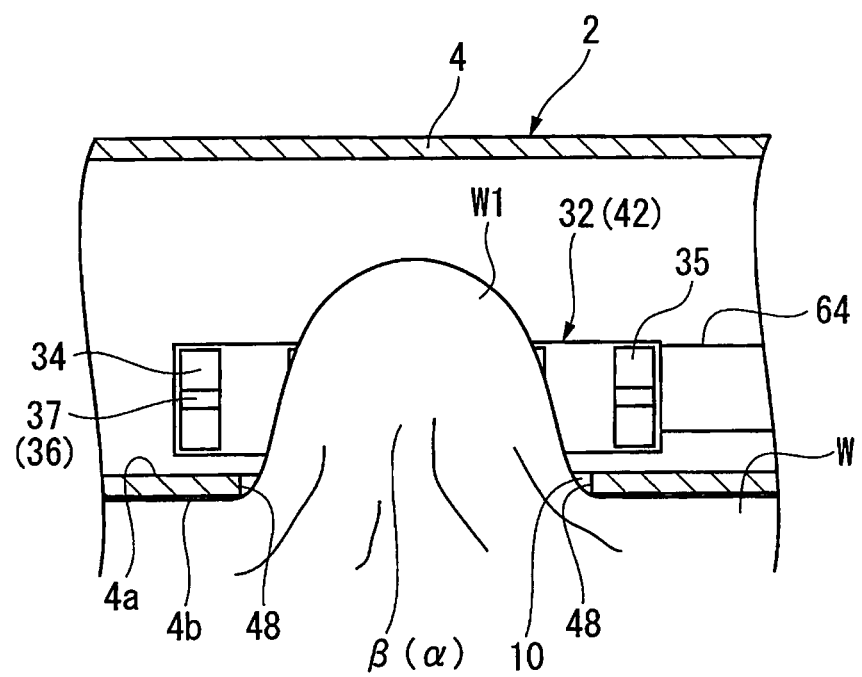

As shown in FIG. 8, the length between the tissue restricting portions 48, i.e., the longitudinal length Lb of the lateral hole 10 is smaller than the longitudinal length La of each of the jaws 32 and 42. Therefore, as shown in FIG. 15, the length of the biological tissues α and β is restricted by the tissue restricting portions 48 of the lateral hole 10 so as to be smaller than that of the jaws 32 and 42. As a result, the biological tissues α and β do not stick out from the distal or proximal end portion of the jaws 32 and 42.

Figure 16:
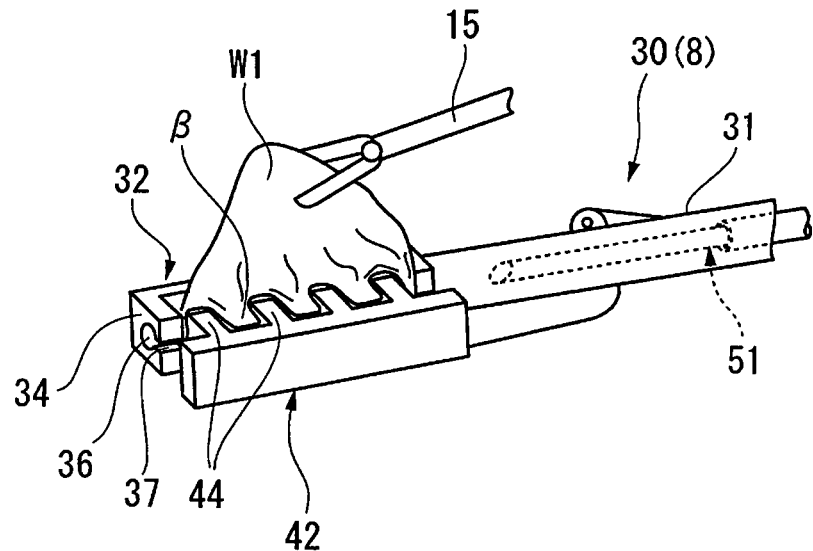
FIG. 16 is a diagram showing the state in which the biological tissue is sandwiched.

Therefore, when the slider 26 of the second operation portion 17 shown in FIG. 1 is moved backward, the second jaw 42 is closed to sandwich the biological tissues α and β between the first and second jaws 32 and 42 as shown in FIG. 16 without the biological tissues α and β sticking out from the jaws. The biological tissues α and β assume the shape of the crank-shaped gap between the first and second jaws 32 and 42 and are sandwiched between the corrugated surfaces, more specifically between the rectangular corrugated surfaces assuming the outer shapes of the teeth 34, 35, and 44.

Figure 17:
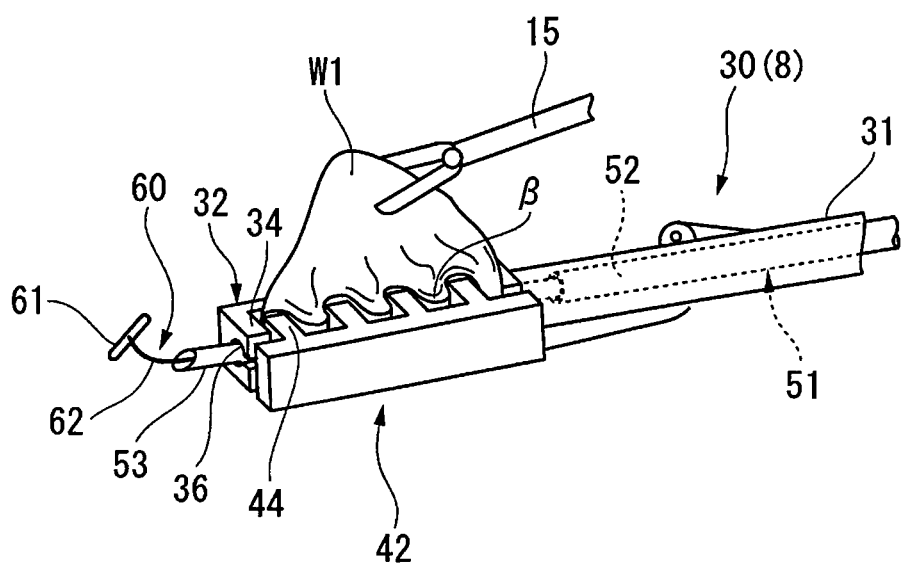
FIG. 17 is a diagram showing the state in which a tissue penetrating needle is thrust into the sandwiched biological tissue so as to extrude a T bar from the tissue penetrating needle.
Figure 18:
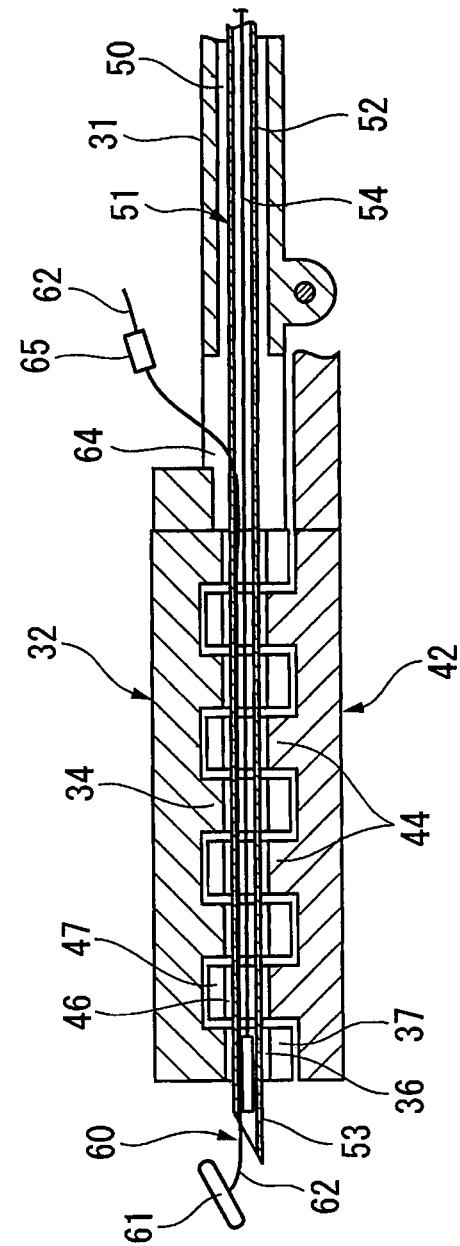
FIG. 18 is a sectional view of FIG. 17, showing the grasping unit

Then, the piston 19 of the first operation portion 16 shown in FIG. 1 is operated to move the tissue penetration needle 51 in the forward direction. The tissue penetration needle 51 penetrates the biological tissues α and β sandwiched between the teeth 34, 35, and 44 with the needle portion 53 pierced into the biological tissues α and β, and is sequentially passed through the through-holes 36 and 46 of the teeth 34, 35, and 44, finally coming out from the distal end. At this time, the T bar 61 received in the needle portion 53 also comes out through the biological tissues α and β, and therefore the suture thread 62 attached to the T bar 61 is passed through the biological tissues α and β and the first and second jaws 32 and 42. In this state, when the slider 20 of the first operation portion 16 is operated to move the pusher rod 54 in the forward direction, as shown in FIGS. 17 and 18, the T bar 61 is extruded from the needle portion 53.

Figure 19:
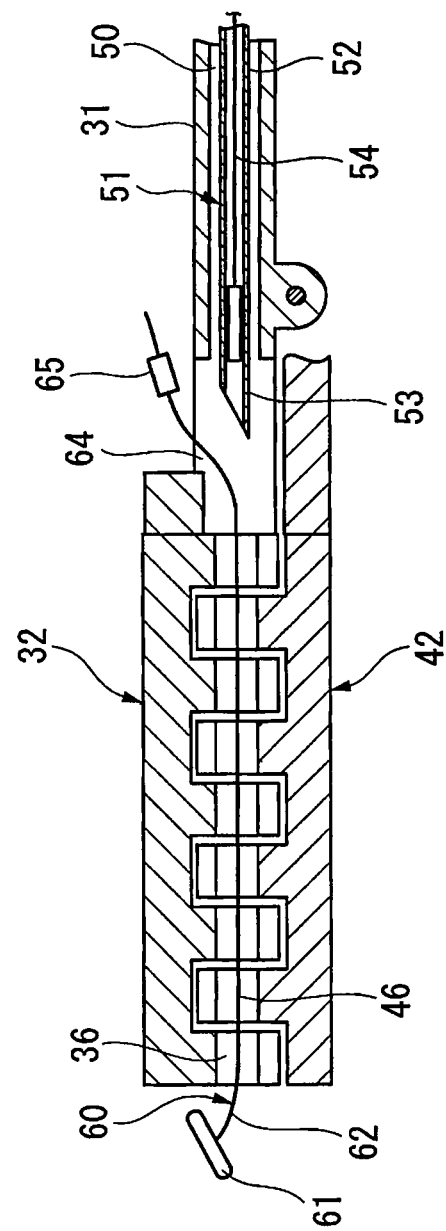
FIG. 19 is a sectional view of FIG. 18, showing the state in which the tissue penetrating needle is removed.

Then, as shown in FIG. 19, the piston 19 is operated to move the needle portion 53 in the backward direction. With this operation, the needle portion 53 is removed from the biological tissues α and β. However, because the T bar 61 extruded from the needle portion 53 is detained at a more distal side than the first and second jaws 32 and 42, the suture thread 62 maintains the state in which the suture thread 62 is passed through the biological tissues α and β.

Figure 20:
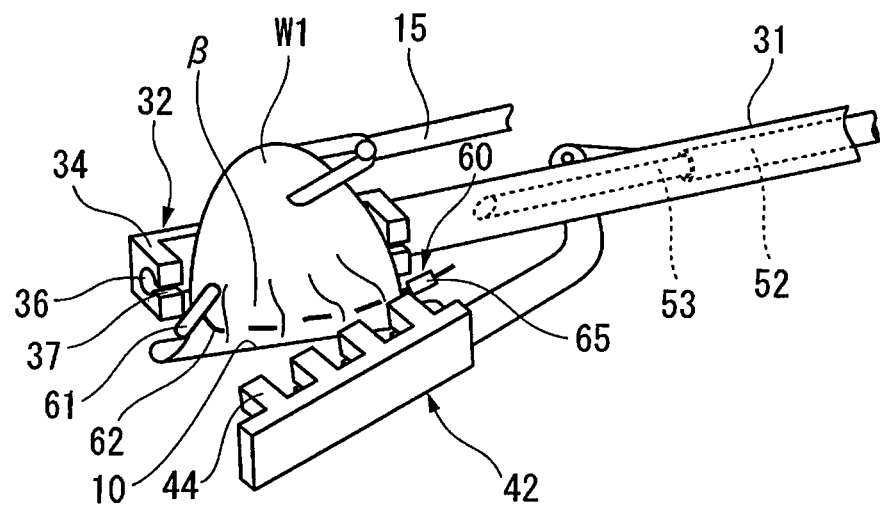
FIG. 20 is a diagram showing the state in which the grasping unit is opened after the biological tissue is sutured.
Figure 21:
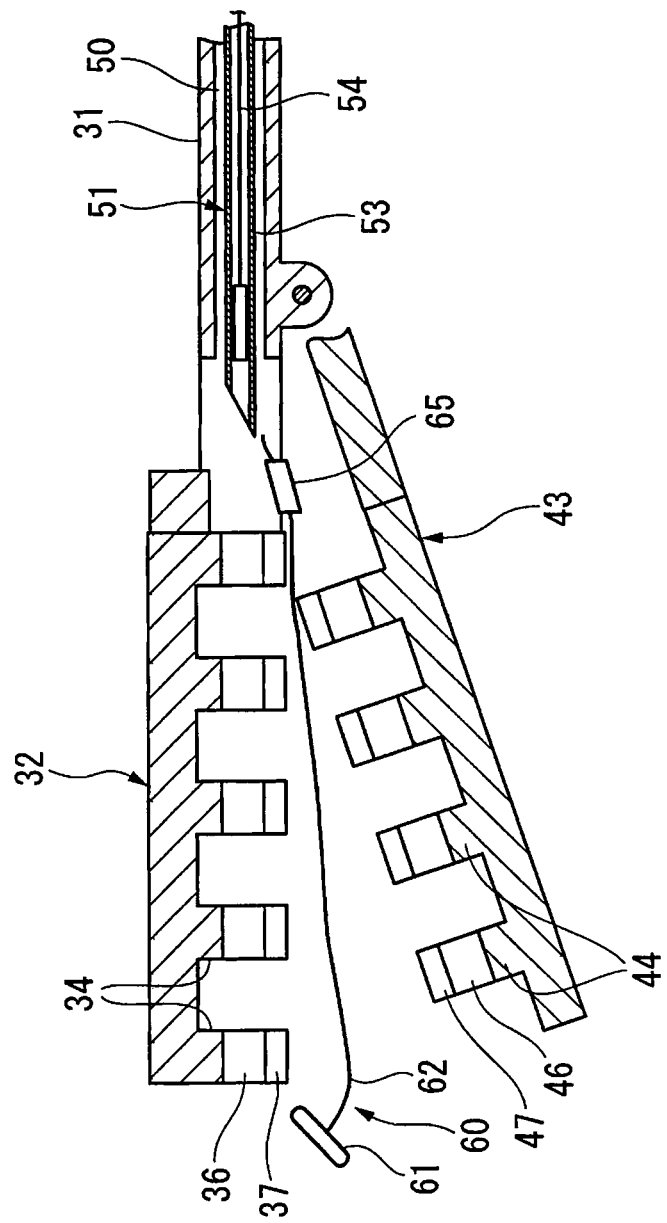
FIG. 21 is a sectional view of FIG. 20, showing the grasping unit.
Figure 22:
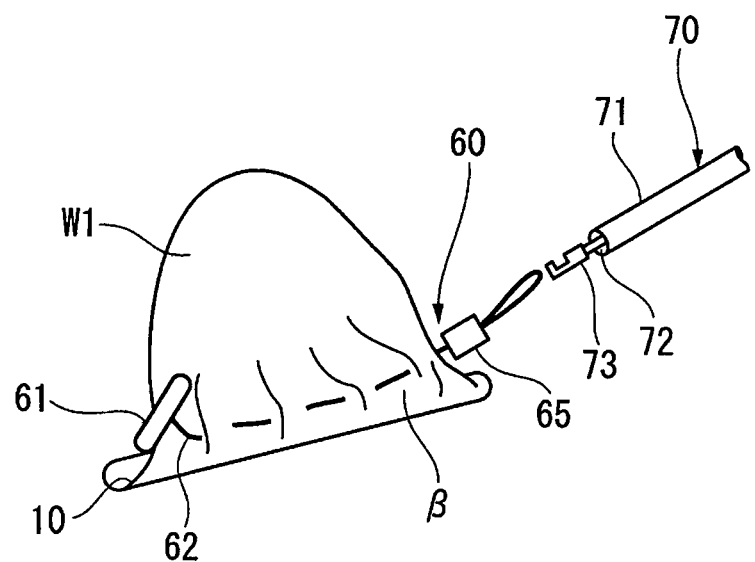
FIG. 22 is a diagram showing the state in which a suturing device is removed.

As shown in FIGS. 20 and 21, when the second jaw 42 is open, the suture thread 62 passes through the slits 37 and 47 and comes out from the first and second jaws 32 and 42, and the suturing tool 60 comes off the suture unit 30. In this state of the suturing tool 60, the suture thread 62 is passed through an approximately central portion of the corrugated biological tissues α and β, the T bar 61 is disposed at the distal end side of the biological tissues α and β, and the stopper 65 is disposed at the proximal end side of the biological tissues α and β. When the suture unit 30 is moved backward, as shown in FIG. 22, the biological tissues α and β can be fastened by a ligating tool 70 because the suturing tool 60 is detained at the state in which the suturing tool 60 is passed through the biological tissues α and β.

Figure 23:
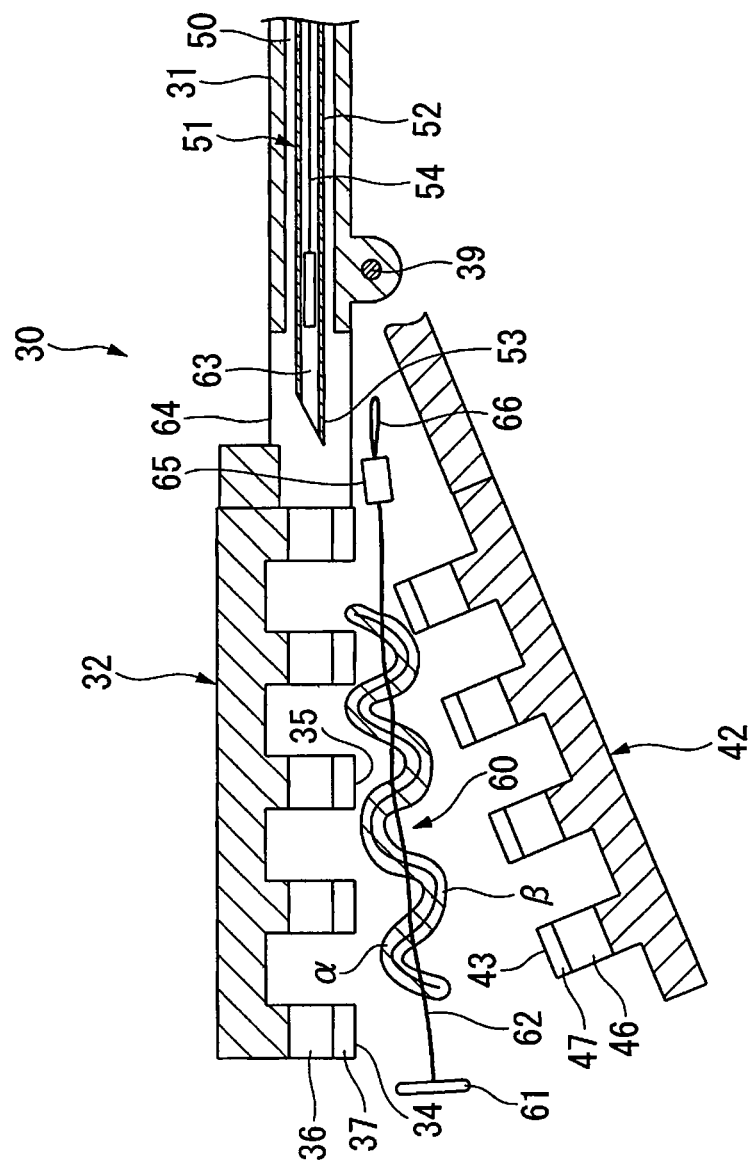
FIG. 23 is a diagram for explaining a ligature treatment of a ligating tool that ligates the biological tissue.
Figure 24:
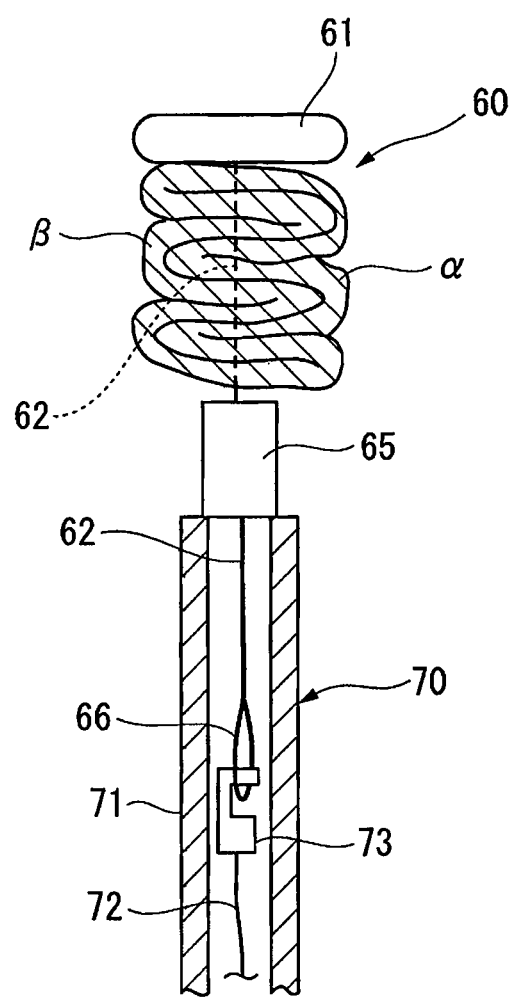
FIG. 24 is a diagram showing the state in which the ligating tool pulls a suture thread to fasten the biological tissue.

The ligating tool 70 is configured such that a wire 72 is inserted through an elongated sheath 71 so as to be freely moved forward and backward. At the distal end of the wire 72, a hook 73 serving as an engagement member is fixedly attached. Such a ligating tool 70 is used by being inserted through the treatment tool channel 14 of the endoscope 7. As shown in FIG. 23, the hook 73 as shown in FIG. 24 is moved closer to a proximal side loop 66 of the suture thread 62 passed through the biological tissues α and β. Once the hook 73 is hooked on the loop 66, an operator-side operation portion is operated to draw the hook 73 into the sheath 71.

Figure 25:
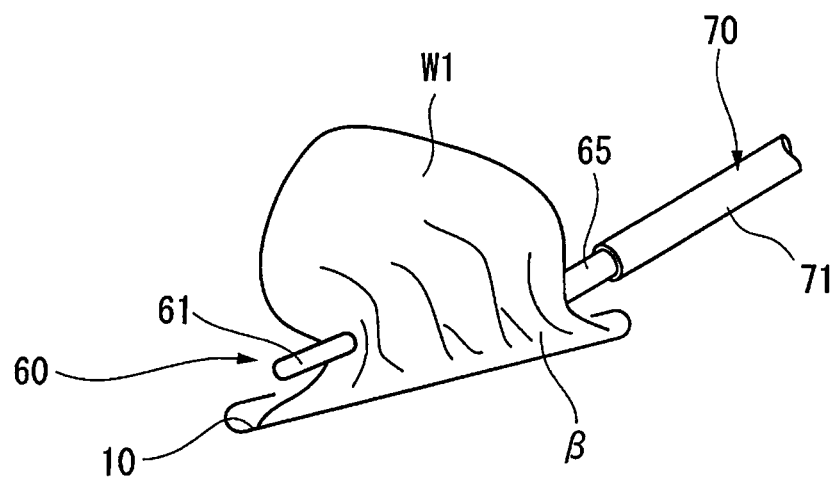
FIG. 25 is a perspective view of the state shown in FIG. 24.

As shown in FIGS. 24 and 25, the loop 66 engaged on the hook 73 is drawn into the sheath 71. However, the stopper 65 abuts the distal end surface of the sheath 71 and stops there because the size of the stopper 65 is greater than the outer diameter of the sheath 71. As a result, the stopper 65 is relatively extruded toward the biological tissues α and β, decreasing the distance between the T bar 61 and the stopper 65. Accordingly, the treatment target portion is fastened by the T bar 61 and the stopper 65 in such a manner that the walls of the corrugated biological tissues α and β are brought into close contact with each other in an overlapping manner.

Figure 26:
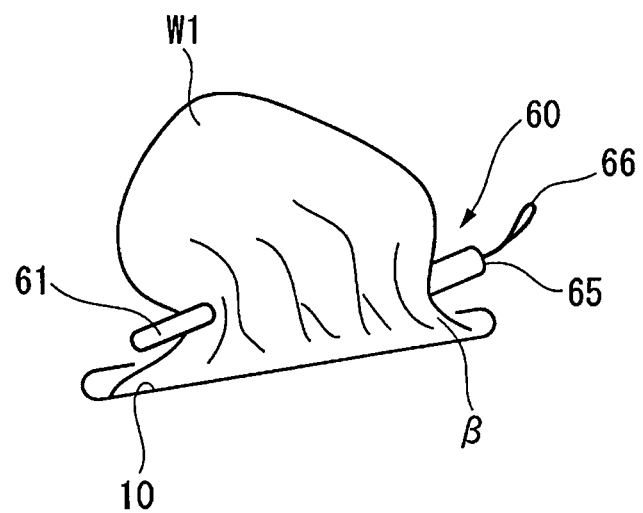
FIG. 26 is a diagram showing the state in which the ligating tool is removed.

Here, the T bar 61 has a size that does not pass through the biological tissues α and β, and the stopper 65 is press-fitted to the suture thread 62. Therefore, the fastening state of the biological tissues α and β is maintained when the force for drawing in the suture thread 62 is released. Accordingly, even after the engagement between the hook 73 and the suture thread 62 is released, the suture thread 62, the T bar 61, and the stopper 65 are detained in the body in the state in which the biological tissues α and β are securely sutured. In this way, as shown in FIG. 26, the biological tissues α and β are fastened by the suturing tool 60, and the surrounding portion of the lesion W1 is sutured. In addition, because the T bar 61 and the stopper 65 abut the pouch-shaped outer peripheral surfaces of the biological tissues α and β, the biological tissues α and β can be securely sutured without leaving out any portion of the biological tissues α and β.

Figure 27:
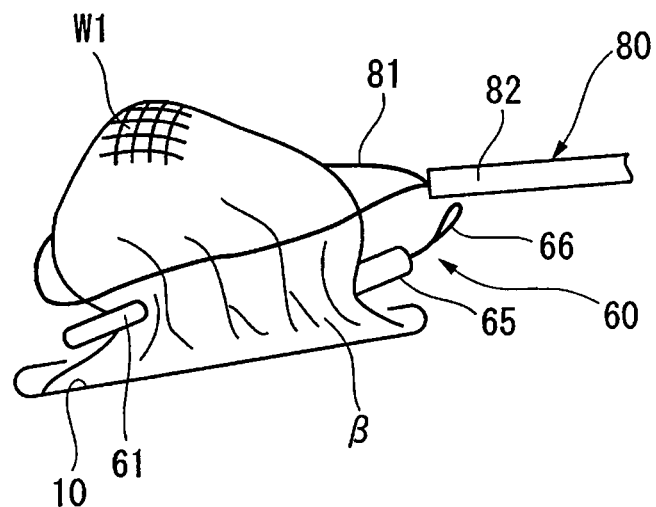
FIG. 27 is a diagram for explaining a procedure for resecting a lesion using a high-frequency snare.

Then, as shown in FIG. 27, a loop 81 of a high-frequency snare 80 is hooked on a portion closer to the lesion W1 than the sutured portion. Since the high-frequency snare 80 is used by being inserted into the treatment tool channel 14 of the endoscope 7, the loop 81 is formed of metal such as stainless steel and is adapted to freely come into and out of the elongated sheath 82.

Figure 28:
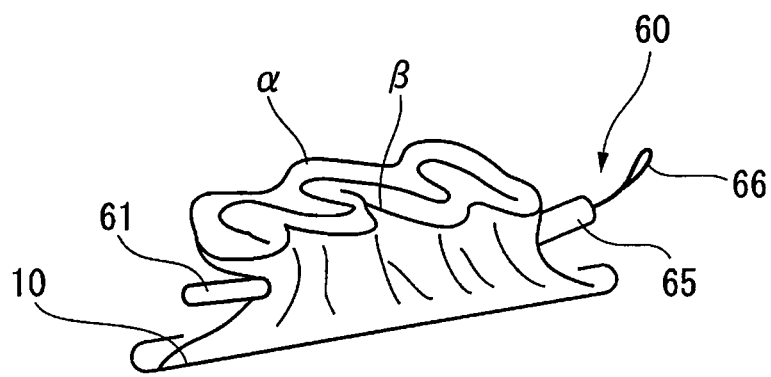
FIG. 28 is a diagram showing the state in which the lesion is resected.

By operating the operator-side operation portion, the loop 81 can be drawn into the sheath 82. In the state in which the surrounding portion of the lesion W1 is fastened, a high-frequency current is supplied to the loop 81, resecting the lesion W1. The resected lesion W1 is collected outside the body by the grasping forceps 15 or the like. As shown in FIG. 28, the biological tissues α and β 3 remaining after the entire lesion W1 is resected are left in the state that the biological tissues α and β are sutured by the suturing tool 60. In this way, since the tissues are sutured by fastening the tissues into a corrugated shape, perforations formed by the entire resection can be blocked in a secure manner, compared with the conventional suturing method that perforates a portion of a biological tissue.

According to the present embodiment, when resecting the entire lesion W1, the treatment target portion can be drawn into the chamber 4 in the state in which tissues around the treatment target portion are pressed against the chamber 4. In addition, the entanglement preventing portion is configured as the lateral hole 10 of the chamber 4 that has a small width corresponding to the size of the lesion W1. Therefore, only the minimal biological tissue required for the procedure can be drawn into the chamber 4. Thus, other biological tissues, particularly other organs W3 on the periphery of the intestinal tract W are not drawn into the chamber 4. Therefore, during the procedure, it is not necessary to confirm whether other organs W3 or the like are drawn into the chamber 4, simplifying the procedure and raising the efficiency of the procedure.

The chamber 4 is provided with the flexible and thin insertion guide 5 at its distal end, and the insertion guide 5 deforms so as to assume the shape of the insertion portion 12 of the endoscope 7 or of the internal body. Therefore, the overtube 2 can be easily inserted to an intended site. Since the tapered portion 6 is provided at the distal end of the chamber 4, even when the intestinal tract W is curved, the tapered portion 6 deforms while colliding against the tract wall to change the moving direction of the chamber 4 so as to assume the curved shape of the intestinal tract W. Accordingly, it is possible to insert the overtube 2 in an easier manner.

The suturing device 8 includes the grasping unit formed by the comb-teeth shaped, first and second jaws 32 and 42. In the suturing device 8, after grasping the two biological tissues α and β into a corrugated shape, more specifically into a rectangular corrugated shape, the suture thread 62 is passed through the biological tissues α and β using the tissue penetration needle 51, and then the biological tissues α and β are sutured while being sandwiched between the T bar 61 and the stopper 65. Therefore, the biological tissues α and β are joined with each other. Accordingly, perforations formed after the lesion W1 is resected are securely blocked, and the biological tissues α and β are immediately coalesced, thereby obstructing the perforations.

In the present embodiment, the vertex portions 34a, 35a, and 44a of the teeth 34, 35, and 44 of the first and second jaws 32 and 42 are formed of a flat surface, the biological tissues α and β sandwiched in a corrugated shape can be folded at an angle close to a right angle. Therefore, when fastened by the suture thread 62, the shape of the biological tissues α and β is not likely to change. In this way, in the present embodiment, operations up to the ligating operation can be performed in a trans-endoscopic manner.

When ligating the biological tissues α and β, the drawn-in length of the treatment target portion in the longitudinal direction of the jaws 32 and 42 is restricted by the tissue restricting portion 48. The portion to be sutured does not stick out from the distal or proximal end portion of the jaws 32 and 42. Therefore, the end portions of the biological tissues α and β are securely sutured without leaving out any portion of the biological tissues α and β. In this case, the overtube 2 functions as a tissue pressing member main body and a tissue restricting member.

Figure 29:
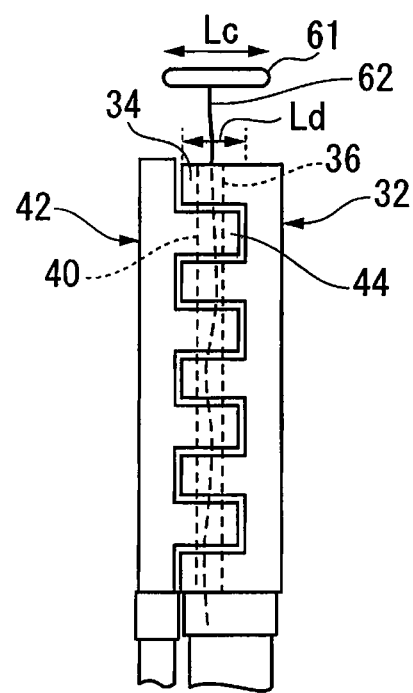
FIG. 29 is a diagram showing the sizes of the grasping unit and the T bar.

As shown in FIG. 29, the length Lc of the T bar 61 is preferably the same as or greater than the length Ld of the teeth 34, 35, and 44 of the first and second jaws 32 and 42. Since the T bar 61 is longer than the width of the overlapped, corrugated-shaped biological tissues α and β, the T bar 61 can press the entire width of the biological tissues α and β. Accordingly, the entire biological tissues α and β can be pressed in a secure manner.

Figure 30:
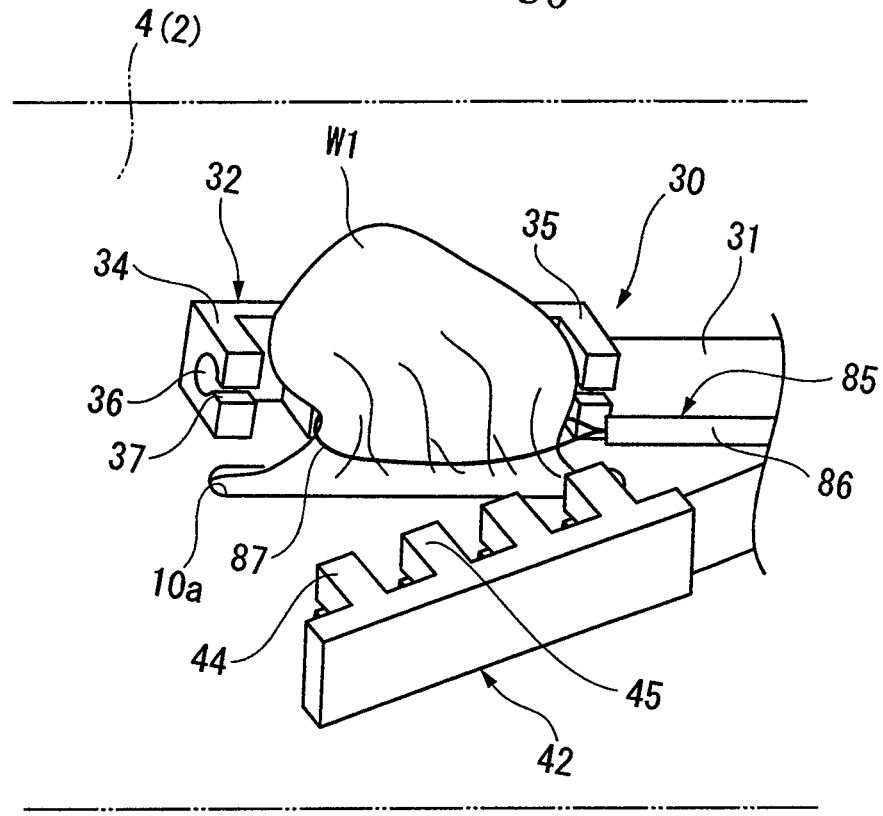
FIG. 30 is a diagram showing the state in which the biological tissue is sandwiched.

A snare 85 as shown in FIG. 30 may be provided as the tissue restricting member. The snare 85 is used by being inserted through the treatment tool channel 14 of the endoscope 7, and an annular snare portion (a tissue restricting portion) 87 can freely come into and out of a distal end portion of a long, flexible sheath 86. With the snare 85, the longitudinal length of the biological tissues α and β around the lesion W1 that are drawn into the lateral hole 10a of the chamber 4 is restricted so as not to exceed the longitudinal length (Lb in FIG. 8) of the jaws 32 and 42.

By adjusting the longitudinal position of the snare 85 by moving the snare 85 forward or backward in the longitudinal direction, it is possible to prevent the biological tissues α and β that need to be sutured from sticking out of the longitudinal ends of the jaws 32 and 42. In this case, it is not necessary to form the tissue restricting portion 48 (see FIG. 8) in the lateral hole 10a. The snare 85 may be inserted through the overtube 2 instead of inserting through the endoscope 7. Examples of the tissue restricting member include a treatment tool such as a grasping forceps that can restrict the length of the biological tissues α and β. Instead of the overtube 2, the endoscope 7 may be used as the tissue restricting member.

Figure 31:
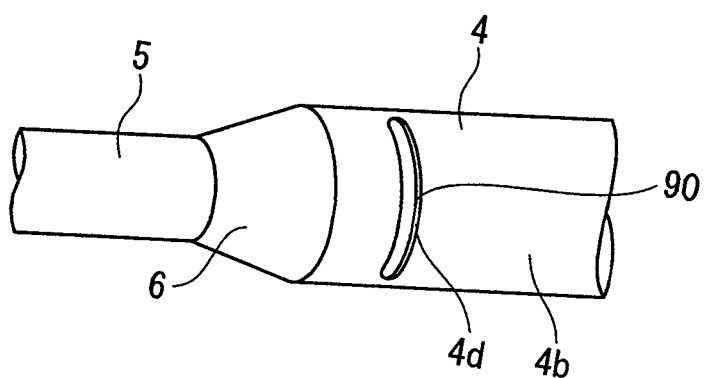
FIG. 31 is a diagram showing the shape of a lateral hole.
Figure 32:
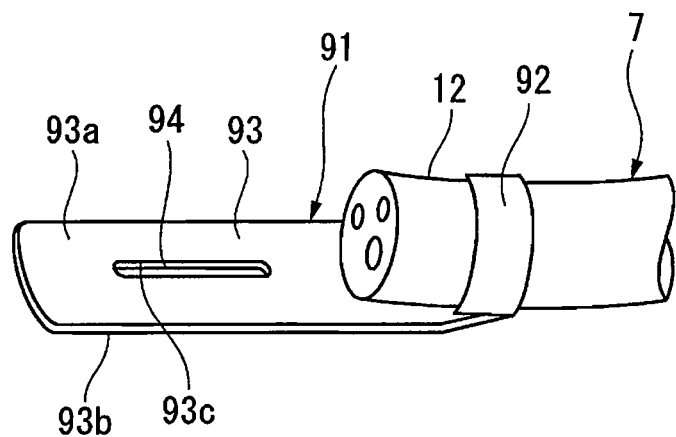
FIG. 32 is a diagram showing the shape of a pressing member.
Figure 33:
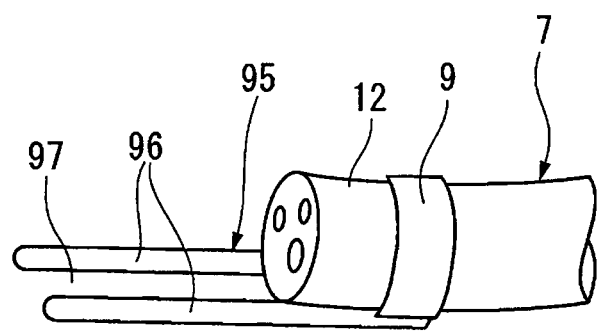
FIG. 33 is a diagram showing the shape of a pressing member.

The pressing member may have other shapes, for example, those shown in FIGS. 31 to 33 may be employed. As shown in FIG. 31, the chamber 4 may have, as the entanglement preventing portion, a hole 90 that is long in the circumferential direction of the chamber 4. The width of the lateral hole 90 in a direction perpendicular to the circumferential direction is approximately the same as the width of the lateral hole 10 shown in FIG. 2. In this case, the wall surfaces of the lateral hole 90 in the longitudinal direction of the chamber 4 correspond to a pressing portion 4d. Therefore, the treatment target portion can be drawn in a long and thin shape in a direction approximately perpendicular to the forward and backward movement directions of the grasping forceps 15. Accordingly, it becomes easy to draw in the treatment target portion with the grasping forceps 15. In such biological tissues that are resected and sutured, the sutured portion extends in a direction approximately perpendicular to the movement direction of food or like that flows along the intestinal tract W. Thus, the sutured biological tissues are not likely to cause stenosis.

As shown in FIG. 32, a pressing member 91 attached at the distal end of the endoscope 7 may be used. The pressing member 91 has a pressing member main body 93 that is mounted on the distal end portion of the insertion portion 12 of the endoscope 7 by an annular engagement portion 92. The pressing member main body 93 is formed of a plate-shaped member and protrudes out from the distal end of the endoscope 7 in a long and thin shape along the axial line of the insertion portion 12. In an approximately central portion of the pressing member main body 93, a lateral hole 94 serving as the entanglement preventing portion is formed in the longitudinal direction. The lateral hole 94 is penetrated through the pressing member main body 93, and the length and the opening width are the same as those of the lateral hole 10 shown in FIG. 2. In this case, the surface on the endoscope 7 side of the pressing member main body 93 corresponds to a first surface 93a, and an opposite surface of the first surface 93a corresponds to a second surface 93b.

In the lateral hole 94, the wall surfaces in a direction perpendicular to the longitudinal direction of the pressing member main body 93 correspond to a pressing portion 93c. In such a pressing member 91, neighboring tissues of the treatment target portion are pressed against the pressing member main body 93, and the entanglement of other organs W3 or the like is prevented by the lateral hole 94. The lateral hole 94 may be extended in a direction perpendicular to the longitudinal direction of the pressing member main body 93.

As shown in FIG. 33, a pressing member 95 may have a pair of arms 96 that extends in a direction parallel to the longitudinal direction of the insertion portion 12 of the endoscope 7. The arms 96 is a pressing member main body that is fixed to an annular engagement portion 92. Between the pair of arms 96, a space 97 serving as the entanglement preventing portion is defined. The width of the space 97 in a direction perpendicular to the longitudinal direction is substantially the same as the opening width of the lateral hole 10 shown in FIG. 2. In this case, the plane connecting the end portions of the pair of arms 96 on the endoscope 7 side corresponds to the first surface, and the plane connecting the end portions located farthest from the endoscope 7 corresponds to the second surface.

The portions opposed to the pair of arms 96 correspond to a pressing portion. In such a pressing member 95, neighboring tissues of the treatment target portion are pressed against the pair of arms 96, and the entanglement of other organs W3 or the like is prevented by the space 97.

The pressing member 91 or the pressing member 95 may be used as the tissue restricting member.

Embodiment 2

A second embodiment will be described with reference to FIGS. 34 to 39. Components similar or identical to those of the first embodiment will be referenced by the same reference numerals, and overlapping descriptions will be omitted.

Figure 34:
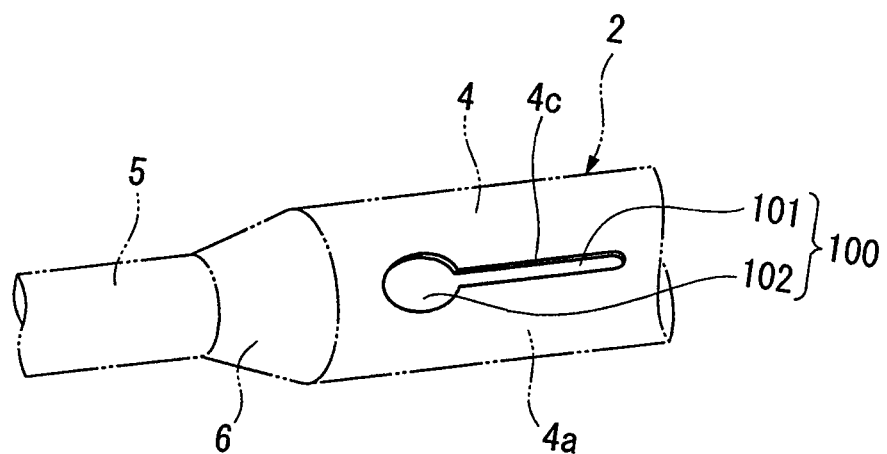
FIG. 34 is a diagram showing the shape of a lateral hole.

In the present embodiment, the shape of the lateral hole provided on the chamber is different from that of the first embodiment. That is, as shown in FIG. 34, a lateral hole 100 is an entanglement preventing portion that includes an elongated, first opening 101 and a second opening 102 that is provided to be connected to the distal end side of the first opening 101. The first opening 101 has the same length and width as that of the lateral hole 10 according to the first embodiment. The second opening 102 is formed in a substantially circular shape and has a width greater than that of the first opening 101.

Figure 35:
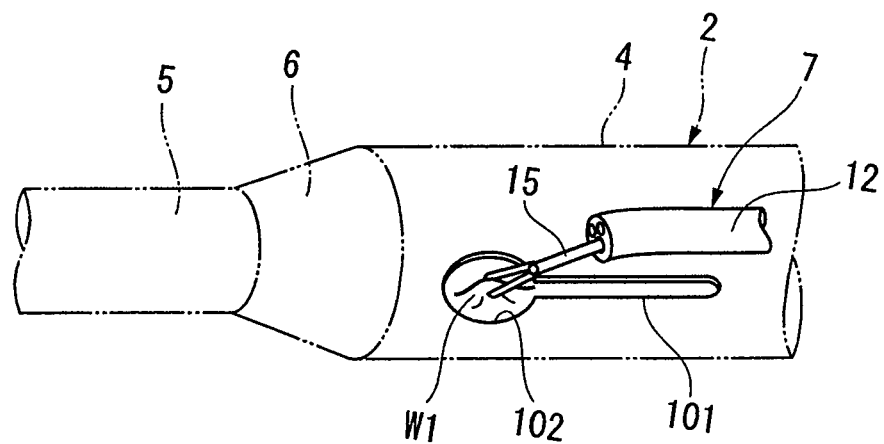
FIG. 35 is a diagram showing the state in which a lesion is grasped from a second opening.

As shown in FIG. 35, during the procedure, the overtube 2 is inserted with the second opening 102 opposed to the lesion W1, the grasping forceps 15 is extended to grasp the lesion W1 through the second opening 102. Then, the grasping forceps 15 is slightly pulled backward so that the distal end is received into the chamber 4. With this operation, the lesion W1 is slightly drawn into the chamber 4.

Figure 36:
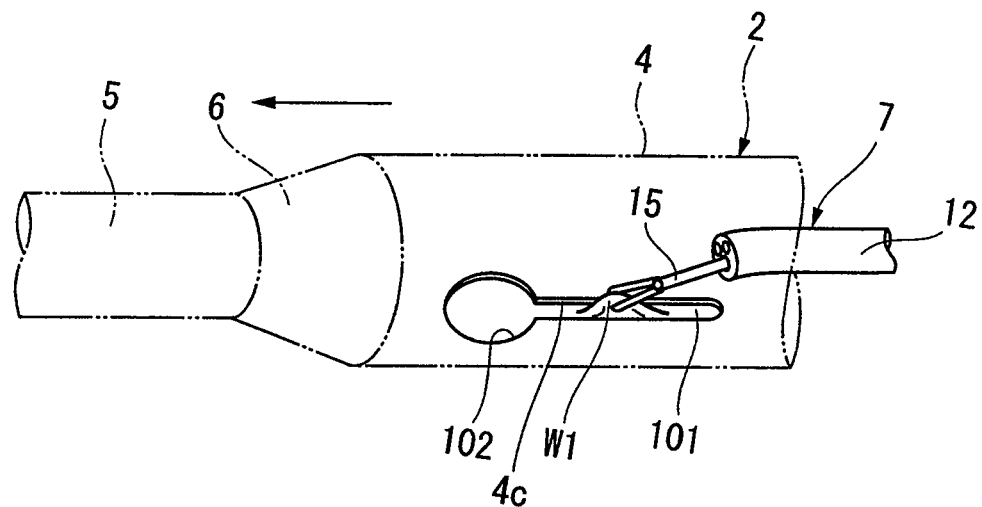
FIG. 36 is a diagram showing the state in which an overtube is relatively moved forward after the lesion is grasped.
Figure 37:
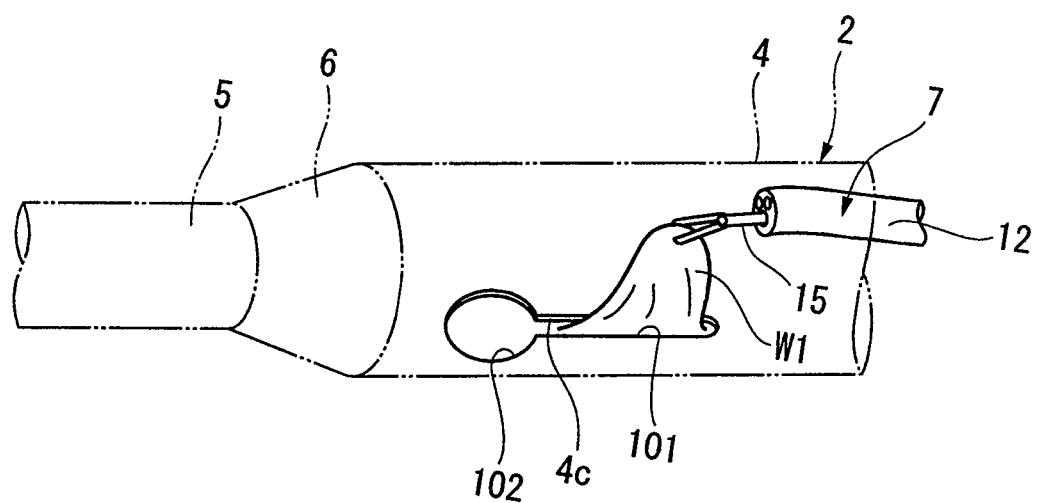
FIG. 37 is a diagram showing the state the lesion is drawn in through a first opening.

Then, as shown in FIG. 36, when the whole overtube 2 is moved forward with respect to the endoscope 7, the portion of the lesion W1 grasped by the grasping forceps 15 is received into the first opening 101. In this state, as shown in FIG. 37, when the grasping forceps 15 is pulled backward again, the lesion W1 is drawn into the chamber 4. At this time, the intestinal tract W on the periphery of the treatment target portion is pressed against the peripheral border of the first opening 101 so that only the treatment target portion is allowed to be drawn into the chamber 4 by the narrow, first opening 101 that prevents other organs W3 from being drawn into the chamber 4. After this, like the first embodiment, the treatment target portion is sutured by the suturing device 8, and the lesion W1 is cut with the high-frequency snare 80.

Figure 38:
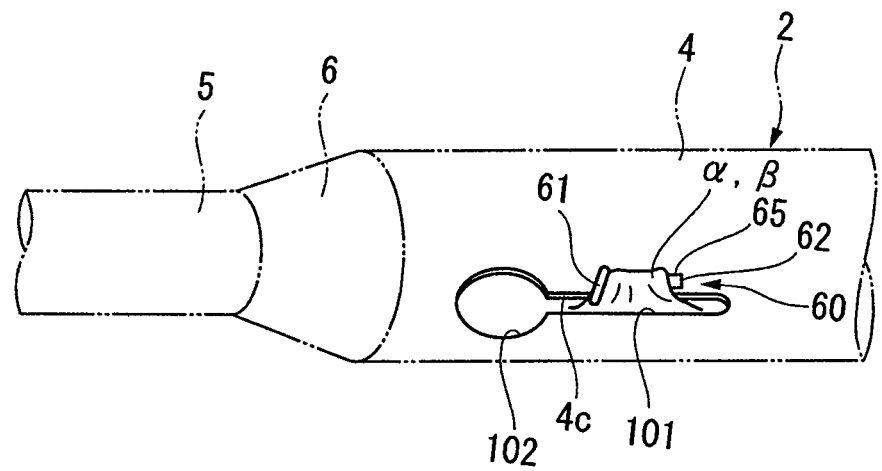
FIG. 38 is a diagram showing the state in which the lesion is resected.
Figure 39:
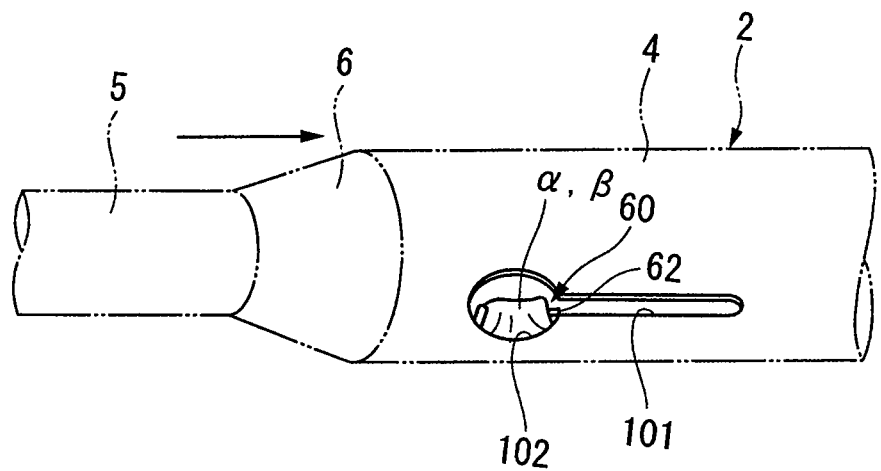
FIG. 39 is a diagram showing the state in which the sutured biological tissue is moved to a second opening.

As shown in FIG. 38, the biological tissues α and β drawn from the first opening 101 are sutured in a corrugated shape. Therefore, as shown in FIG. 39, when the whole overtube 2 is moved backward, the sutured biological tissues α and β are relatively moved backward toward the wide, second opening 102. As a result, the biological tissues α and β and the suturing tool 60 come out of the chamber 4 through the second opening 102.

In the present embodiment, since the entanglement preventing portion is formed by the first and second openings 101 and 102 having different opening widths, the lesion W1 can be grasped through the second opening 102 in an easy manner. In this case, since the suture treatment is performed when the lesion W1 is moved to the narrow, first opening 101, the suture treatment can be performed without causing other organs W3 or the like to be drawn in, and it is thus easy to confirm whether the entanglement of other organs W3 or the like occurs.

Since the sutured biological tissues α and β can be removed out of the chamber 4 through the wide, second opening 102, it is possible to pull the sutured portion out from the chamber 4 immediately along with the T bar 61 or the stopper 65 that has a large size. In addition, since the second opening 102 is first controlled to be opposed to the lesion W1, it is possible to widen the view field offered by the endoscope 7, making it easier to identify the position of the lesion W1.

Embodiment 3

A third embodiment will be described with reference to FIGS. 40 to 47. Components similar or identical to those of the afore-described embodiments will be referenced by the same reference numerals, and overlapping descriptions will be omitted.

Figure 40:
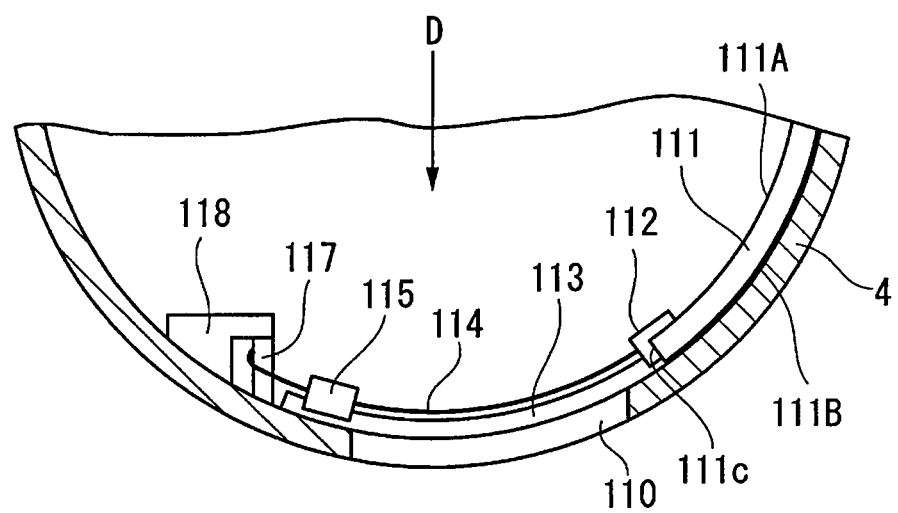
FIG. 40 is a sectional view taken along the direction perpendicular to the longitudinal direction of the lateral hole.

As shown in the sectional view of FIG. 40, a lateral hole 110 is formed in the chamber 4. The width of the lateral hole 110 in the circumferential direction of the chamber 4 is sufficiently larger than the thickness of the total layers of the lesion W1 to be drawn in. Here, on the inner circumference of the chamber 4, a slider cover 111 serving as the entanglement preventing portion is attached so as to be freely movable in the circumferential direction. The slider cover 111 includes a first surface 111A which is the inner circumferential surface opposed to the endoscope 7, and a second surface 111B which is the outer circumferential surface opposed to the treatment target portion. The slider cover 111 has a size that can cover the entire lateral hole 110 from the inside.

Figure 41:
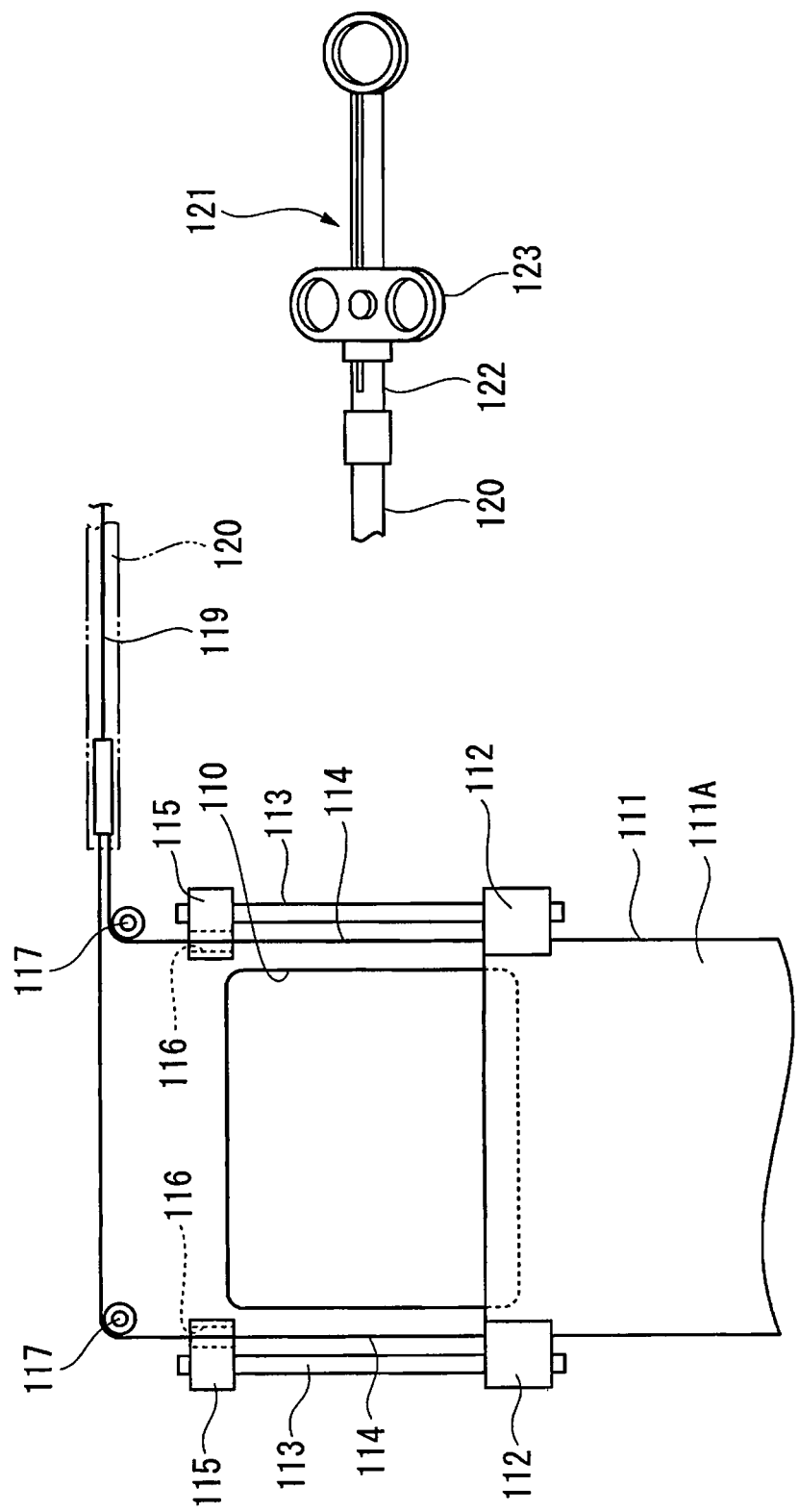
FIG. 41 is a view taken from the direction of the arrow D in FIG. 40.

As shown in FIG. 41, a pair of guides 112 is mounted on the end portions on the lateral hole 110 side of the slider cover 111. The guides 112 are slidably fitted to a pair of rails 113 that are laid between the distal and proximal end sides of the lateral holes 110 in a direction parallel to the circumferential direction.

The guides 112 are connected to wires 114. Each of the wires 114 is drawn along the pair of rails 113, then passed through a through-hole 116 of a wire guide 115, and is turned in the longitudinal direction of the chamber 4 while assuming the shape of the outer circumference of a pin 117. The pin 117 is fixed to the inner circumference of the chamber 4. As shown in FIG. 40, the distal end of the pin 117 is pressed against an L-shaped pressing member 118, preventing the wire 114 from dropping out from the pin 117.

As shown in FIG. 41, the end portions of the wire 114 are connected to the distal end portions of an operation wire 119. The operation wire 119 is inserted through a sheath 120 fixed to the inner wall of the overtube 2 so as to be freely moved forward or backward. The sheath 120 is connected to an operation portion main body 122 of an operator-side operation portion 121 that is drawn out of the body. The proximal end portion of the operation wire 119 is fixed to a slider 123 that can be freely moved forward or backward with respect to the operation portion main body 122.

Figure 42:
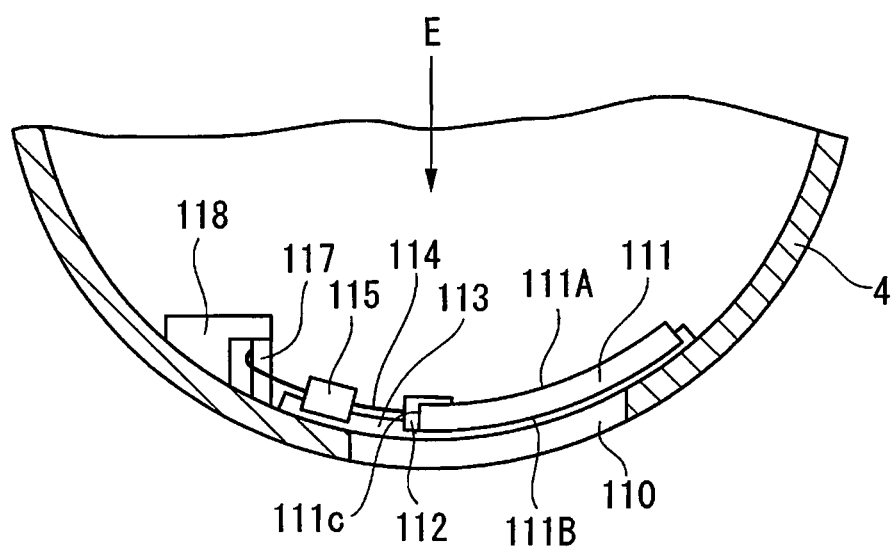
FIG. 42 is a sectional view of FIG. 40, in which a slider cover is closed.
Figure 43:
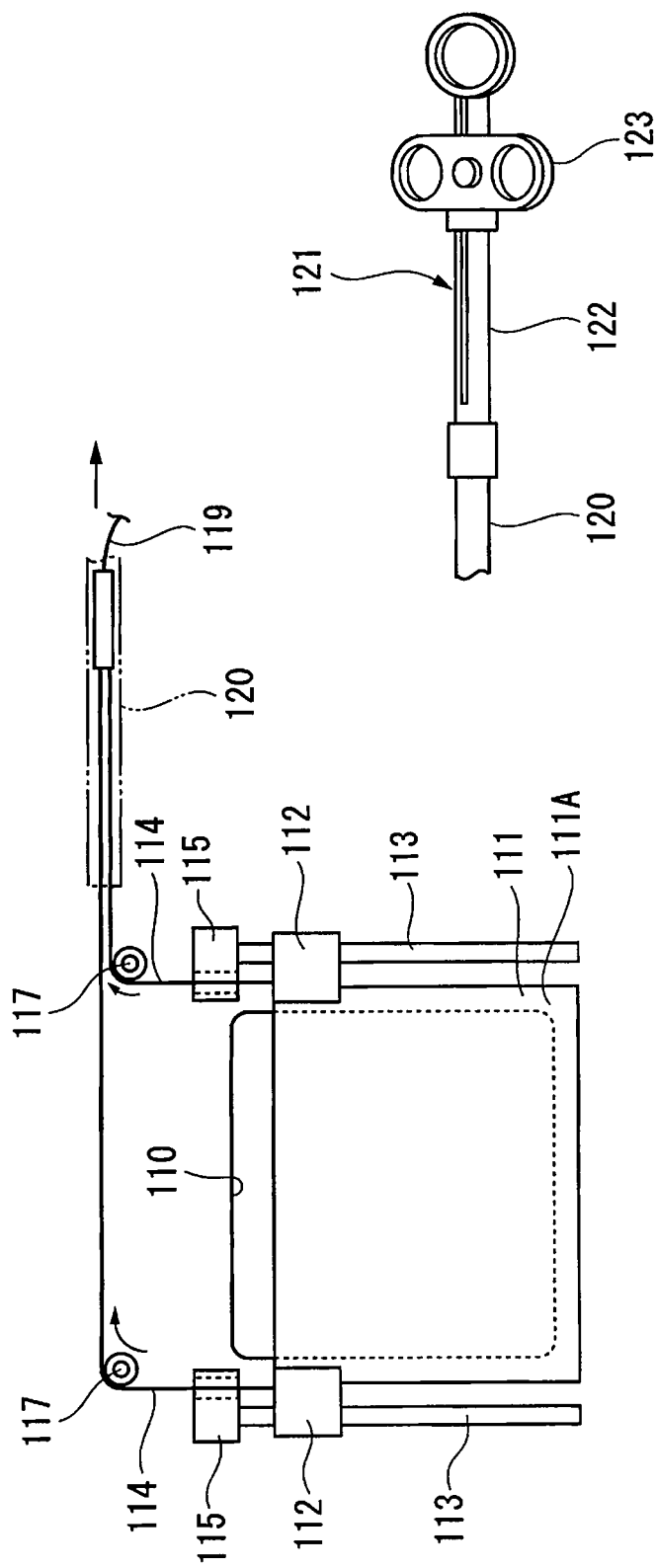
FIG. 43 is a view taken along the direction of the arrow E in FIG. 42.

That is, when the slider 123 is pulled toward the proximal end side, the slider cover 111 is moved with the operation wire 119 and the wire 114 so as to cover the lateral hole 110, the shown in FIGS. 42 and 43. Even when the slider 123 is pulled to the greatest extent, an opening width that allows the passage of the biological tissue required for the entire resection, for example, a gap of about 3 mm is defined by the lateral hole 110 and a pressing portion 111C that is formed of the lateral surface of the slider cover 111. A stopper (not shown) may be provided on the pair of rails 113 in order to provide the necessary opening width to the lateral hole 110.

Figure 44:
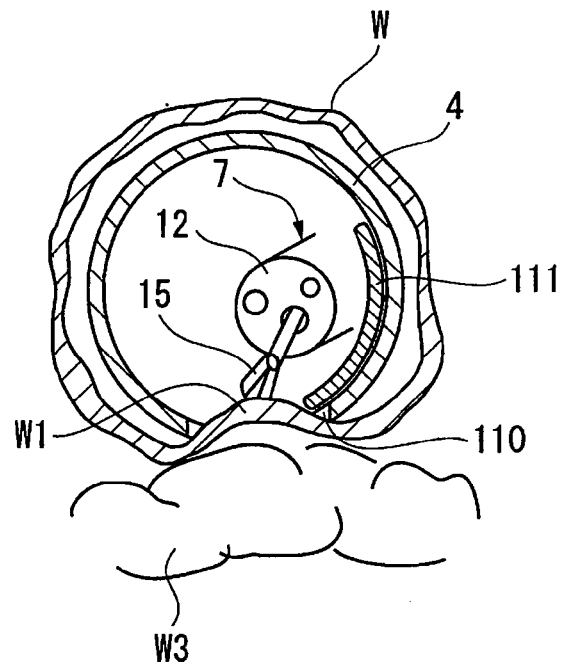
FIG. 44 is a diagram showing the state in which the lesion is grasped when the slider cover is open.
Figure 45:
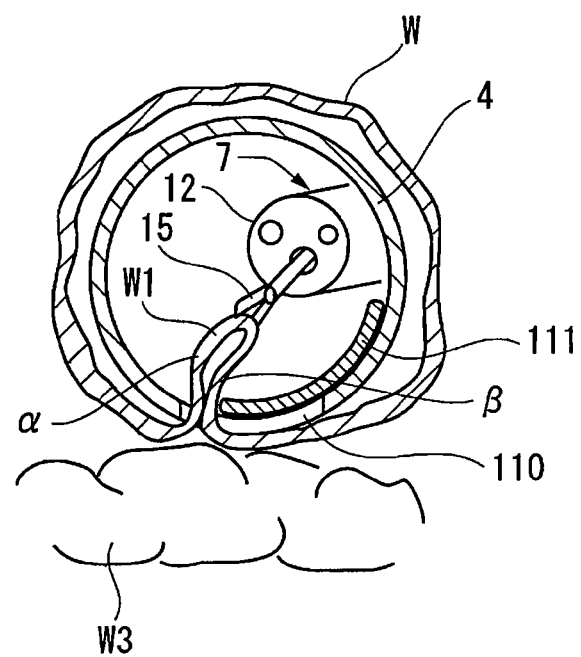
FIG. 45 is a diagram showing the state in which the lesion is drawn in after the slider cover is closed.

Next, operations of the present embodiment will be described. First, in a state that the slider cover 111 is open, the overtube 2 is inserted such that the lateral hole 110 is opposed to the lesion W1. As shown in FIG. 44, when an approximately central portion of the lesion W1 is grasped by the grasping forceps 15, the distal end of the grasping forceps 15 is pulled backward so as to be received into the chamber 4. After this, the operator-side operation portion 121 is operated to move the slider cover 111 to cover the lateral hole 110 while leaving a small gap. In this state, as shown in FIG. 45, when the grasping forceps 15 is pulled, neighboring tissues are pressed against the peripheral border of the lateral hole 110 and the second surface 111B of the slider cover 111.

The treatment target portion is drawn into the chamber 4 with the width restricted by the lateral hole 110 and the pressing portion 111C of the slider cover 111, preventing other organs W3 from being drawn into the chamber 4. Thereafter, the biological tissues α and β are sutured by the suturing device 8, and the entire lesion W1 is resected by the high-frequency snare 80. Then, the operator-side operation portion 121 is operated to move the slider cover 111 to uncover the lateral hole 110, and the sutured portion is removed out of the chamber 4.

In the present embodiment, in the initial state, the opening width is increased, making it easy to identify the position of the lesion W1 and to insert the grasping forceps 15. Before the lesion W1 is drawn into the chamber 4 for the suture treatment, the slider cover 111 is moved to decrease the opening width. The width of the biological tissue to be drawn into the chamber 4 is restricted by the opening width defined by the pressing portion 111C of the slider cover 111. Therefore, by setting the opening width to a size that allows the passage of only the treatment target portion, it is possible to prevent entanglement of other organs W3 or the like and to facilitate the procedure.

Other advantages of the present embodiment are the same as the first embodiment.

Figure 46:
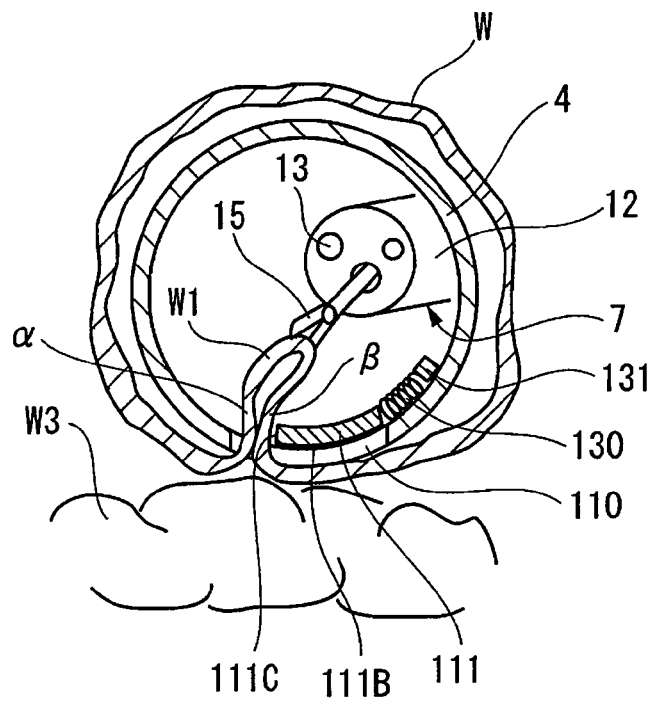
FIG. 46 is a sectional view showing another example of a mechanism that opens and closes the slider cover.
Figure 47:
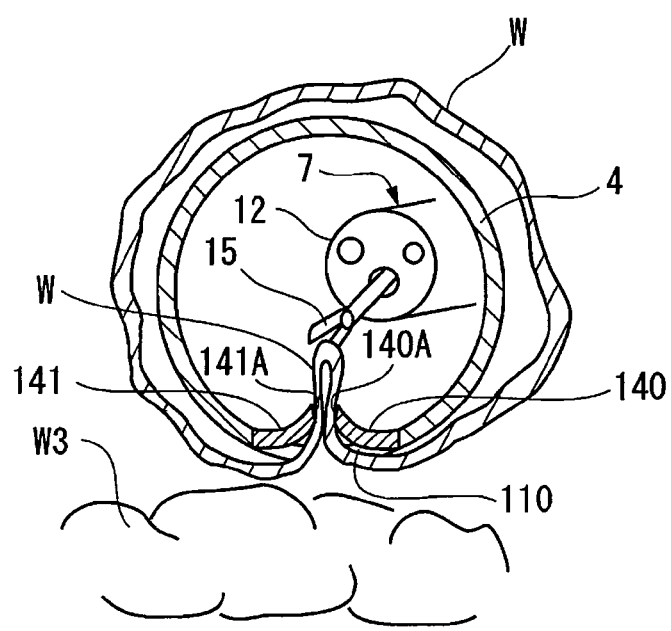
FIG. 47 is a sectional view of an entanglement preventing portion that is formed of an elastic member.

As other forms of the present embodiment, those shown in FIGS. 46 and 47 can be exemplified.

As shown in FIG. 46, the other end of the slider cover 111 is attached to one end of a coil spring 130. The other end of the coil spring 130 is fixedly attached to a protrusion 131 provided on the inner circumference of the chamber 4. The slider cover 111 is biased by the coil spring 130 so as to cover the lateral hole 110 while leaving a gap.

When resecting the entire lesion W1, the lesion W1 is drawn into the chamber 4 through the gap using the grasping forceps 15. At this time, the slider cover 111 is moved toward the protrusion 131 while resisting the force that moves the slider cover 111 toward the lesion W1. Accordingly, the treatment target portion is drawn into the chamber 4 with the drawn-in width corresponding to the increased opening width defined by the lateral hole 110 and the pressing portion 111C. Since the slider cover 111 is biased by the coil spring 130, the opening width is not unnecessarily increased, and thus other organs W3 or the like are not drawn into the chamber 4 through such a small opening width. Accordingly, other neighboring tissues other than the treatment target portion are pressed, preventing the entanglement of other organs W3.

As shown in FIG. 47, valve elements 140 and 141 serving as first and second entanglement preventing portions, respectively, made of an elastic member such as rubber are attached to the lateral hole 110 such that the opening width is decreased from the circumferential direction. The lateral portions of the valve elements 140 and 141 are fixed to the lateral borders of the lateral hole 110 by means of adhesive bonding or the like. The valve elements 140 and 141 are deformed about the lateral portions so as to be bent toward the inside, forming an elongated space that extends in the longitudinal direction between opposite ends 140A and 141A of the pair of valve elements 140 and 141.

These opposite ends 140A and 141A correspond to the pressing portion. The circumferential width of the space defined by the opposite ends 140A and 141A is substantially the same as the width of the lateral hole 10 shown in FIG. 2. When resecting the entire lesion W1, the treatment target portion is drawn into the chamber 4 through the space between the valve elements 140 and 141 using the grasping forceps 15. At this time, the valve elements 140 and 141 are deformed toward the inside while resisting the force that moves the valve elements toward the treatment target portion, increasing the distance between the opposite ends 140A and 141A so that the treatment target portion is drawn in with a width corresponding to the distance.

Since the distance between the opposite ends 140A and 141A is restricted by the restoring force of the valve elements 140 and 141, the opening width is not unnecessarily increased, and thus other organs W3 or the like are not drawn into the chamber 4 through such a small opening width. Accordingly, other neighboring tissues other than the treatment target portion are pressed, preventing the entanglement of other organs W3.

Embodiment 4

A fourth embodiment will be described with reference to FIGS. 48 to 57. Components similar or identical to those of the afore-described embodiments will be referenced by the same reference numerals, and overlapping descriptions will be omitted.

Figure 48:
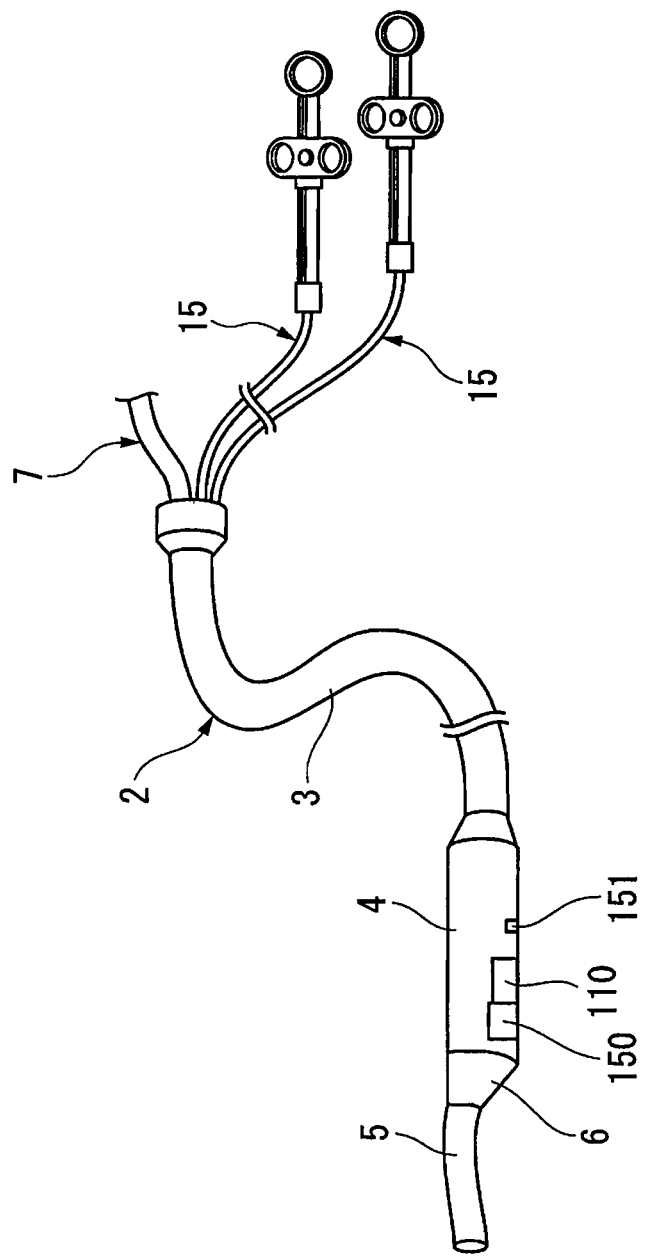
FIG. 48 is a diagram showing an overtube.

As shown in FIG. 48, the lateral hole 110 (a first opening) is formed in the chamber 4, and a slider cover 150 that can cover the lateral hole 110 is attached to the outer circumference of the chamber 4 so as to be freely moved forward or backward. The slider cover 150 is connected to the same mechanism as the slider cover 111 of the third embodiment and to an operator-side operation portion 121.

On a portion of the chamber 4 closer to the distal end than the formation position of the lateral hole 110, an opening (a second opening) 151 smaller than the lateral hole 110 is provided. The opening 151 has a size that allows the passage of the distal end portion of the grasping forceps 15 but does not allow the drawing in of the entire lesion W1.

Figure 49:
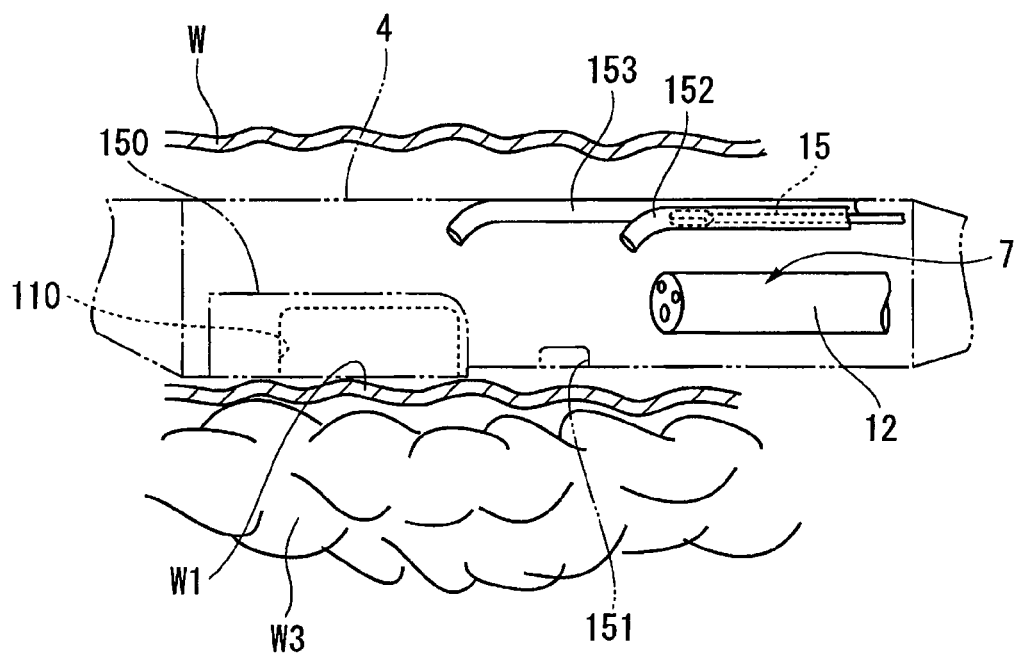
FIG. 49 is a diagram for explaining a procedure with the overtube shown in FIG. 48.

In the present embodiment, two grasping forceps 15 are inserted through a channel separately from that of the endoscope 7 and the suturing device 8. As shown in FIG. 49, the grasping forceps 15 is inserted through respective sheaths 152 and 153 that are fixed to the wall of the overtube 2 one by one. The sheath 152 has a distal opening that is tilted to be opposed to the opening 151. The sheath 153 has a distal opening that is tilted to be opposed to the lateral hole 110.

Next, operations of the present embodiment will be described. First, in the state that the lateral hole 110 is covered by the slider cover 150, the overtube 2 is inserted into the body. The reason the lateral hole 110 is covered is that by doing this, the insertion can be done in a smooth manner without being caught halfway. When the lateral hole 110 reaches the vicinity of the lesion W1, the endoscope 7 is pulled backward closer to the outside than the formation position of the opening 151, and the grasping forceps 15 inserted through the sheath 152 is extended so as to be inserted into the opening 151.

Figure 50:
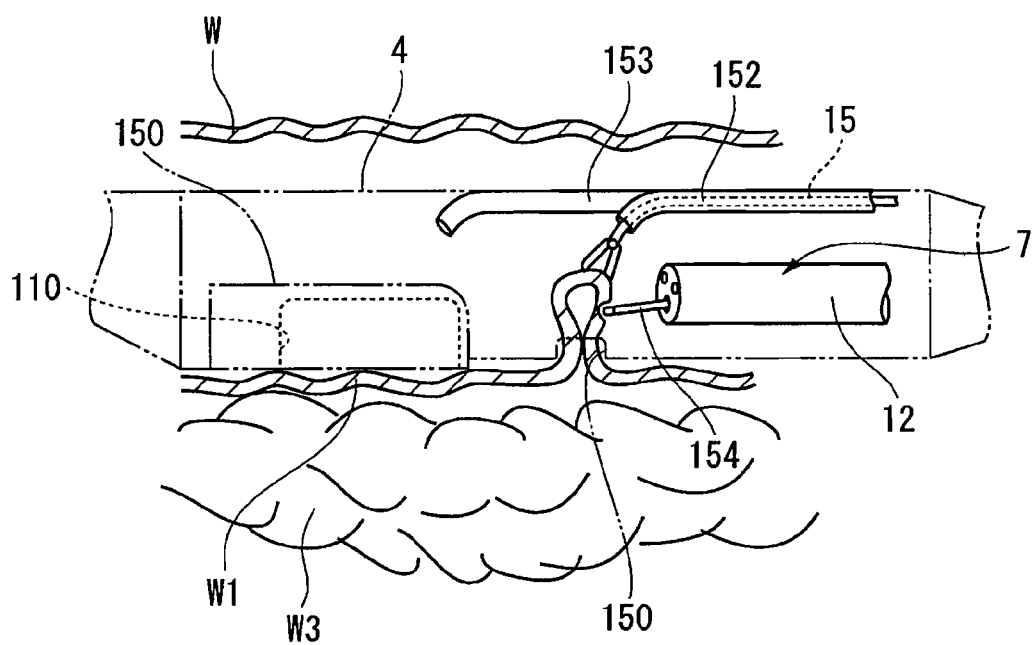
FIG. 50 is a diagram showing the state in which a perforation is punctured into a biological tissue in front of a lesion.

Then, a biological tissue at a small distance from the lesion W1 is grasped and is drawn into the chamber 4 through the opening 151. As shown in FIG. 50, a small perforation is formed in the biological tissue drawn into the chamber 4 using a high-frequency arm 154 inserted through the endoscope 7. Since the opening 151 has a small area, other organs W3 are not drawn into the chamber 4 through such a small opening.

Figure 51:
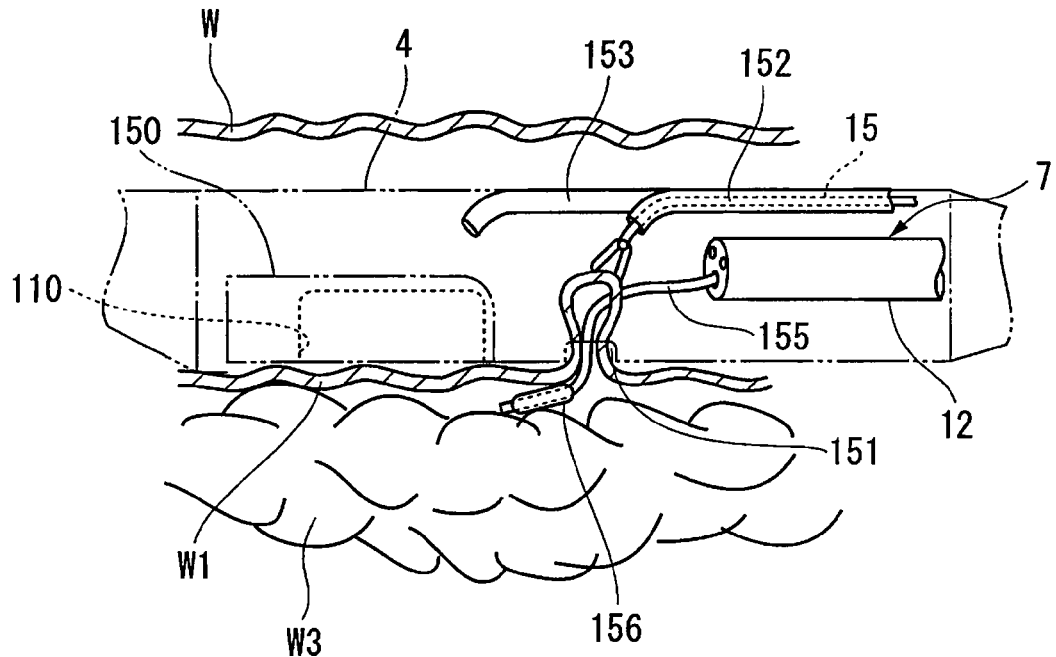
FIG. 51 is a diagram showing the state in which a balloon catheter is inserted into the perforation.
Figure 52:
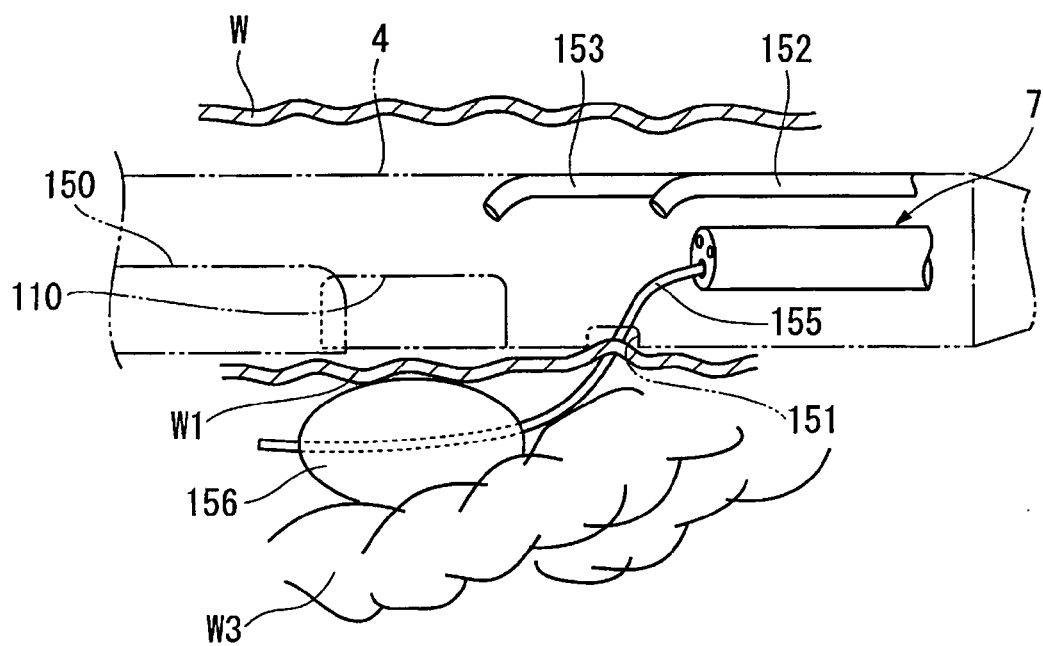
FIG. 52 is a diagram showing the state in which the balloon is inflated to displace other internal organs.

As shown in FIG. 51, a balloon catheter 155 serving as an entanglement preventing portion is inserted through the endoscope 7, and a balloon 156 serving as a displacing member provided at the distal end portion is delivered to the outside of the intestinal tract W through the perforation formed on the biological tissue. At this time, the position of the balloon 156 can be observed through X-ray irradiation, for example. When the balloon 156 is delivered to a position opposite the lateral hole 110 with the intestinal tract W interposed therebetween, as shown in FIG. 52, the slider cover 150 is moved to uncover the later hole 110, and air is blown into the balloon catheter 155 to expand the balloon 156.

Figure 53:
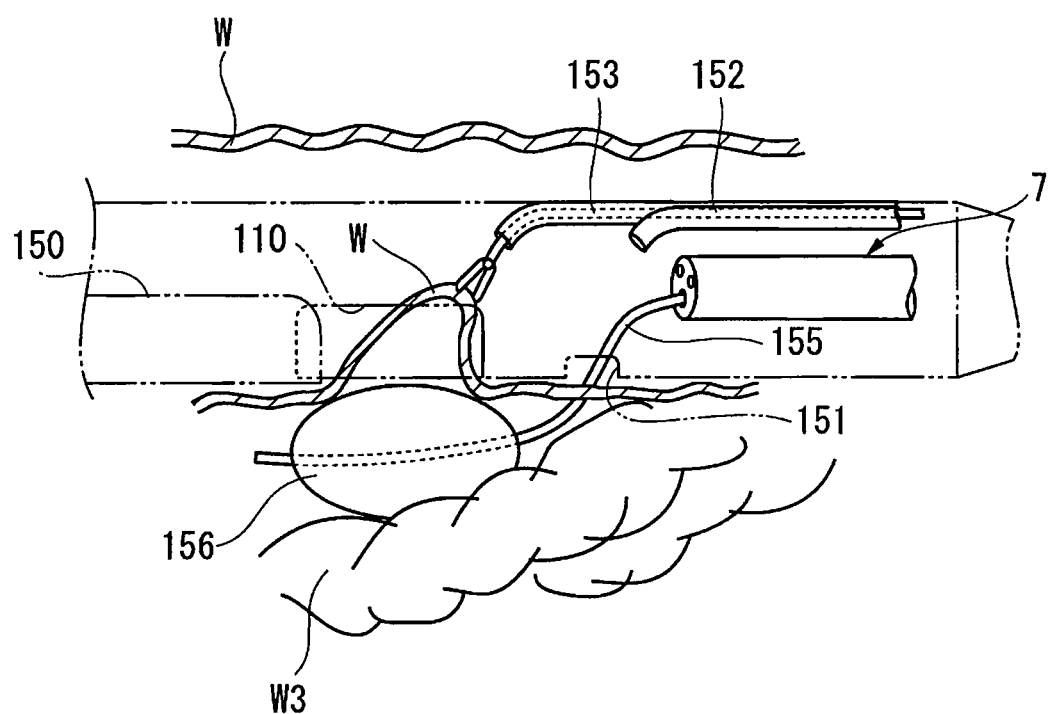
FIG. 53 is a diagram showing the state in which a lesion is drawn in while the balloon is inflated.

With this, in the formation position of the lateral hole 110, other organs W3 are isolated from the intestinal tract W by the balloon 156. Therefore, as shown in FIG. 53, when the lesion W1 is grasped by the grasping forceps 15 inserted through the sheath 153 and is drawn into the chamber 4, other organs W3 are not drawn into the chamber 4. The portions of the intestinal tract W that are not required for the entire resection are pressed against the peripheral border of the lateral hole 110 and thus are not drawn into the chamber 4.

In the present embodiment, the small opening 151 for inserting the balloon catheter 155 is provided on the operator side of the lateral hole 110 through which the lesion W1 is drawn in, and the balloon 156 is expanded after being inserted through the opening 151. It is possible to physically separate other organs W3 from the intestinal tract W and to thus prevent the entanglement of other organs W3 in a secure manner. Since other organs W3 can be securely separated, the lateral hole 110 can have a greater size and it is thus possible to draw in a larger amount of the treatment target portion.

Figure 54:
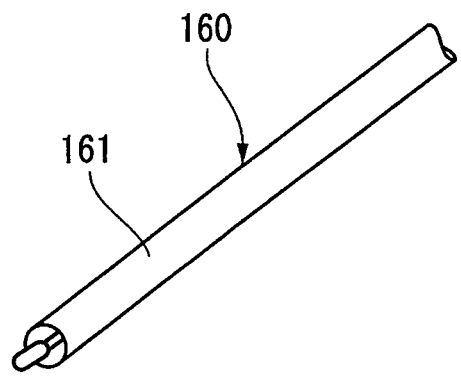
FIG. 54 is a perspective view of a distal end portion of a basket-type forceps in a closed state.
Figure 55:
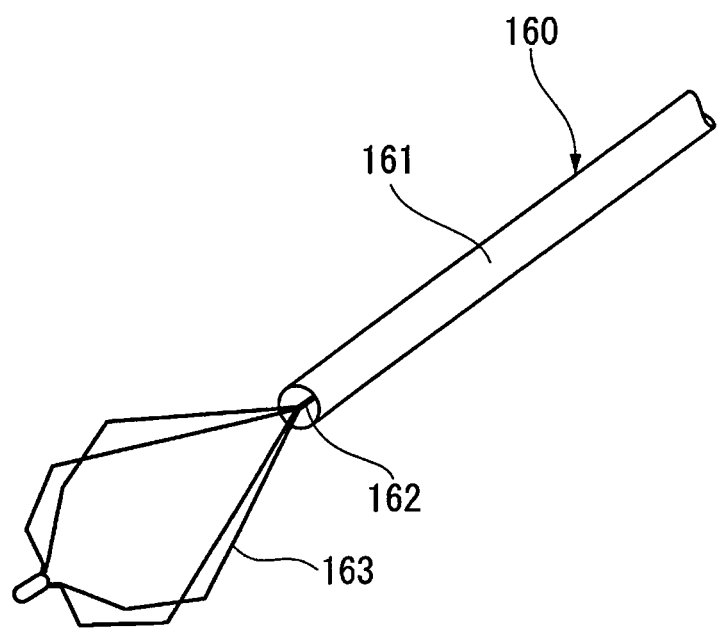
FIG. 55 is a perspective view of the distal end portion of the basket-type forceps in an unfolded state.

As the entanglement preventing portion for separating other organs W3 from the intestinal tract W, a basket-type forceps 160 as shown in FIGS. 54 and 55 can be used. The basket-type forceps 160 is configured such that an operation wire 162 is inserted through a long and flexible sheath 161 so as to be freely moved forward or backward. At the distal end of the operation wire 162, a basket 163 (a displacing member) formed of an elastically deformable wire is provided.

As shown in FIG. 52, in a state that the basket 163 is received in the sheath 161, the basket-type forceps 160 is inserted through the endoscope 7 and is then passed by the intestinal tract W, finally being delivered to a position opposite the lateral hole 110 with the lesion W1 interposed therebetween. After this, as shown in FIG. 55, the operation wire 162 is moved forward to unfold the basket 163, separating other organs W3 from the intestinal tract W.

Figure 56:
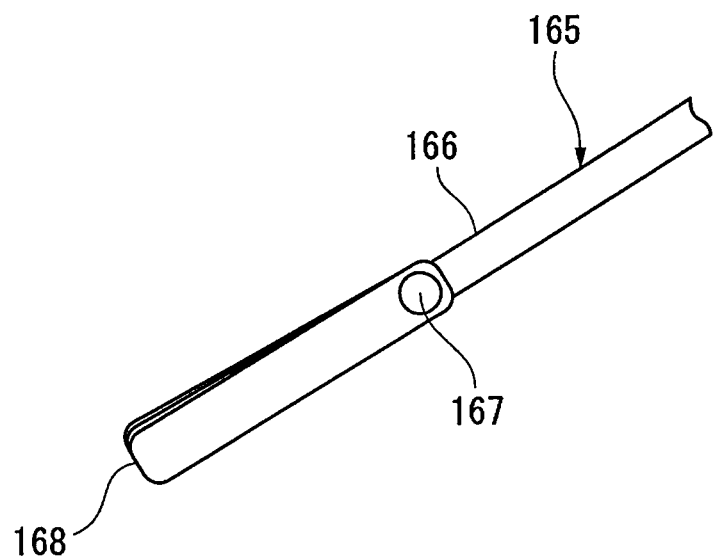
FIG. 56 is a perspective view of a distal end portion of the entanglement preventing portion in a closed state.
Figure 57:
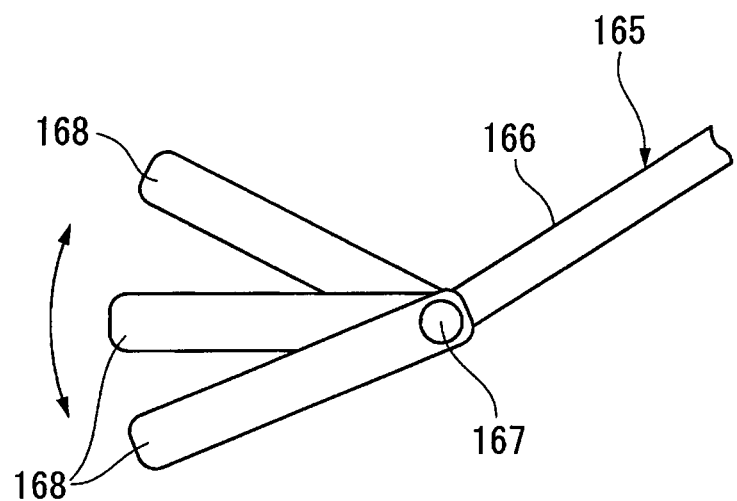
FIG. 57 is a perspective view of the entanglement preventing portion in an unfolded state.

Similarly, an entanglement preventing portion 165 as shown in FIGS. 56 and 57 may be used. The entanglement preventing portion 165 is configured such that a plurality of displacing members 168 is attached to the distal end of a long and flexible insertion portion 166 so that the displacing members 168 can freely pivot about a pin 167. Each of the displacing members 168 is formed of a plate-shaped member, and one longitudinal end thereof is supported on the pin 167.

The entanglement preventing portion 165 is inserted through the endoscope 7 and is then passed by the intestinal tract W, finally being delivered to a position opposite the lateral hole 110 with the lesion W1 interposed therebetween. As shown in FIG. 57, the displacing members 168 are unfolded in a fan-like shape while being pivoted about the pin 167. With this, the entanglement of other organs W3 is prevented. As the activating mechanism for the displacing members 168, a mechanism can be contemplated which biases the displacing members 168 to be unfolded in a normal state and folds the displacing members 168 when pulled by an operation wire (not shown).

Embodiment 5

A fifth embodiment will be described with reference to FIGS. 58 to 61. Components similar or identical to those of the afore-described embodiments will be referenced by the same reference numerals, and overlapping descriptions will be omitted.

Figure 58:
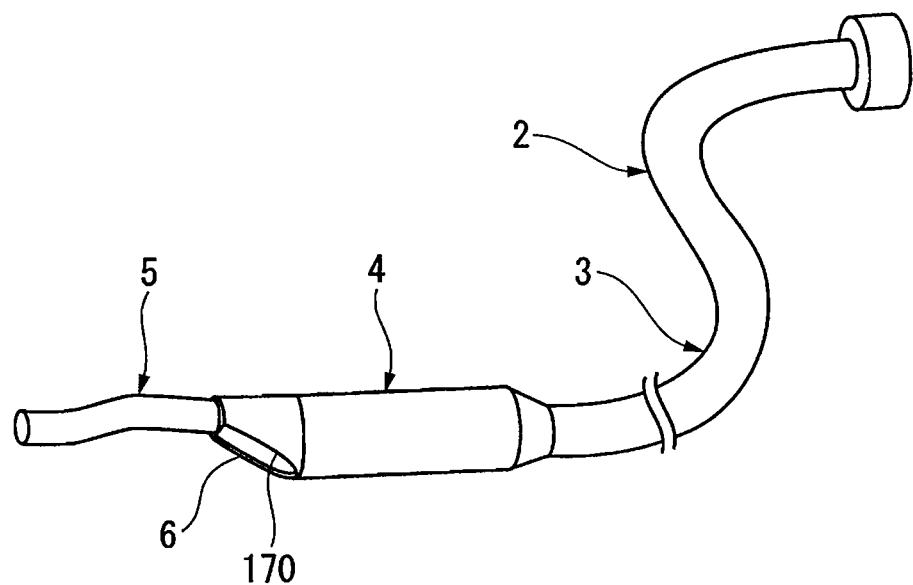
FIG. 58 is a diagram showing the structure of the overtube.

As shown in FIG. 58, the overtube 2 is provided with the chamber 4 at a distal end portion of the long and flexible tube main body 3. The small-diameter, flexible insertion guide 5 is provided on the distal end surface of the chamber 4. The chamber 4 has a higher hardness than the tube main body 3 and the insertion guide 5. A lateral hole 170 serving as an opening is formed in the tapered portion 6 that extends from the distal end surface while enlarging the diameter of the chamber 4.

Figure 59:
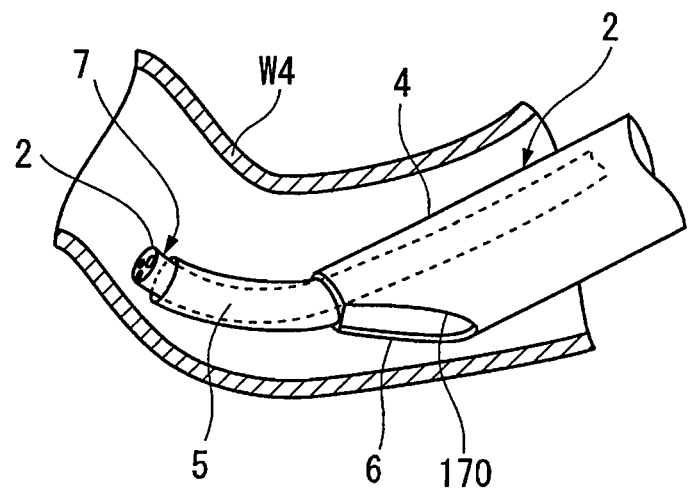
FIG. 59 is a diagram showing the state in which the distal end portion of the overtube is inserted.

As shown in FIG. 59, when the overtube 2 inserted into a curved alimentary tract W4, the insertion guide 5 can be deformed along with the insertion portion 12 of the endoscope 7 while assuming the shape of the alimentary tract W4. Accordingly, it is easy to allow the overtube 2 to follow the way the endoscope 7 moves.

Figure 60:
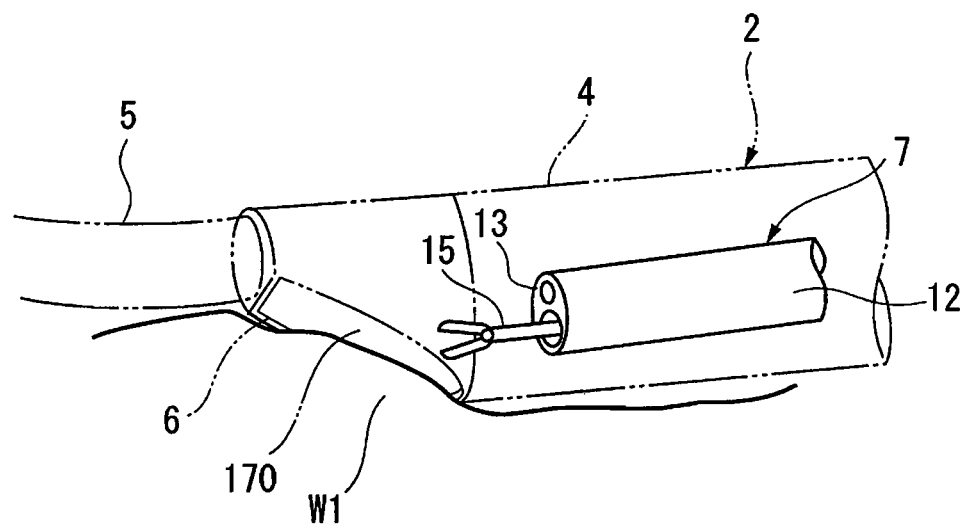
FIG. 60 is a diagram showing the state in which the overtube is inserted so as to approach a treatment target portion.
Figure 61:
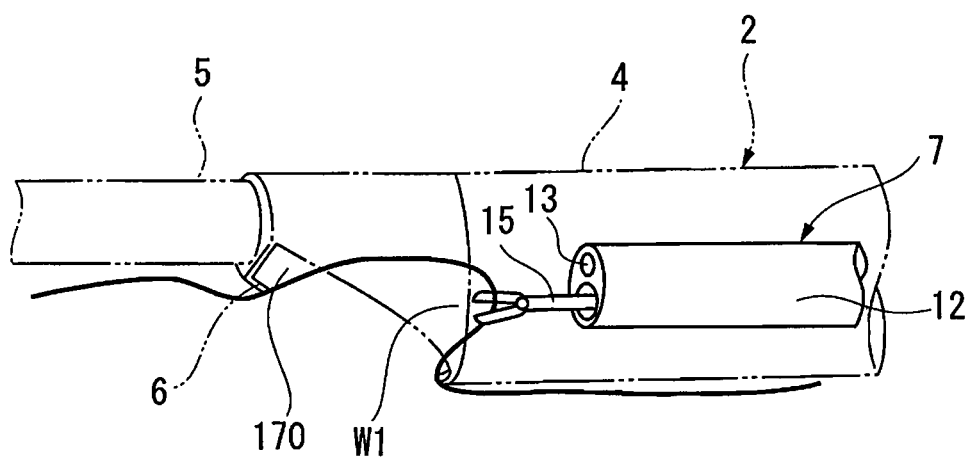
FIG. 61 is a diagram showing the state in which the treatment target portion is drawn into a chamber.

As shown in FIG. 60, in the overtube 2, the lesion W1 is drawn into the lateral hole 170. Since the lateral hole 170 is tilted with respect to the insertion direction, the endoscope 7 can directly approach the lesion W1. Therefore, as shown in FIG. 61, the lesion W1 can be grasped by the grasping forceps 15 almost without bending the grasping forceps 15 and can be drawn into the chamber 4. In the present embodiment, since the lateral hole 170 is provided in the tapered portion 6, it is possible to observe the lesion W1 without bending the distal end portion of the endoscope 7 and to thus facilitate the procedure. Also, the grasping forceps 15 can be operated in a simple manner.

Embodiment 6

A sixth embodiment will be described with reference to FIGS. 62 to 67. Components similar or identical to those of the afore-described embodiments will be referenced by the same reference numerals, and overlapping descriptions will be omitted.

Figure 62:
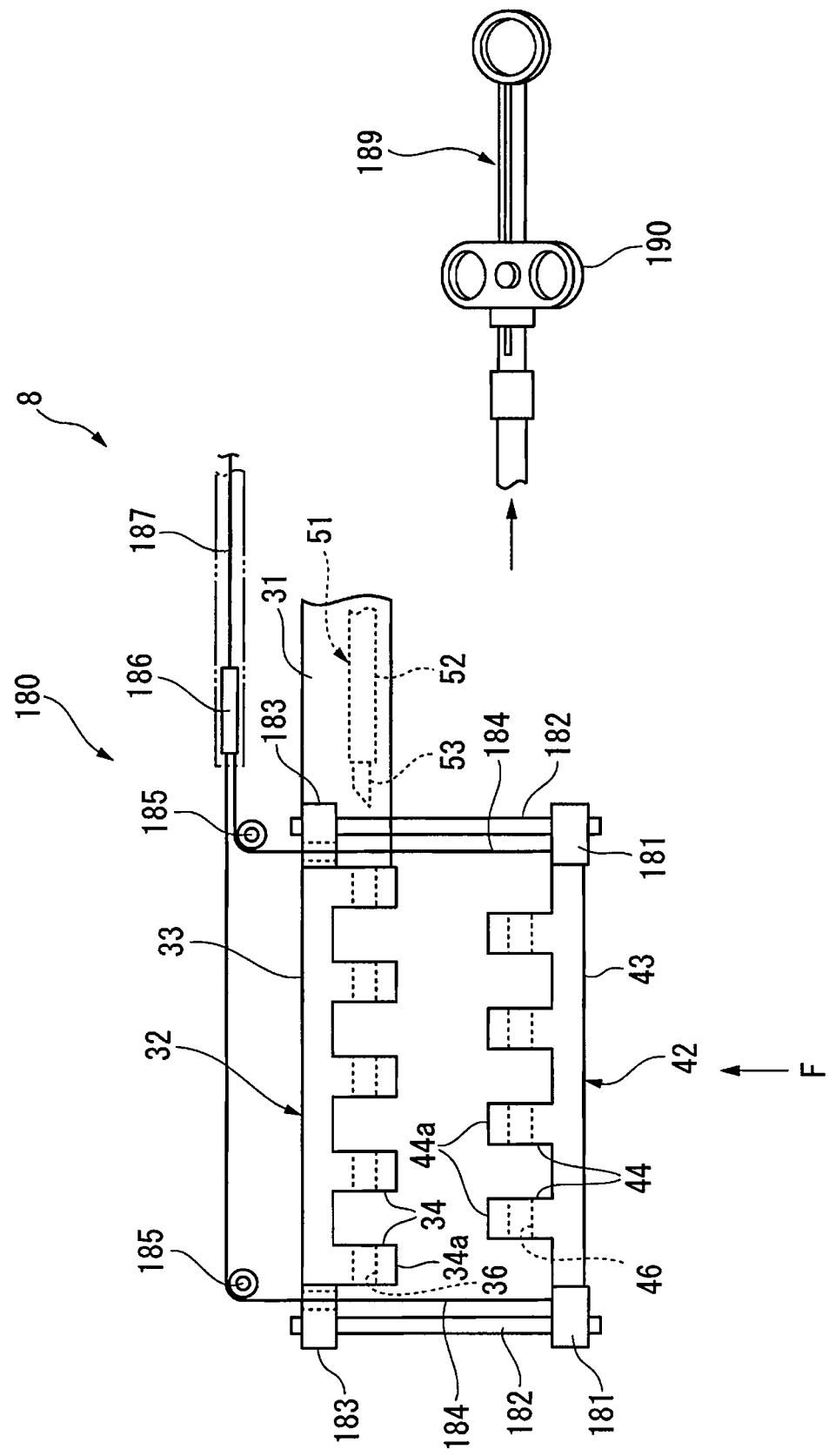
FIG. 62 is a diagram showing the structure of the grasping unit, showing the state in which a second jaw is open.
Figure 63:
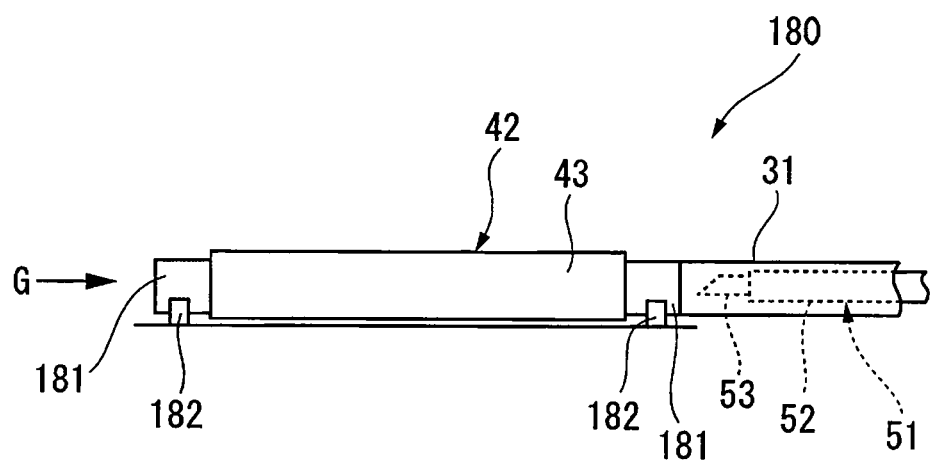
FIG. 63 is a view taken from the direction of the arrow F in FIG. 62.

As shown in FIGS. 62 and 63, a suture unit 180 of the suturing device 8 includes, as a grasping unit, the first jaw 32 and the second jaw 42 that is freely slidable toward or away from the first jaw 32.

The second jaw 42 has a comb-teeth shape in which teeth 44 are arranged at regular intervals on the main body portion 43. Slide portions 181 are provided at the proximal and distal ends of the second jaw 42. Through-holes are formed in the slide portions 181 in a direction parallel to each of the teeth 44, and the pair of rails 182 are inserted through respective through-holes one by one. The rails 182 are parallel to each other, and respective ends of the pair of rails 182 are held at holding portions 183 provided at the proximal and distal ends of the first jaw 32.

To the slide portions 181 of the second jaw 42, wires 184 are connected at positions closer to the longitudinal center of the second jaw 42 than the pair of rails 182. The wires 184 are passed through the holding portions 183 of the first jaw 32 and are then drawn in the forward and backward movement directions while assuming the shape of the outer circumference of a pin 185 fixed to the inner wall of the chamber 4. Then, the wires 184 are incorporated into a single wire at a connection pipe 186, and the single wire is connected to an operation wire 187. The operation wire 187 is passed through a sheath 188 fixed to the inner wall of the overtube 2 and is connected to a slider 190 of an operator-side operation portion 189 outside the body.

Figure 64:
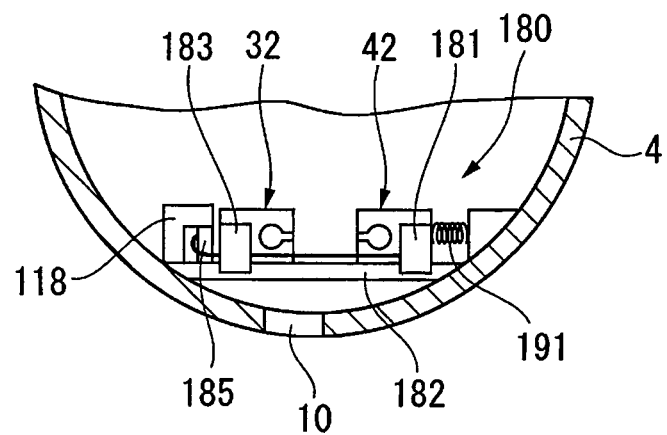
FIG. 64 is a view taken from the direction of the arrow G in FIG. 63.

As shown in FIG. 64, the pair of rails 182 are fixed to the inner wall of the chamber 4. The slide portions 181 are connected to the inner wall of the chamber 4 via an elastic member 191 such as a coil spring. Under unloaded conditions, the second jaw 42 is biased in a direction for moving the second jaw 42 away from the first jaw 32.

Figure 65:
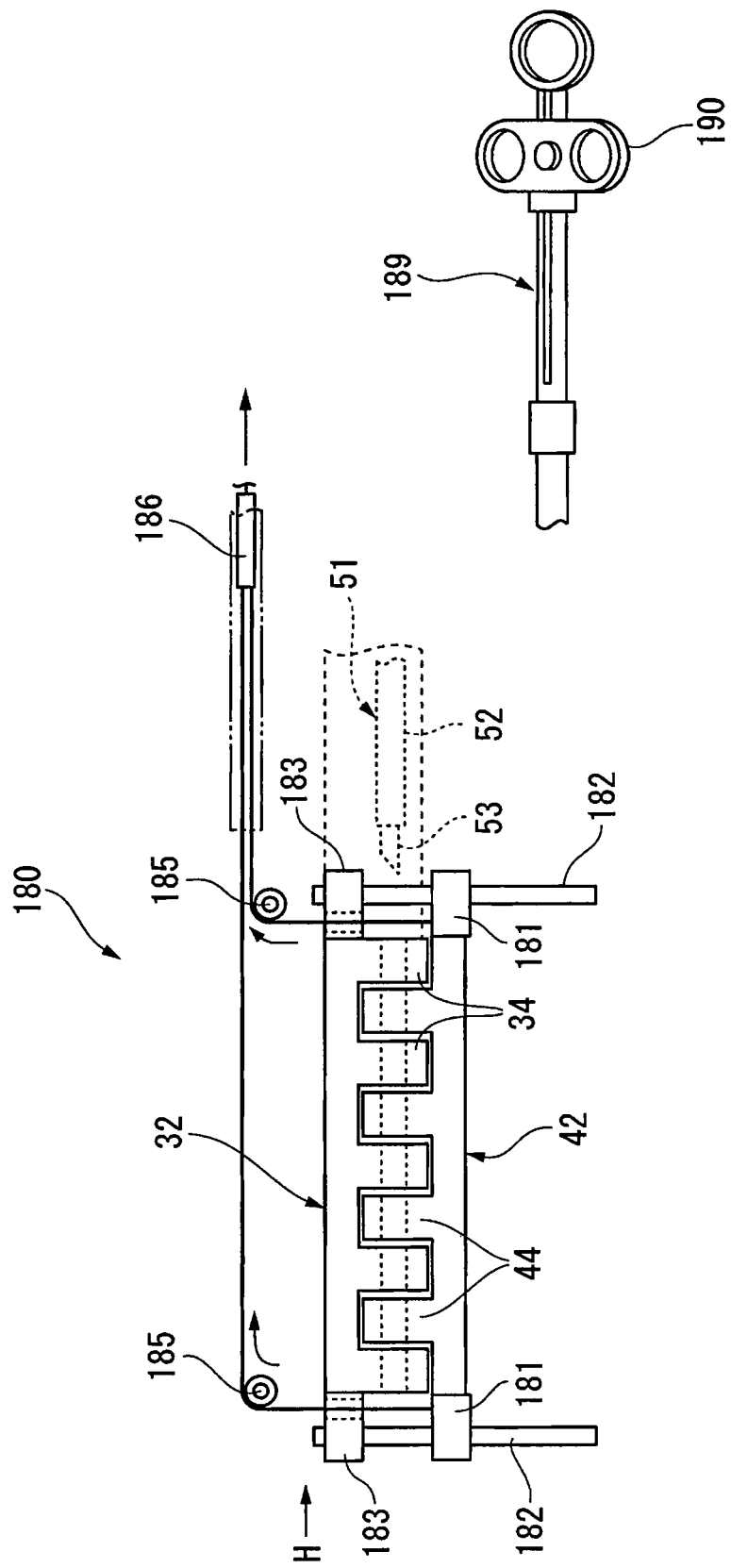
FIG. 65 is a diagram showing the structure of the grasping unit, showing the state in which a second jaw is closed.
Figure 66:
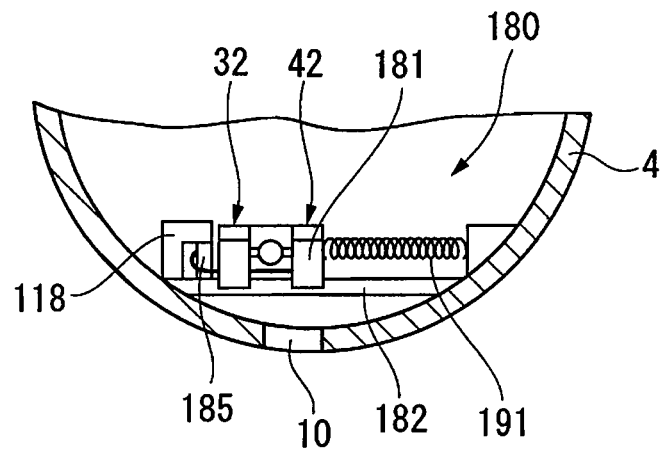
FIG. 66 is a view taken from the direction of the arrow H in FIG. 65.

In the suturing device 8, in the initial state, the suture unit 180 is open and positioned over the lateral hole 10. When a handle 190 is pulled after the lesion W1 is drawn in by the grasping forceps 15, the operation wire 187 is pulled, causing the wires 184 to pull the second jaw 42 so as to be moved toward the first jaw 32. As a result, as shown in FIGS. 65 and 66, the second jaw 42 is slid to a position where the second jaw 42 engages with the first jaw 32 while resisting the force of the elastic member 191.

With this, the biological tissues α and β are sandwiched between the first and second jaws 32 and 42 in a corrugated shape. Then, the biological tissues α and β are sutured in a corrugated manner using the tissue penetrating needle 51. When the suture treatment is completed, the tissue penetrating needle 51 is removed from the biological tissues α and β, and the operator's hand is released from the handle 190. Then, the second jaw 42 is pulled by the restoring force of the elastic member 191, thereby opening the first and second jaws 32 and 42.

Figure 67:
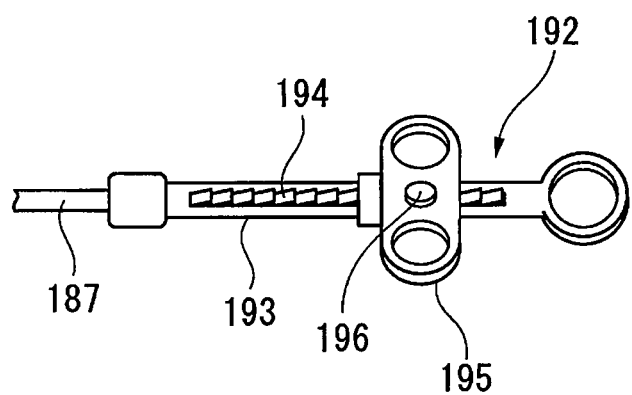
FIG. 67 is a diagram showing an example of an operator-side operation portion of the grasping unit.

The use of a ratchet-type operator-side operation portion 192 as shown in FIG. 67 may enable maintenance of the closed state or the predetermined degree of opening of the first and second jaws 32 and 42. The operator-side operation portion 192 includes ratchet teeth arranged in the longitudinal direction on an operation portion main body 193. A claw that engages with ratchet teeth 194 is formed in a handle 195. The engagement between the ratchet teeth 194 and the claw is released by a button 196 on the handle 195.

According to the present embodiment, the grasping unit includes the first and second jaws 32 and 42 that are opened and closed in a sliding manner. Thus, the grasping unit can be opened or closed while maintaining the same width from the proximal end side to the distal end side. Moreover, a closing (grasping) force, substantially of the same strength can be applied to the distal and proximal end sides. Since the first and second jaws 32 and 42 are attached to the inner wall of the chamber 4, it is possible to place the jaws so as to be opposed to the lateral hole 10 and to thus stabilize the operations.

Embodiment 7

A seventh embodiment will be described with reference to FIGS. 68 to 73. Components similar or identical to those of the afore-described embodiments will be referenced by the same reference numerals, and overlapping descriptions will be omitted.

Figure 68:
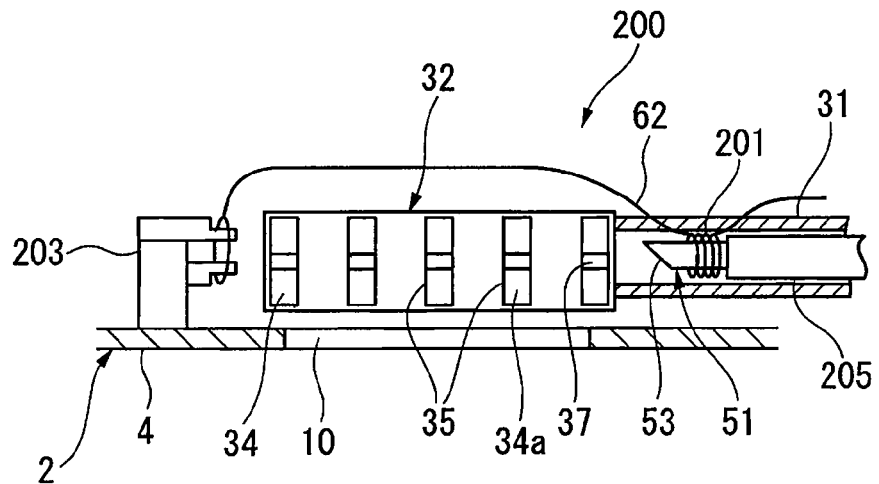
FIG. 68 is a side-sectional view showing the structure of the suture unit.
Figure 69:
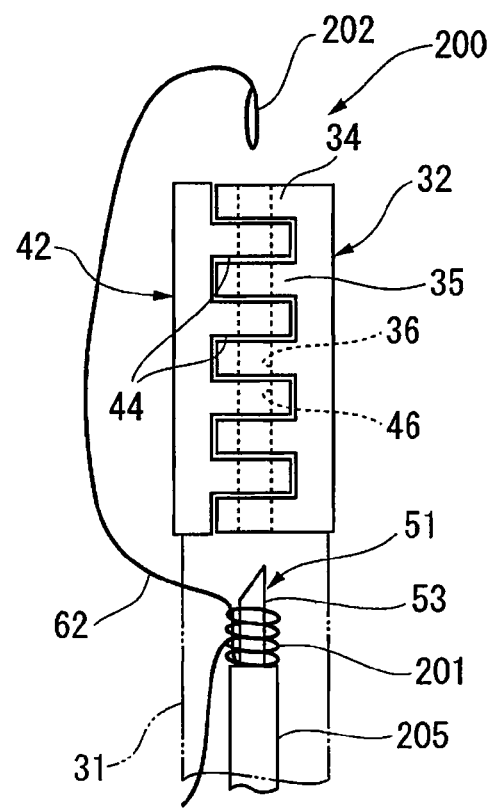
FIG. 69 is a diagram for explaining the operations of the suture unit.
Figure 70:
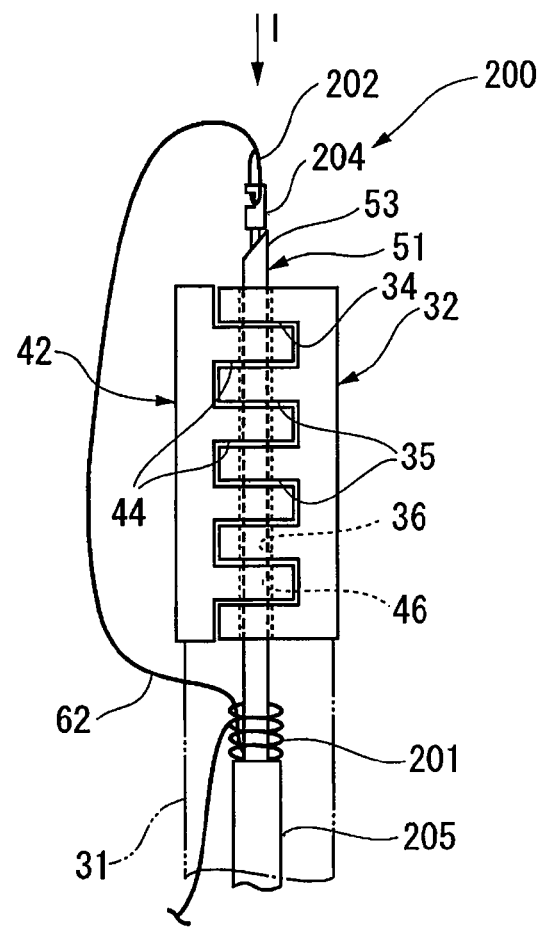
FIG. 70 is a diagram for explaining the operations of the suture unit, showing the state in which the tissue penetrating needle is protruded out.

As shown in FIGS. 68 to 70, a suture unit 200 of the suturing device 8 includes, as a grasping unit, the first jaw 32 and the second jaw 42 that can be freely opened or closed with respect to the first jaw 32. The tissue penetrating needle 51 is inserted through the shaft portion 31 of the first jaw 32 so as to be freely movable forward or backward. The suture thread 62 is loosely bound to the exposed portion of the needle portion 53, forming a knot 201.

One end of the suture thread 62 is drawn outside the body. The other end of the suture thread 62 is drawn to the distal end sides of the first and second jaws 32 and 42 while bypassing the first and second jaws 32 and 42. A loop 202 provided at the distal end of the suture thread 62 is hooked on a hook portion 203 (see FIG. 68) that protrudes from the inner wall of the chamber 4. A hook 204 (see FIG. 70) is provided within the tissue penetrating needle 51 so as to be freely moved forward or backward. The hook 204 is connected to the slider 20 of the first operation portion 16 shown in FIG. 1. Around the outer surface of the tissue penetrating needle 51, a knot pusher 205 capable of pressing the knot 201 is provided so as to be freely moved toward or backward.

In the present embodiment, in a manner similar to the afore-described embodiments, after the lesion W1 is drawn into the chamber 4, the biological tissues α and β on the outer circumference of the lesion W1 are sutured. During the suture treatment, the second jaw 42 is moved to sandwich the biological tissues α and β in a corrugated shape between the first and second jaws 32 and 42. After this, the tissue penetrating needle 51 is moved forward to be sequentially penetrated through the teeth 34, 35, and 44 and the biological tissues α and β.

Then, the first operation portion 16 is operated to allow the hook 204 to protrude out from the distal end of the needle portion 53 so that the hook 204 is hooked on the loop 202 at the distal end of the suture thread 62 that is hooked on the hook portion 203. In this state, when the hook 204 is moved backward, the loop 202 is unhooked from the hook portion 203 and is received in the needle portion 53.

Figure 71:
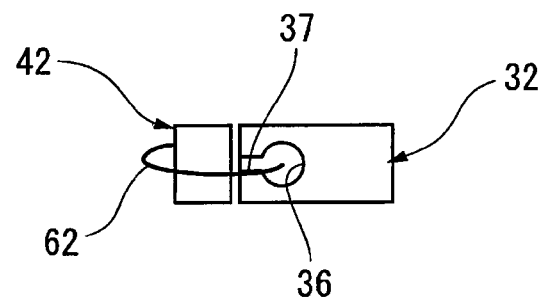
FIG. 71 is a view taken from the direction of the arrow I in FIG. 70, showing the state in which the tissue penetrating needle is withdrawn.

Thereafter, the first operation portion 16 is operated to move the tissue penetrating needle 51 in the backward direction. With this, as shown in FIG. 71, the suture thread 62 is drawn into the through-hole 36 of the distal tooth 34 and is then sequentially passed through the teeth 34, 35, 44 and the biological tissues α and β from the distal end side. When the tissue penetrating needle 51 is pulled out from the first and second jaws 32 and 42, the suture thread 62 is passed through the biological tissues α and β.

Figure 72:
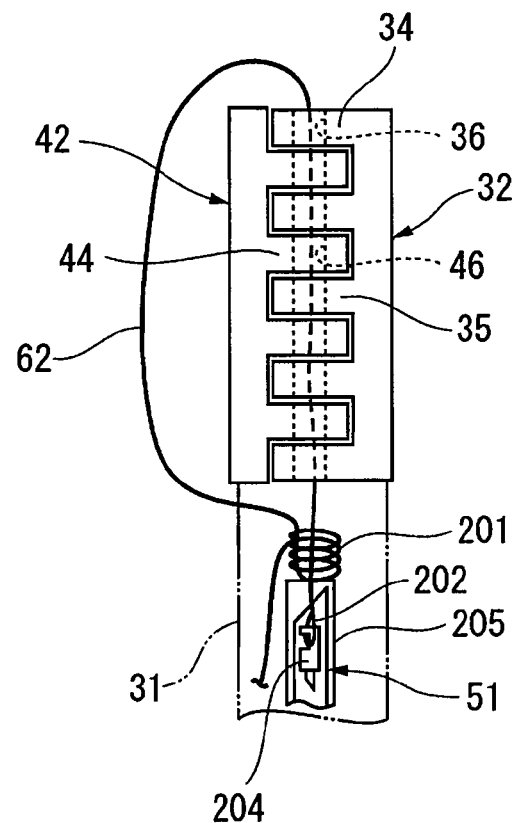
FIG. 72 is a diagram showing the state in which a knot is extruded by a knot pusher.

When the knot pusher 205 is moved forward, as shown in FIG. 72, the knot 201 is extruded closer to the distal end side than the needle portion 53. As a result, the suture thread 62 having passed through the biological tissues α and β is passed through the knot 201 and is drawn out to the operator side.

Figure 73:
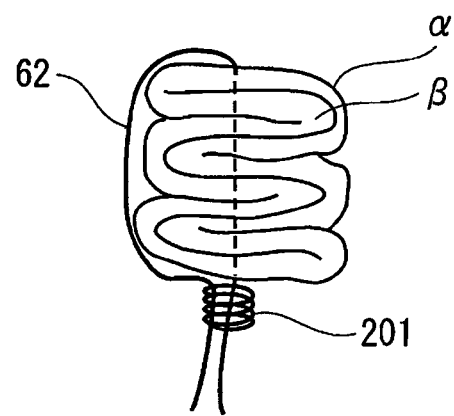
FIG. 73 is a diagram showing a biological tissue that is sutured by a suturing tool.

When the suture unit 200 is moved backward after the second jaw 42 is opened, the biological tissues α and β through which the suture thread 62 has been passed in a corrugated manner remain between the first and second jaws 32 and 42. And, the end of the suture thread 62 connected from the knot 201 and the end of the suture thread 62 drawn out after passing through the knot 201 are pulled by the backward movement of the suture unit 200. As a result, as shown in FIG. 73, the biological tissues α and β are overlapped with each other in a corrugated shape, and the knot 201 is fastened. The remaining portion of the suture thread 62 is cut by scissor forceps or the like that is inserted through the endoscope 7.

According to the present embodiment, since the suturing tool is composed only of the suture thread 62, it is possible to minimize the number of elements detained in the body. Since the suture treatment can be performed such that the biological tissues α and β are fastened after the end of the suture thread 62 is passed through the knot 201, it is possible to simplify the procedure.

Embodiment 8

An eighth embodiment will be described with reference to FIGS. 74 to 76. Components similar or identical to those of the first embodiment will be referenced by the same reference numerals, and overlapping descriptions will be omitted.

Figure 74:
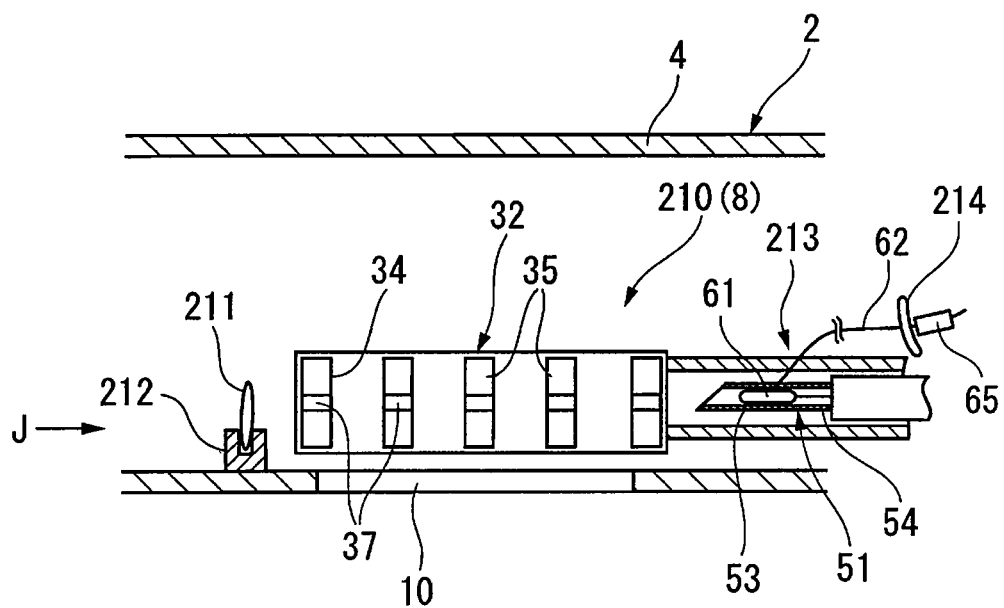
FIG. 74 is a side-sectional view showing the structure of the suturing tool.
Figure 75:
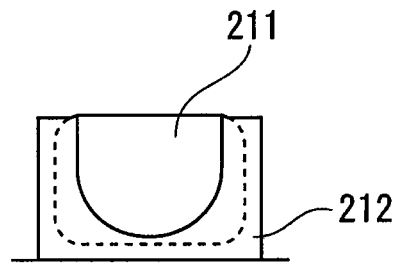
FIG. 75 is a view taken from the direction of the arrow J in FIG. 74, showing a first pre-jet and a holding portion.

As shown in FIG. 74, the suturing device 8 includes a suture unit 210. On a more distal side of the suturing device 8 than the suture unit 210, a first pre-jet 211 used as a retaining patch is held at a holding portion 212. As shown in FIGS. 74 and 75, the first pre-jet 211 is a thin, rectangular member having chamfered corners. The holding portion 212 protrudes from the inner wall of the chamber 4 and has a substantially U shape that is open toward the inside of the chamber 4, forming a slit so that the peripheral border of the first pre-jet 211 is sandwiched between both ends of the U shape.

The first pre-jet 211 constitutes a suturing tool 213. The suturing tool 213 also includes the T bar 61, the suture thread 62, a second pre-jet 214, and the stopper 65. The second pre-jet 214 is provided at the distal end side of the stopper 65, and the suture thread 62 is passed through an approximately central portion of the second pre-jet 214. The second pre-jet 214 is substantially of the same shape and formed of the same material as the first pre-jet 211.

When suturing the biological tissues α and β, in the state in which the biological tissues α and β are sandwiched between the first and second jaws 32 and 42 (only the first jaw 32 is shown in FIG. 74), the first operation portion 16 is operated to move the tissue penetrating needle 51 in the forward direction. The tissue penetrating needle 51 is sequentially passed through the teeth 34, 35, and 44, the biological tissues α and β, and the approximately central portion of the first pre-jet 211 from the operator side.

Then, the pusher rod 54 is moved forward to extrude the T bar 61 to a more distal side than the first pre-jet 211. After this, the tissue penetrating needle 51 is moved backward to remove the needle portion 53. When the second jaw 42 is moved so as to separate the suture unit 210 from the biological tissues α and β, the suture thread 62 remains after being passed through the biological tissues α and β in a corrugated manner. Incidentally, the holding portion 212 of the first pre-jet 211 holds only the peripheral border of the first pre-jet 211. Therefore, when the stopper 65 is moved forward to pull the suture thread 62, the first pre-jet 211 is pulled out from the holding portion 212 by being pulled by the T bar 61.

Figure 76:
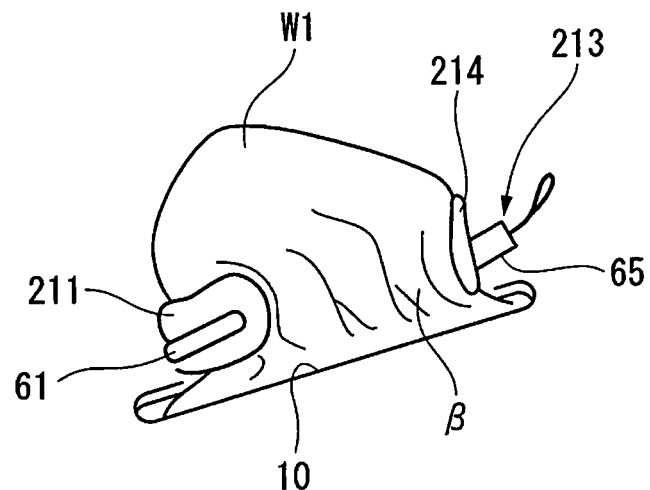
FIG. 76 is a diagram showing a treatment target portion that is sutured by the suturing tool.

As a result, as shown in FIG. 76, the T bar 61 is pressed toward the distal end of the biological tissues α and β with the first pre-jet 211 interposed therebetween. Meanwhile, the stopper 65 is pressed toward the proximal end of the biological tissues α and β with the second pre-jet 214 interposed therebetween. Accordingly, the biological tissues α and β are sutured. The procedure of the drawing-in and entire resection of the lesion W1 is similar to that of the first embodiment.

In the present embodiment, since the suturing tool 213 includes the first and second pre-jets 211 and 214, the T bar 61 or the stopper 65 does not make direct contact with the biological tissues α and β. Therefore, it is possible to prevent a load from being concentrated on a partial area of the biological tissues α and β. Other advantages of the present embodiment are the same as the afore-described embodiments.

The present invention is not limited to the afore-described embodiments but various modifications are possible.

Figure 77:
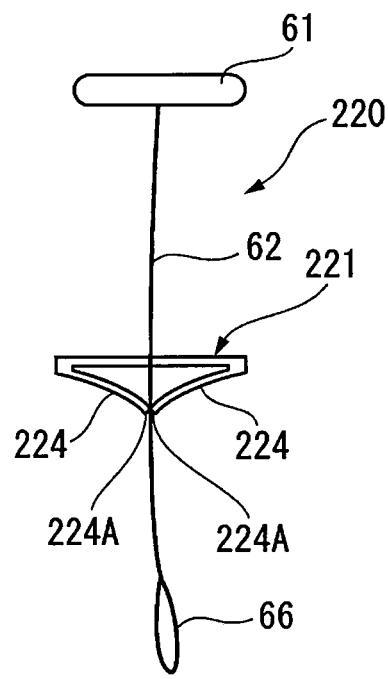
FIG. 77 is a diagram showing the structure of the suturing tool.
Figure 78:
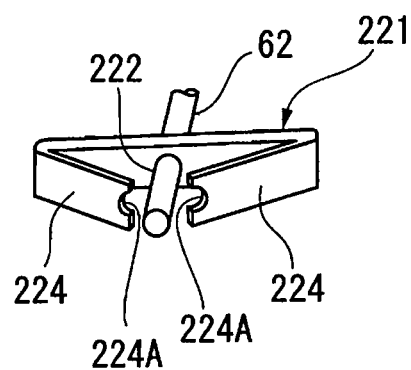
FIG. 78 is a perspective view showing the structure of a stopper.
Figure 79:
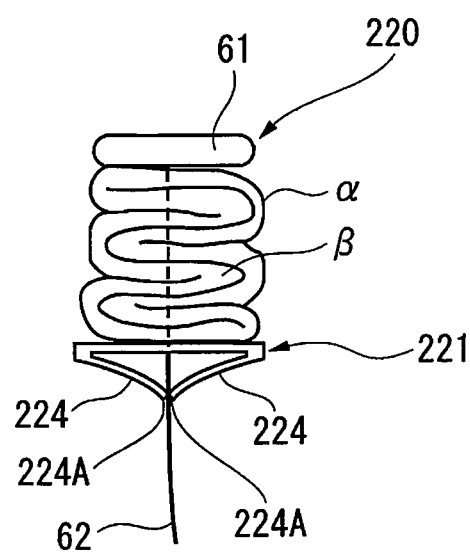
FIG. 79 is a diagram showing the treatment target portion that is sutured by the suturing tool.

For example, a suturing tool 220 as shown in FIG. 77 may be employed. The T bar 61 is attached to the distal end of a suture thread 62, the suture thread 62 is passed through a fixing member 211, and a loop 66 is formed at the proximal end of the suture thread 62. As shown in FIG. 78, the fixing member 221 is formed of a long and thin plate having a hole 222 at the center, through which the suture thread 62 is inserted. Both end portions of the plate are obliquely bent toward the proximal end portion of the suture thread 62, forming a plate spring portion 224.

The plate spring portion 224 has opposite end portions 224A that are cut in a semi-circular shape. The plate spring portion 224 makes sliding contact with the suture thread 62 and can be elastically deformed toward the loop 66 of the suture thread 62, i.e., in the direction for widening the gap between the opposite end portions 224A. Therefore, the suturing tool 220 allows the fixing member 221 to move toward the T bar 61.

However, the plate spring portion 224 is not deformed in the direction for narrowing the gap between the opposite end portions 224A because they interfere with each other. In addition, because the suture thread 62 is fastened by the end portions 224A, the fixing member 221 is not moved toward the loop 66.

As shown in FIG. 77, when the fixing member 221 is moved forward along the suture thread 62 having passed through the biological tissues α and β, the fixing member 221 having a large surface area abuts the proximal end side of biological tissues α and β. As described above, since the fixing member 221 is not moved toward the loop 66, i.e., in the direction of departing from the biological tissues α and β, the biological tissues α and β can be sutured while abutting the T bar 61 and the fixing member 221 having the large surface area.

At this time, the length of the T bar 61 and the fixing member 221 is preferably longer than the width of the biological tissues α and β overlapped in a corrugated manner. With this, it is possible to press the entire width of the biological tissues α and β. Thus, it is possible to suture the biological tissues α and β in a secure manner without leaving any gap.

Figure 80:
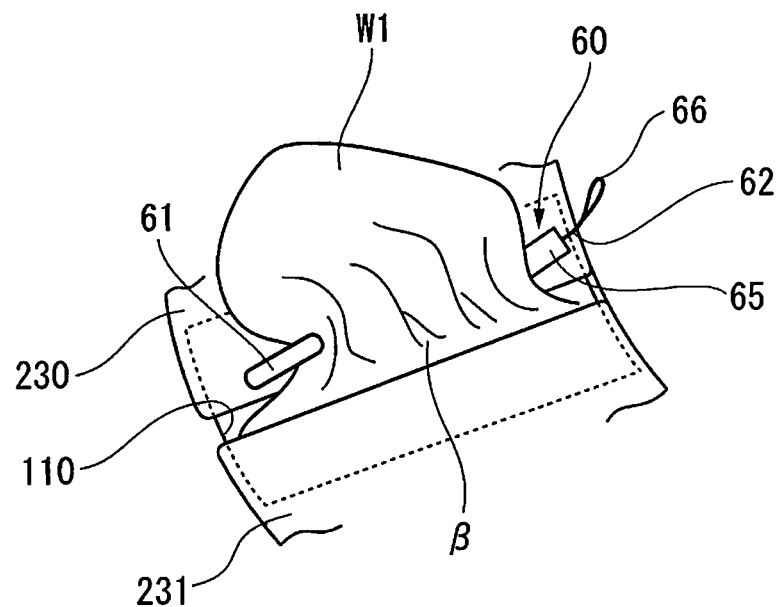
FIG. 80 is a diagram showing the state in which a suture treatment is performed while narrowing the width of the lateral hole using the slider cover.
Figure 81:
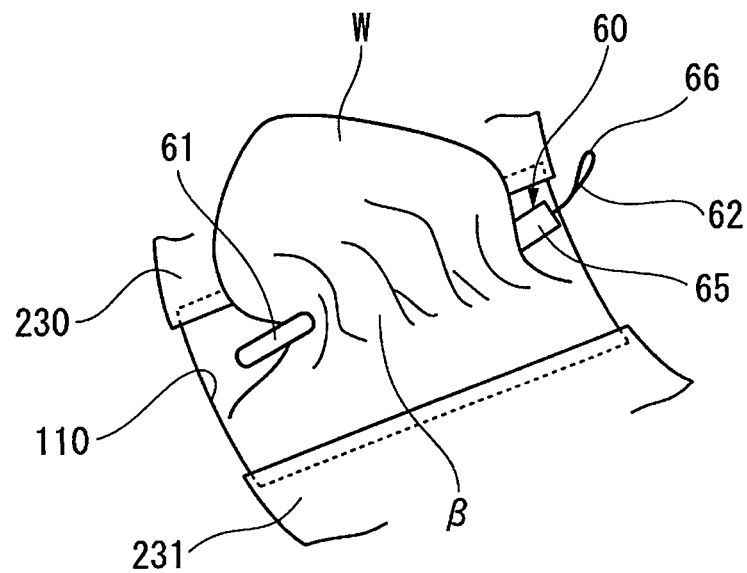
FIG. 81 is a diagram showing the state in which the slider cover is open after the suture treatment is performed.

In this case, as shown in FIGS. 80 and 81, a slider cover 230 (a first entanglement preventing portion) and another slider cover 231 (a second entanglement preventing portion) may be provided so as to cover the lateral hole 110. When the lesion W1 is drawn into the lateral hole 110, the opening of the lateral hole 110 is narrowed to prevent other organs W3 from being drawn into the narrow opening of the lateral hole 110. When the suture treatment is completed, the slider cover 230 is moved to widen the opening of the lateral hole 110, allowing the biological tissues α and β attached to the suturing tool 220 to come out of the chamber 4 in an easy manner. As the mechanism for controlling the opening of the lateral hole 110, any mechanism described in connection with the afore-described embodiments can be used.

Figure 82:
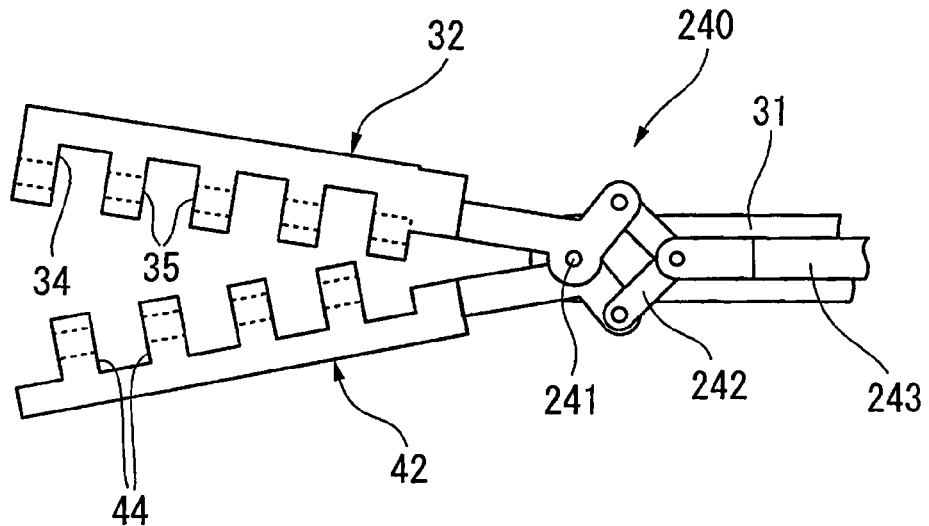
FIG. 82 is a diagram showing the structure of a bi-parting grasping unit.
Figure 83:
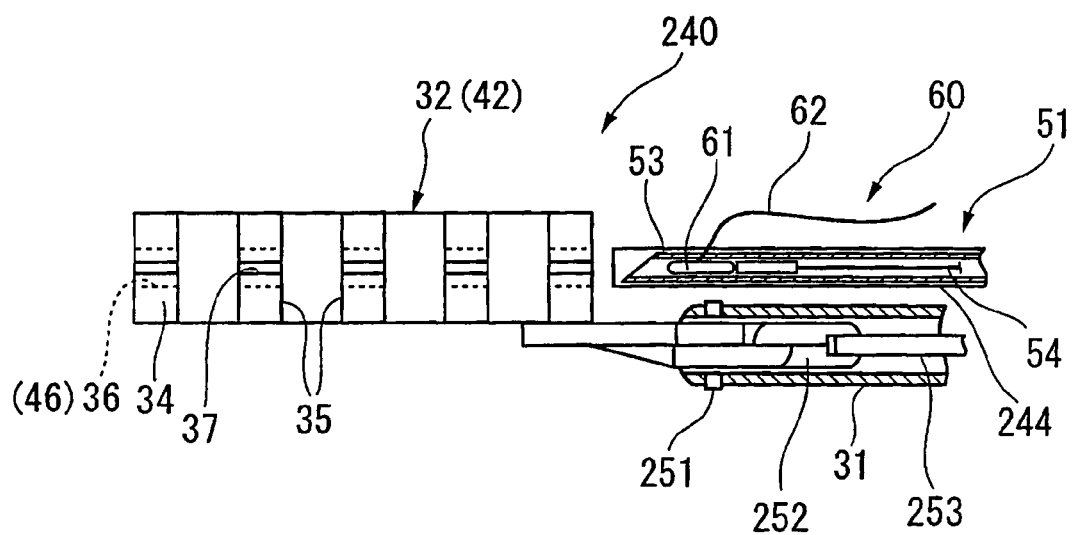
FIG. 83 is a side-sectional view of a suture unit including the grasping unit shown in FIG. 82.

Similar to a suture unit 240 as shown in FIGS. 82 and 83, the first and second jaws 32 and 42 may be opened or closed in a bi-parting manner. In the distal end portion of the shaft portion 31, the first and second jaws 32 and 42 are pivotably supported on a pin 241. The proximal end portions of the first and second jaws 32 and 42 are connected to an operation member 243 via a link mechanism 242. The operation member 243 is connected to the slider 26 of the second operation portion 17 and is adapted to be freely moved forward or backward with respect to the shaft portion 31.

In this case, as shown in FIG. 83, the tissue penetrating needle 51 may be separately provided. The tissue penetrating needle 51 is inserted through a sheath 244 and is positioned such that the distal end of the needle portion 53 is opposed to the through-holes 36 and 46.

The afore-described embodiments may be suitably combined with each other. For example, the lateral hole 170 of the fifth embodiment may be narrowed, or the valve elements 140 and 141 of the third embodiment may be attached. Additionally or alternatively, the suture units 180, 200, 210, or 240 of the sixth to eighth embodiments may be employed in any one of the first to fifth embodiments. In this case, the tissue restricting member is not limited to the lateral hole 10, but the wall surfaces in the longitudinal direction of the lateral hole 110 or the like may be used as the tissue restricting member.

The mechanism for drawing the treatment target portion into the endoscope 7 is not limited to the grasping forceps 15, but various other drawing-in methods such as suctioning may be used.

INDUSTRIAL APPLICABILITY

The present invention is applicable to an endoscopic treatment tool which, when performing a treatment by drawing a treatment target portion into an endoscope, can prevent other organs from being drawn into the endoscope together with the treatment target portion.

The invention claimed is:

1. A pressing member, comprising:
    a pressing member main body which has a chamber that has a cylindrical shape elongated from a proximal end to a distal end thereof, the pressing member main body being disposed between a treatment target portion of a biological tissue and an endoscope inserted into a body of a patient for treatment of the treatment target portion of the biological tissue, the pressing member main body including a lateral hole provided at side surface of the chamber;
    a slider which is provided at an inner surface of the chamber, the slider being configured to move along the side surface of the pressing member main body in a direction crossing the lateral hole where an end portion of the slider approaches or departs from a peripheral border portion of the lateral hole so as to adjust a clearance between the peripheral border portion of the lateral hole and the end portion of the slider;
    rails in which the slider is configured to slide and which are at the inner surface of the chamber, the rails being configured to guide the slider to move along the side surface of the pressing member main body in a peripheral direction of the lateral hole; and
    wires provided at the inner surface of the chamber and connected to the slider, the wires configured to operate movements of the slider in the peripheral direction by being pulled in a direction from the distal end to the proximal end; wherein
    the end portion of the slider and the peripheral border portion are capable of pressing the treatment target portion that is drawn into the pressing member main body.

2. The pressing member according to claim 1, wherein the entanglement preventing portion comprises:
    a first surface opposed to the endoscope;
    a second surface opposed to the treatment target portion; and
    a pressing portion disposed on a surface that connects the first surface and the second surface to each other, the pressing portion being configured to, when drawing the treatment target portion into the endoscope via the pressing member main body, produce a pressing force in a direction substantially perpendicular to the drawing-in direction of the treatment target portion, to maintain the thickness of the drawn-in treatment target portion to a predetermined thickness, and to thus prevent other organs on the periphery of the treatment target portion from being drawn into the endoscope together with the treatment target portion.

3. The pressing member according to claim 1, wherein the entanglement preventing portion is a displacing member that can be located between the treatment target portion and other organs on the periphery of the treatment target portion, the pressing member main body comprising:
    a first opening through which the treatment target portion is drawn into the endoscope via the pressing member; and
    a second opening disposed closer to a proximal end than the first opening, through which the displacing member is delivered from the endoscope toward the treatment target portion via the pressing member.

4. The pressing member according to claim 1, wherein the pressing member main body is movable with respect to the endoscope.

5. The pressing member according to claim 1, wherein the pressing member main body comprises:
    an overtube having a lumen that allows insertion of the endoscope therethrough;
    a flexible insertion guide that extends from a distal end of the overtube;
    a tapered portion corresponding to a transitional portion between the overtube and the insertion guide; and
    an opening formed in the tapered portion and having a space through which the treatment target portion is drawn in.

6. An endoscopic treatment system, comprising:
    the endoscope;
    the pressing member according to claim 1;
    a draw-in portion for drawing the treatment target portion into an endoscope-side area; and
    a treatment portion for treating the treatment target portion.

7. The pressing member according to claim 1, wherein
    a longitudinal length of the lateral hole of the pressing member main body is formed so as to be shorter than a length between a proximal end portion and a distal end portion of a grasping member configured to grasp the treatment target portion of the biological tissue.

8. The pressing member according to claim 1, further comprising
    pins which are fixed to the inner surface of the chamber, wherein
    the wires are drawn along the rails and are turned to a longitudinal direction of the chamber by being hooked on an outer circumference of the pins.

* * * * *